United States Patent
Balan et al.

(10) Patent No.: US 7,534,798 B2
(45) Date of Patent: *May 19, 2009

(54) VANILLOID RECEPTOR LIGANDS AND THEIR USE IN TREATMENTS

(75) Inventors: Chenera Balan, Thousand Oaks, CA (US); Ning Chen, Thousand Oaks, CA (US); Elizabeth M. Doherty, Newbury Park, CA (US); Vijay Keshav Gore, Thousand Oaks, CA (US); Mark H. Norman, Thousand Oaks, CA (US); Hui-Ling Wang, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 513 days.

This patent is subject to a terminal disclaimer.

(21) Appl. No.: 11/056,534

(22) Filed: Feb. 11, 2005

(65) Prior Publication Data
US 2005/0182067 A1 Aug. 18, 2005

Related U.S. Application Data

(60) Provisional application No. 60/543,985, filed on Feb. 11, 2004.

(51) Int. Cl.
A01N 43/54 (2006.01)
A61K 31/505 (2006.01)
C07D 239/02 (2006.01)
C07D 239/42 (2006.01)
C07D 403/00 (2006.01)

(52) U.S. Cl. .............. 514/256; 514/269; 544/319; 544/326; 544/328

(58) Field of Classification Search ........... 544/319, 544/326, 328; 514/269, 256
See application file for complete search history.

(56) References Cited

U.S. PATENT DOCUMENTS

| | | | |
|---|---|---|---|
| 5,272,167 A | 12/1993 | Girijavallabhan et al. | |
| 5,459,144 A | 10/1995 | Girijavallabhan et al. | |
| 5,750,532 A | 5/1998 | Girijavallabhan et al. | |
| 5,916,887 A | 6/1999 | Singh et al. | |
| 5,932,590 A | 8/1999 | Ciccarone et al. | |
| 5,936,084 A | 8/1999 | Jirousek et al. | |
| 5,959,123 A | 9/1999 | Singh et al. | |
| 5,965,569 A | 10/1999 | Camps Garcia et al. | |
| 5,969,140 A | 10/1999 | Ukita et al. | |
| 6,093,737 A | 7/2000 | Anthony et al. | |
| 6,153,619 A * | 11/2000 | Wood et al. | 514/269 |
| 6,255,489 B1 | 7/2001 | Klintz et al. | |
| 6,306,866 B1 * | 10/2001 | Wood et al. | 514/274 |
| 6,407,111 B1 | 6/2002 | Bös et al. | |
| 6,562,847 B1 | 5/2003 | Lee | |
| 6,569,847 B1 | 5/2003 | Singh et al. | |
| 6,593,330 B2 | 7/2003 | Nilsson | |
| 6,596,773 B2 | 7/2003 | Bös et al. | |
| 6,610,677 B2 | 8/2003 | Davies et al. | |
| 6,613,776 B2 | 9/2003 | Knegtel et al. | |
| 7,053,088 B2 * | 5/2006 | Doherty et al. | 514/247 |
| 7,144,888 B2 * | 12/2006 | Doherty et al. | 514/269 |
| 7,301,022 B2 * | 11/2007 | Bo et al. | 544/239 |
| 7,335,672 B2 * | 2/2008 | Norman et al. | 514/345 |
| 2002/0151712 A1 | 10/2002 | Lin et al. | |
| 2003/0008883 A1 * | 1/2003 | Grant et al. | 514/256 |
| 2003/0195201 A1 | 10/2003 | Bo et al. | |
| 2004/0023977 A1 | 2/2004 | Larsen et al. | |
| 2004/0038969 A1 | 2/2004 | Doherty et al. | |
| 2004/0082780 A1 | 4/2004 | Doherty et al. | |
| 2004/0176385 A1 * | 9/2004 | Nuss et al. | 514/252.14 |
| 2004/0204386 A1 | 10/2004 | Bhatt et al. | |

(Continued)

FOREIGN PATENT DOCUMENTS

EP 0 168 262 1/1986

(Continued)

OTHER PUBLICATIONS

Lee, et al., N-(3-Acloxy-2-benzylpropyl)-N-[4-{methylsufonylamino)benzyl]thiourea Analogues: Novel Potent and High Affinity Antagonists and Partial Antagonists of the Vanilloid Receptor, J Med. Chem., 46: 3116-3126 (2003).

*Primary Examiner*—James O Wilson
*Assistant Examiner*—Erich A Leeser
(74) *Attorney, Agent, or Firm*—Richard V. Person

(57) ABSTRACT

Compounds having the general structure

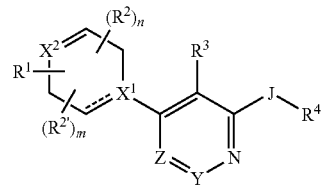

and compositions containing them, for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

12 Claims, No Drawings

U.S. PATENT DOCUMENTS

| | | | |
|---|---|---|---|
| 2005/0014753 A1* | 1/2005 | Ding et al. | 514/241 |
| 2006/0040947 A1* | 2/2006 | Blurton et al. | 514/252.01 |
| 2006/0235036 A1* | 10/2006 | Doherty et al. | 514/275 |
| 2006/0241296 A1* | 10/2006 | Doherty et al. | 544/295 |

FOREIGN PATENT DOCUMENTS

| | | |
|---|---|---|
| EP | 0 937 459 | 1/1999 |
| WO | WO 92/04333 | 3/1992 |
| WO | WO 97/00612 | 1/1997 |
| WO | WO 97/13754 | 4/1997 |
| WO | WO 97/41127 | 11/1997 |
| WO | WO 98/12176 | 3/1998 |
| WO | WO 98/12210 | 3/1998 |
| WO | WO 98/23155 | 6/1998 |
| WO | WO 98/23156 | 6/1998 |
| WO | WO 98/28980 | 7/1998 |
| WO | WO 99/12911 | 3/1999 |
| WO | WO 99/28314 | 6/1999 |
| WO | WO 99/41248 | 8/1999 |
| WO | WO 99/51241 | 10/1999 |
| WO | WO 00/59881 | 10/2000 |
| WO | WO 00/62778 | 10/2000 |
| WO | WO 01/05768 | 1/2001 |
| WO | WO 01/07032 | 2/2001 |
| WO | WO 01/07401 | 2/2001 |
| WO | WO 01/14331 | 3/2001 |
| WO | WO 01/19817 | 3/2001 |
| WO | WO 01/47921 | 7/2001 |
| WO | WO 01/53263 | 7/2001 |
| WO | WO 01/54503 | 8/2001 |
| WO | WO 01/74331 | 10/2001 |
| WO | WO 01/76582 | 10/2001 |
| WO | WO 02/00651 | 1/2002 |
| WO | WO 02/16324 | 2/2002 |
| WO | WO 02/18339 | 3/2002 |
| WO | WO 02/22602 | 3/2002 |
| WO | WO 02/26712 | 4/2002 |
| WO | WO 02/32872 | 4/2002 |
| WO | WO 02/45652 | 6/2002 |
| WO | WO 02/50052 | 6/2002 |
| WO | WO 02/50065 | 6/2002 |
| WO | WO 02/079197 | 10/2002 |
| WO | WO 02/080853 | 10/2002 |
| WO | WO 02/088111 | 11/2002 |
| WO | WO 03/006471 | 1/2003 |
| WO | WO 03/028729 | 4/2003 |
| WO | WO 03/029210 | 4/2003 |
| WO | WO 03/041649 | 5/2003 |
| WO | WO 03/049702 | 6/2003 |
| WO | WO 03/084953 | 10/2003 |
| WO | WO 03/093242 | 11/2003 |
| WO | WO 03/099284 | 12/2003 |
| WO | WO 2004/000819 | 12/2003 |
| WO | WO 2004/000833 | 12/2003 |
| WO | WO 2004/005283 | 1/2004 |
| WO | WO 2004/014871 | 2/2004 |
| WO | WO 2004/046133 | 6/2004 |
| WO | WO 2004/065378 | 8/2004 |
| WO | WO 2004/089286 | 10/2004 |
| WO | WO 2005/007646 | 1/2005 |
| WO | WO 2005/013982 | 2/2005 |

* cited by examiner

VANILLOID RECEPTOR LIGANDS AND THEIR USE IN TREATMENTS

This application claims the benefit of U.S. Provisional Application No. 60/543,985, filed Feb. 11, 2004, which is hereby incorporated by reference.

BACKGROUND

The vanilloid receptor 1 (VR1) is the molecular target of capsaicin, the active ingredient in hot peppers. Julius et al. reported the molecular cloning of VR1 (Caterina et al., 1997). VR1 is a non-selective cation channel which is activated or sensitized by a series of different stimuli including capsaicin and resiniferatoxin (exogenous activators), heat & acid stimulation and products of lipid bilayer metabolism, anandamide (Premkumar et al., 2000, Szabo et al., 2000, Gauldie et al., 2001, Olah et al., 2001) and lipoxygenase metabolites (Hwang et al., 2000). VR1 is highly expressed in primary sensory neurons (Caterina et al., 1997) in rats, mice and humans (Onozawa et al., 2000, Mezey et al., 2000, Helliwell et al., 1998, Cortright et al., 2001). These sensory neurons innervate many visceral organs including the dermis, bones, bladder, gastrointestinal tract and lungs; VR1 is also expressed in other neuronal and non-neuronal tissues including but not limited to, CNS nuclei, kidney, stomach and T-cells (Nozawa et al., 2001, Yiangou et al., 2001, Birder et al., 2001). Presumably expression in these various cells and organs may contribute to their basic properties such as cellular signaling and cell division.

Prior to the molecular cloning of VR1, experimentation with capsaicin indicated the presence of a capsaicin sensitive receptor, which could increase the activity of sensory neurons in humans, rats and mice (Holzer, 1991; Dray, 1992, Szallasi and Blumberg 1996, 1999). The results of acute activation by capsaicin in humans was pain at injection site and in other species increased behavioral sensitivity to sensory stimuli (Szallasi and Blumberg, 1999). Capsaicin application to the skin in humans causes a painful reaction characterized not only by the perception of heat and pain at the site of administration but also by a wider area of hyperalgesia and allodynia, two characteristic symptoms of the human condition of neuropathic pain (Holzer, 1991). Taken together, it seems likely that increased activity of VR1 plays a significant role in the establishment and maintenance of pain conditions. Topical or intradermal injection of capsaicin has also been shown to produce localized vasodilation and edema production (Szallasi and Blumberg 1999, Singh et al., 2001). This evidence indicates that capsaicin through it's activation of VR1 can regulate afferent and efferent function of sensory nerves. Sensory nerve involvement in diseases could therefore be modified by molecules which effect the function of the vanilloid receptor to increase or decrease the activity of sensory nerves.

VR1 gene knockout mice have been shown to have reduced sensory sensitivity to thermal and acid stimuli (Caterina et al., 2000)). This supports the concept that VR1 contributes not only to generation of pain responses (i.e. via thermal, acid or capsaicin stimuli) but also to the maintenance of basal activity of sensory nerves. This evidence agrees with studies demonstrating capsaicin sensitive nerve involvement in disease. Primary sensory nerves in humans and other species can be made inactive by continued capsaicin stimulation. This paradigm causes receptor activation induced desensitization of the primary sensory nerve—such reduction in sensory nerve activity in vivo makes subjects less sensitive to subsequent painful stimuli. In this regard both capsaicin and resinferatoxin (exogenous activators of VR1), produce desensitization and they have been used for many proof of concept studies in in vivo models of disease (Holzer, 1991, Dray 1992, Szallasi and Blumberg 1999).

VR1 agonists or antagonists have use as analgesics for the treatment of pain of various genesis or aetiology, for example acute, inflammatory and neuropathic pain, dental pain and headache, particularly vascular headache such as migraine, cluster headache and mixed vascular syndromes as well as non-vascular, tension headache. They are also useful as anti-inflammatory agents for the treatment of inflammatory diseases or conditions, for example the treatment of arthritis and rheumatic diseases, osteoarthritis, inflammatory bowel disorders, anxiety, depression, inflammatory eye disorders (e.g. uvetis), inflammatory or unstable bladder disorders (e.g. cystitis and urinary incontinence), psoriasis and skin complaints with inflammatory components, as well as other chronic inflammatory conditions. They are, in particular, useful in the treatment of inflammatory pain and associated hyperalgesia and allodynia. They are also useful in the treatment of neuropathic pain and associated hyperalgesia and allodynia, e.g. trigeminal or herpetic neuralgia, diabetic neuropathy pain, causalgia, sympathetically maintained pain and deafferentation syndromes such as brachial plexus avulsion.

They are also indicated for the use in the prophylactic or curative treatment of asthma, of epithelial tissue damage or dysfunction, e.g. spontaneous lesions, of herpes simplex, and in the control of disturbances of visceral motility at respiratory, genitourinary, gastrointestinal or vascular e.g. for treating wounds, burns, allergic skin reactions, pruritis and vitiligo, for the prophylactic or curative treatment of gastrointestinal disorders such as gastric ulceration, duodenal ulcers, inflammatory bowel disease and diarrhea, gastric lesions induced by necrotising agents, for example ethanol or chemotherapeutic agents, hair growth, for the treatment of vasomotor or allergic rhinitis and for the treatment of bronchial disorders or bladder disorders, such as bladder hyperreflexia.

BIBLIOGRAPHY

Birder-L A. Kanai-A J. de-Groat-W C. Kiss-S. Nealen-M L. Burke-N E. Dineley-K E. Watkins-S. Reynolds-I J. Caterina-M J. (2001) Vanilloid receptor expression suggests a sensory role for urinary bladder epithelial cells. PNAS 98: 23: 13396-13401.

Caterina, M. J, Schumacher, M. A., Tominaga, M., Rosen, T. A., Levine, J. D., and Julius, D, (1997). The capsaicin receptor: a heat-activated ion channel in the pain pathway. Nature 389: 816-824.

Caterina-M J. Leffler-A. Malmberg-A B. Martin-W J. Trafton-J. Petersen-Zeitz K R. Koltzenburg-M. Basbaum-A I. Julius-D (2000) Impaired nociception and pain sensation in mice lacking the capsaicin receptor. Science-(WASH-DC). 288: 5464: 306-313. Cortright-D N. Crandall-M. Sanchez-J F. Zou-T. Krause-J E.

White-G (2001) The tissue distribution and functional characterization of human VR1. Biochemical and Biophysical Research Communications 281: 5: 1183-1189 Dray, A., (1992). Therapeutic potential of capsaicin-like molecules. Life Sciences 51: 1759-1765.

Gauldie-S D. McQueen-D S. Pertwee-R. Chessell-I P. (2001) Anandamide activates peripheral nociceptors in normal and arthritic rat knee joints. British Journal of Pharmacology 132: 3: 617-621.

Helliwell-R J A. McLatchie-L M. Clarke-M. Winter-J. Bevan-S. McIntyre-P (1998) Capsaicin sensitivity is associated with expression of the vanilloid (capsaicin) receptor (VR1) mRNA in adult rat sensory ganglia. Neuroscience Lett. 250: 3: 177-180.

Holzer, P. (1991) Capsaicin: Cellular targets, Mechanisms of Action and selectivity for thin sensory neurons. Pharmacological reviews 43: 2: 143-201

Hwang-S W. Cho-H. Kwak-J. Lee-S Y. Kang-C J. Jung-J. Cho-S. Min-K H. Suh-Y G. Kim-D. Oh-U. (2000) Direct activation of capsaicin receptors by products of lipoxygenases: Endogenous capsaicin-like substances. PNAS 97: 11: 6155-6160.

Mezey-E. Toth-Z E. Cortright-D N. Arzubi-M K. Krause-J E. Elde-R. Guo-A. Blumberg-P M. Szallasi-A (2000) Distribution of mRNA for vanilloid receptor subtype 1 (VR1), and VR1-like immunoreactivity, in the central nervous system of the rat and human. PNAS 97: 7: 3655-3660.

Nozawa-Y. Nishihara-K. Yamamoto-A. Nakano-M. Ajioka-H. Matsuura-N.(2001) Distribution and characterization of vanilloid receptors in the rat stomach. Neuroscience Letters 309: 1: 33-36.

Olah-Z. Karai-L. Iadarola-M J. (2001) Anandamide activates vanilloid receptor 1 (VR1) at acidic pH in dorsal root ganglia neurons and cells ectopically expressing VR1. Journal of Biological Chemistry 276: 33, 31163-31170.

Onozawa-K. Nakamura-A. Tsutsumi-S. Yao-J. Ishikawa-R. Kohama-K. (2000) Tissue distribution of capsaicin receptor in the various organs of rats. Proc. Jpn. Acad. Ser. B, Phys.-Biol. Sci. 76: 5: 68-72.

Premkumar-L S. Ahern-G P. (2000) Induction of vanilloid receptor channel activity by protein kinase C. Nature (London) 408: 6815: 985-990.

Singh-L K. Pang-X. Alexacos-N. Letourneau-R. Theoharides-T C. (1999) Acute immobilization stress triggers skin mast cell degranulation via corticotropin releasing hormone, neurotensin, and substance P: A link to neurogenic skin disorders. Brain Behav. Immun. 13: 3: 225-239.

Szallasi, A. Blumberg-P M (1996) Vanilloid receptors: New insights enhance potential as a therapeutic target. Pain 68: 195-208

Szallasi-A. Blumberg-P M. (1999) Vanilloid (capsaicin) receptors and mechanisms. Pharmacol. Rev. 51: 2: 159-211.

Szabo-T. Wang-J. Gonzalez-A. Kedei-N. Lile-J. Treanor-J. Blumberg-P M. (2000) Pharmacological characterization of the human vanilloid receptor type-1 (hVR1). Society for Neuroscience Abstracts. 26:1-2: 634.18.

Tominaga, M., Caterina, M. J., Malmberg, A. B., Rosen, T. A., Gilbert, H., Skinner, K., Raumann, B. E., Basbaum, A. I., and Julius, D., (1998). The cloned capsaicin receptor integrates multiple pain-producing stimuli. Neuron 21: 531-543.

Yiangou-Y. Facer-P. Dyer-N H C. Chan-C L H. Knowles-C. Williams-N S. Anand-P. (2001) Vanilloid receptor 1 immunoreactivity in inflamed human bowel. Lancet (North American Edition) 357: 9265: 1338-1339.

Yiangou-Y. Facer-P. Ford-A. Brady-C. Wiseman-O. Fowler-C J. Anand-P. (2001) Capsaicin receptor VR1 and ATP-gated ion channel P2X3 in human urinary bladder. BJU International 87: 9: 774-779.

Wang-H. Bian-D. Zhu-D. Zajic-G. Loeloff-R. Lile-J. Wild-K. Treanor-J. Curran-E. (2000) Inflammation-induced upregulation of VR1 in rat spinal cord and DRG correlates with enhanced nociceptive processing. Society for Neuroscience Abstracts 26:1-2: 632.15.

SUMMARY

The present invention comprises a new class of compounds useful in the treatment of diseases, such as vanilloid-receptor-mediated diseases and other maladies, such as inflammatory or neuropathic pain and diseases involving sensory nerve function such as asthma, rheumatoid arthritis, osteoarthritis, inflammatory bowel disorders, urinary incontinence, migraine and psoriasis. In particular, the compounds of the invention are useful for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, anxiety, depression, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders. Accordingly, the invention also comprises pharmaceutical compositions comprising the compounds, methods for the treatment of vanilloid-receptor-mediated diseases, such as inflammatory or neuropathic pain, asthma, rheumatoid arthritis, osteoarthritis, inflammatory bowel disorders, urinary incontinence, migraine and psoriasis diseases, using the compounds and compositions of the invention, and intermediates and processes useful for the preparation of the compounds of the invention.

The compounds of the invention are represented by the following general structure:

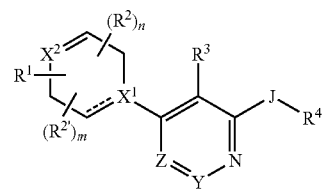

or a pharmaceutically acceptable salt thereof, wherein J, m, n, $R^1$, $R^2$, $R^{2'}$, $R^3$, $R^4$, $X^1$, $X^2$, Y and Z are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION

One aspect of the current invention relates to compounds having the general structure:

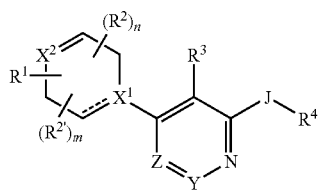

or any pharmaceutically-acceptable salt or hydrate thereof, wherein:

/// represents a single or double bond;
J is NH, O or S;
$X^1$ is N or C;
$X^2$ is N or C;
Y is N or $C(R^{11})$;
Z is N or $C(R^{10})$, wherein no more than one of Y and Z is N;
n 0, 1 or 2;
m is 0 or 1;

wherein
A) when $X^1$ and $X^2$ are both C
$R^1$ is $-OR^a$, $-OR^c$, $-NR^aR^a$, $-NR^aR^c$, $-SR^b$, $-SR^c$, $-S(=O)R^b$, $-S(=O)R^c$, $-S(=O)_2R^b$, $-S(=O)_2R^c$ or $C_{1-6}$alkyl substituted by 0, 1, 2 or 3 substituents independently selected from $C_{1-4}$haloalkyl, halo, cyano, oxo, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^b$, $-OC_{2-6}$alkylNR^aR^a$, $-OC_{2-6}$alkylOR^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}$alkylNR^aR^a$ and $-NR^aC_{2-6}$alkylOR^a$, and additionally substituted by 0 or 1 substituents selected from a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $C_{1-8}$alkyl, $C_{1-4}$haloalkyl, halo, cyano, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^b$, $-OC_{2-6}$alkylNR^aR^a$, $-OC_{2-6}$alkylOR^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}$alkylNR^aR^a$ and $-NR^aC_{2-6}$alkylOR^a$, and the ring is additionally substituted by 0, 1, 2, 3, 4 or 5 substituents selected from Br, Cl, F and I; or $R^1$ is $C_{1-6}$heteroalkyl chain substituted by 0, 1, 2 or 3 substituents independently selected from $C_{1-4}$haloalkyl, halo, cyano, oxo, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^a$, $-OC_{2-6}$alkylNR^aR^a$, $-OC_{2-6}$alkylOR^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}$alkylNR^aR^a$ and $-NR^aC_{2-6}$alkylOR^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^b$, $-OC_{2-6}$alkylNR^aR^a$, $-OC_{2-6}$alkylOR^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}$alkylNR^aR^a$ and $-NR^aC_{2-6}$alkylOR^a$;

B) when at least one of $X^1$ and $X^2$ is N, and J is NH, then
$R^1$ is $C_{1-6}$alkyl substituted by 0, 1, 2 or 3 substituents independently selected from $C_{1-4}$haloalkyl, halo, cyano, oxo, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^b$, $-OC_{2-6}$alkylNR^aR^a$, $-OC_{2-6}$alkylOR^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}$alkylNR^aR^a$ and $-NR^aC_{2-6}$alkylOR^a$, and additionally substituted by a substituent selected from
i) a saturated, partially saturated or unsaturated 5-, 6- or 7-membered monocyclic ring containing 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 1, 2 or 3 substituents selected from $C_{1-8}$alkyl, $C_{1-4}$haloalkyl, halo, cyano, nitro, $-C(=O)R^b$, $-C(=O)OR^b$, $-C(=O)NR^aR^a$, $-C(=NR^a)NR^aR^a$, $-OR^a$, $-OC(=O)R^b$, $-C(=O)NR^aR^a$, $-OC(=O)N(R^a)S(=O)_2R^b$, $-OC_{2-6}$alkylNR^aR^a$, $-OC_{2-6}$alkylOR^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}$alkylNR^aR^a$ and $-NR^aC_{2-6}$alkylOR^a$, and the ring is additionally substituted by 0, 1, 2, 3, 4 or 5 substituents independently selected from Br, Cl, F and I;
ii) a saturated, partially saturated or unsaturated 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1 or 2 substituents selected from $C_{1-8}$alkyl, $C_{1-4}$haloalkyl, halo, cyano, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)

$NR^aR^a$, $-OC(=O)N(R^a)S(=O)_2R^b$, $-OC_{2-6}alkylNR^aR^a$, $-OC_{2-6}alkylOR^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}alkylNR^aR^a$ and $-NR^aC_{2-6}alkylOR^a$, and the ring is additionally substituted by 0, 1, 2, 3, 4 or 5 substituents independently selected from Br, Cl, F and I; and iii) a saturated, partially saturated or unsaturated 6-membered monocyclic carbocyclic ring or a 9-, 10- or 11-membered bicyclic carbocyclic ring substituted by 1, 2 or 3 substituents selected from $C_{1-8}$alkyl, $C_{1-4}$haloalkyl, halo, cyano, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^b$, $-OC_{2-6}alkylNR^aR^a$, $-OC_{2-6}alkylOR^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}alkylNR^aR^a$ and $-NR^aC_{2-6}alkylOR^a$; or $R^1$ is $C_{1-6}$heteroalkyl chain substituted by 0, 1, 2 or 3 substituents independently selected from $C_{1-4}$haloalkyl, halo, cyano, oxo, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^b$, $-OC_{2-6}alkylNR^aR^a$, $-OC_{2-6}alkylOR^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}alkylNR^aR^a$ and $-NR^aC_{2-6}alkylOR^a$, and additionally substituted by a saturated, partially saturated or unsaturated 5-, 6- or 7-membered monocyclic or 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $C_{1-8}$alkyl, $C_{1-4}$haloalkyl, halo, cyano, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^b$, $-OC_{2-6}alkylNR^aR^a$, $-OC_{2-6}alkylOR^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}alkylNR^aR^a$ and $-NR^aC_{2-6}alkylOR^a$, and the ring is additionally substituted by 0, 1, 2, 3, 4 or 5 substituents independently selected from Br, Cl, F and I; or $R^1$ is $C_{1-6}$heteroalkyl chain substituted by 0, 1, 2 or 3 substituents independently selected from $C_{1-4}$haloalkyl, halo, cyano, oxo, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^b$, $-OC_{2-6}alkylNR^aR^a$, $-OC_{2-6}alkylOR^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}alkylNR^aR^a$ and $-NR^aC_{2-6}alkylOR^a$, and additionally substituted by a saturated, partially saturated or unsaturated 5-, 6- or 7-membered monocyclic or 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $C_{1-8}$alkyl, $C_{1-4}$haloalkyl, halo, cyano, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^b$, $-OC_{2-6}alkylNR^aR^a$, $-OC_{2-6}alkylOR^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N(R^a)C(=O)OR^b$, $-S(=O)_2N(R^a)C(=O)NR^aR^a$, $-NR^aR^a$, $-N(R^a)C(=O)R^b$, $-N(R^a)C(=O)OR^b$, $-N(R^a)C(=O)NR^aR^a$, $-N(R^a)C(=NR^a)NR^aR^a$, $-N(R^a)S(=O)_2R^b$, $-N(R^a)S(=O)_2NR^aR^a$, $-NR^aC_{2-6}alkylNR^aR^a$ and $-NR^aC_{2-6}alkylOR^a$, and the ring is additionally substituted by 0, 1, 2, 3, 4 or 5 substituents independently selected from Br, Cl, F and I; or $R^1$ is $-OR^a$, $-OR^c$, $-NR^aR^a$, $-NR^aR^c$, $-SR^b$, $-SR^c$, $-S(=O)R^b$, $-S(=O)R^c$, $-S(=O)_2R^b$ or $-S(=O)_2R^c$, and C) when at least one of $X^1$ and $X^2$ is N, and J is O, then Y and Z are both CH; and $R^1$ is $C_{1-6}$alkyl substituted by 0, 1, 2 or 3 substituents independently selected from $C_{1-4}$haloalkyl, halo, cyano, oxo, nitro, $-C(=O)R^b$, $-C(=O)OR^b$, $-C(=O)NR^aR^a$, $-C(=NR^a)NR^aR^a$, $-OR^a$, $-OC(=O)R^b$, $-C(=O)NR^aR^a$, $-OC(=O)N(R^a)S(=O)_2R^b$, $-OC_{2-6}alkylNR^aR^a$, $-OC_{2-6}alkylOR^a$, $-SR^a$, $-S(=O)R^b$, $-S(=O)_2R^b$, $-S(=O)_2NR^aR^a$, $-S(=O)_2N(R^a)C(=O)R^b$, $-S(=O)_2N$ $R^2$ is, independently, in each instance, $C_{1-6}$alkyl, $C_{1-4}$haloalkyl, F, Cl, or Br;

$R^{2'}$ is $-OR^b$, $-NR^aR^b$, $-SR^b$, $-S(=O)R^b$, $-S(=O)_2R^b$ or $C_{1-6}$alkyl substituted by 0, 1, 2 or 3 substituents independently selected from $C_{1-4}$haloalkyl, halo, cyano, oxo, nitro, $-C(=O)R^b$, $-C(=O)OR^b$, $-C(=O)NR^aR^a$, $-C(=NR^a)NR^aR^a$, $-OR^a$, $-OC(=O)R^b$, $-OC(=O)NR^aR^a$, $-OC(=O)N(R^a)S(=O)_2R^b$, $-OC_{2-6}alkylNR^aR^a$, —OC$_{2-6}$alkylOR$^a$R$^a$, —S(=O)R$^b$, —S(=O)$_2$R$^b$, —S(=O)$_2$ NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by 0 or 1 substituents selected from a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)O R$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{2'}$ is C$_{1-6}$heteroalkyl chain substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^4$ is

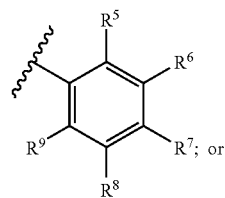

R$^4$ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from R$^e$, C$_{1-4}$haloalkyl, halo, nitro, cyano, oxo, —OR$^f$, —S(=O)$_n$R$^e$, —OC$_{1-4}$haloalkyl, —OC$_{2-6}$alkylNR$^a$R$^f$, —OC$_{2-6}$alkylOR$^f$, —OC$_{1-6}$alkylC(=O)OR$^e$, —NR$^a$R$^f$, —NR$^a$C$_{1-4}$haloalkyl, —NR$^a$C$_{2-6}$alkylNR$^a$R$^f$, —NR$^a$C$_{2-6}$alkylOR$^f$, —C(=O)R$^e$, —C(=O)OR$^e$, —OC(=O)R$^e$, —C(=O)NR$^a$R$^f$ and —NR$^a$C(=O)R$^e$; and unsaturated carbon atoms may be additionally substituted by =O; and any available nitrogen atoms in the heterocycle and bridge are substituted by H, —C$_{1-6}$alkylOR$^f$, —R$^e$, —C$_{1-6}$alkylNR$^a$R$^f$, —C$_{1-3}$alkylC(=O)OR$^e$, —C$_{1-3}$alkylC(=O)NR$^a$R$^f$, —C$_{1-3}$alkylOC(=O)R$^e$, —C$_{1-3}$alkylNR$^a$C(=O)R$^e$, —C(=O)R$^e$ or —C$_{1-3}$alkylR$^e$; or R$^4$ is naphthyl substituted by 1, 2 or 3 substituents independently selected from C$_{1-4}$haloalkyl, halo, nitro, cyano, —S(=O)$_n$R$^e$, —OC$_{1-4}$haloalkyl, —OC$_{2-6}$alkylNR$^a$R$^f$, —OC$_{2-6}$alkylOR$^f$, —OC$_{1-6}$alkylC(=O)OR$^e$, —NR$^a$C$_{1-4}$haloalkyl, —NR$^a$C$_{2-6}$alkylNR$^a$R$^f$, —NR$^a$C$_{2-6}$alkylOR$^f$, —C(=O)R$^e$, —C(=O)OR$^e$, —OC(=O)R$^e$ and —C(=O)NR$^a$R$^f$;

R$^5$ is independently, at each instance, selected from H, C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^5$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^5$ is C$_{1-4}$alkyl substituted by 0, 1, 2 or 3 groups selected from C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^6$ is independently, at each instance, selected from H, C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —$SR^a$, —$S(=O)(R^b)$, —$S(=O)_2(R^b)$, —$S(=O)_2NR^aR^a$, —$S(=O)_2N(R^a)C(=O)(R^b)$, —$S(=O)_2N(R^a)C(=O)O(R^b)$, —$S(=O)_2N(R^a)C(=O)NR^aR^a$, —$NR^aR^a$, —$N(R^a)C(=O)(R^b)$, —$N(R^a)C(=O)O(R^b)$, —$N(R^a)C(=O)NR^aR^a$, —$N(R^a)C(=NR^a)NR^aR^a$, —$N(R^a)S(=O)_2(R^b)$, —$N(R^a)S(=O)_2NR^aR^a$, —$NR^aC_{2-6}alkylNR^aR^a$ and —$NR^aC_{2-6}alkylOR^a$; or $R^6$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —$C(=O)(R^b)$, —$C(=O)O(R^b)$, —$C(=O)NR^aR^a$, —$C(=NR^a)NR^aR^a$, —$OR^a$, —$OC(=O)(R^b)$, —$OC(=O)NR^aR^a$, —$OC(=O)N(R^a)S(=O)_2(R^b)$, —$OC_{2-6}alkylNR^aR^a$, —$OC_{2-6}alkylOR^a$, —$SR^a$, —$S(=O)(R^b)$, —$S(=O)_2(R^b)$, —$S(=O)_2NR^aR^a$, —$S(=O)_2N(R^a)C(=O)(R^b)$, —$S(=O)_2N(R^a)C(=O)O(R^b)$, —$S(=O)_2N(R^a)C(=O)NR^aR^a$, —$NR^aR^a$, —$N(R^a)C(=O)(R^b)$, —$N(R^a)C(=O)O(R^b)$, —$N(R^a)C(=O)NR^aR^a$, —$N(R^a)C(=NR^a)NR^aR^a$, —$N(R^a)S(=O)_2(R^b)$, —$N(R^a)S(=O)_2NR^aR^a$, —$NR^aC_{2-6}alkylNR^aR^a$ and —$NR^aC_{2-6}alkylOR^a$; or $R^5$ and $R^6$ together are a saturated, partially-saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, $R^e$, halo, cyano, nitro, —$C(=O)R^e$, —$C(=O)OR^e$, —$C(=O)NR^fR^f$, —$C(=NR^a)NR^aR^f$, —$OR^f$, —$OC(=O)R^e$, —$OC(=O)NR^fR^f$, —$OC(=O)N(R^f)S(=O)_2R^e$, —$OC_{2-6}alkylNR^aR^f$, —$OC_{2-6}alkylOR^f$, —$SR^f$, —$S(=O)R^e$, —$S(=O)_2R^e$, —$S(=O)_2NR^aR^f$, —$S(=O)_2N(R^f)C(=O)R^e$, —$S(=O)_2N(R^f)C(=O)OR^e$, —$S(=O)_2N(R^f)C(=O)NR^aR^f$, —$NR^aR^f$, —$N(R^f)C(=O)R^e$, —$N(R^f)C(=O)OR^e$, —$N(R^f)C(=O)NR^aR^f$, —$N(R^f)C(=NR^a)NR^aR^f$, —$N(R^f)S(=O)_2R^e$, —$N(R^f)S(=O)_2NR^aR^f$, —$NR^fC_{2-6}alkylNR^aR^f$ and —$NR^fC_{2-6}alkylOR^f$;

$R^7$ is independently, at each instance, selected from H, $C_{1-8}$alkyl, $C_{1-4}$haloalkyl, halo, cyano, nitro, —$C(=O)(R^b)$, —$C(=O)O(R^b)$, —$C(=O)NR^aR^a$, —$C(=NR^a)NR^aR^a$, —$OR^a$ —$OC(=O)(R^b)$, —$OC(=O)NR^aR^a$, —$OC(=O)N(R^a)S(=O)_2(R^b)$, —$OC_{2-6}alkylNR^aR^a$, —$OC_{2-6}alkylOR^a$, —$SR^a$, —$S(=O)(R^b)$, —$S(=O)_2(R^b)$, —$S(=O)_2NR^aR^a$, —$S(=O)_2N(R^a)C(=O)(R^b)$, —$S(=O)_2N(R^a)C(=O)O(R^b)$, —$S(=O)_2N(R^a)C(=O)NR^aR^a$, —$N(R^a)C(=O)(R^b)$, —$N(R^a)C(=O)O(R^b)$, —$N(R^a)C(=O)NR^aR^a$, —$N(R^a)C(=NR^a)NR^aR^a$, —$N(R^a)S(=O)_2(R^b)$, —$N(R^a)S(=O)_2NR^aR^a$, —$NR^aC_{2-6}alkylNR^aR^a$ and —$NR^aC_{2-6}alkylOR^a$; or $R^7$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —$C(=O)(R^b)$, —$C(=O)O(R^b)$, —$C(=O)NR^aR^a$, —$C(=NR^a)NR^aR^a$, —$OR^a$, —$OC(=O)(R^b)$, —$OC(=O)NR^aR^a$, —$OC(=O)N(R^a)S(=O)_2(R^b)$, —$OC_{2-6}alkylNR^aR^a$, —$OC_{2-6}alkylOR^a$, —$SR^a$, —$S(=O)(R^b)$, —$S(=O)_2(R^b)$, —$S(=O)_2NR^aR^a$, —$S(=O)_2N(R^a)C(=O)(R^b)$, —$S(=O)_2N(R^a)C(=O)O(R^b)$, —$S(=O)_2N(R^a)C(=O)NR^aR^a$, —$NR^aR^a$, —$N(R^a)C(=O)(R^b)$, —$N(R^a)C(=O)O(R^b)$, —$N(R^a)C(=O)NR^aR^a$, —$N(R^a)C(=NR^a)NR^aR^a$, —$N(R^a)S(=O)_2(R^b)$, —$N(R^a)S(=O)_2NR^aR^a$, —$NR^aC_{2-6}alkylNR^aR^a$ and —$NR^aC_{2-6}alkylOR^a$; or $R^7$ is $C_{1-4}$alkyl substituted by 0, 1, 2 or 3 groups selected from $C_{1-4}$haloalkyl, halo, cyano, nitro, —$C(=O)(R^b)$, —$C(=O)O(R^b)$, —$C(=O)NR^aR^a$, —$C(=NR^a)NR^aR^a$, —$OR^a$, —$OC(=O)(R^b)$, —$OC(=O)NR^aR^a$, —$OC(=O)N(R^a)S(=O)_2(R^b)$, —$OC_{2-6}alkylNR^aR^a$, —$OC_{2-6}alkylOR^a$, —$SR^a$, —$S(=O)(R^b)$, —$S(=O)_2(R^b)$, —$S(=O)_2NR^aR^a$, —$S(=O)_2N(R^a)C(=O)(R^b)$, —$S(=O)_2N(R^a)C(=O)O(R^b)$, —$S(=O)_2N(R^a)C(=O)NR^aR^a$, —$NR^aR^a$, —$N(R^a)C(=O)(R^b)$, —$N(R^a)C(=O)O(R^b)$, —$N(R^a)C(=O)NR^aR^a$, —$N(R^a)C(=NR^a)NR^aR^a$, —$N(R^a)S(=O)_2(R^b)$, —$N(R^a)S(=O)_2NR^aR^a$, —$NR^aC_{2-6}alkylNR^aR^a$ and —$NR^aC_{2-6}alkylOR^a$; or $R^6$ and $R^7$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 0, 1, 2 or 3 substituents selected from =O, $R^e$, halo, cyano, nitro, —$C(=O)R^e$, —$C(=O)OR^e$, —$C(=O)NR^fR^f$, —$C(=NR^a)NR^aR^f$, —$OR^f$, —$OC(=O)R^e$, —$OC(=O)NR^fR^f$, —$OC(=O)N(R^f)S(=O)_2R^e$, —$OC_{2-6}alkylNR^aR^f$, —$OC_{2-6}alkylOR^f$, —$SR^f$, —$S(=O)R^e$, —$S(=O)_2R^e$, —$S(=O)_2NR^aR^f$, —$S(=O)_2N(R^f)C(=O)R^e$, —$S(=O)_2N(R^f)C(=O)OR^e$, —$S(=O)_2N(R^f)C(=O)NR^aR^f$, —$NR^aR^f$, —$N(R^f)C(=O)R^e$, —$N(R^f)C(=O)OR^e$, —$N(R^f)C(=O)NR^aR^f$, —$N(R^f)C(=NR^a)NR^aR^f$, —$N(R^f)S(=O)_2R^e$, —$N(R^f)S(=O)_2NR^aR^f$, —$NR^fC_{2-6}alkylNR^aR^f$ and —$NR^fC_{2-6}alkylOR^f$;

$R^8$ is independently, at each instance, selected from H, $C_{1-8}$alkyl, $C_{1-4}$haloalkyl, halo, cyano, nitro, —$C(=O)(R^b)$, —$C(=O)O(R^b)$, —$C(=O)NR^aR^a$, —$C(=NR^a)NR^aR^a$, —$OR^a$, —$OC(=O)(R^b)$, —$OC(=O)NR^aR^a$, —$OC(=O)N(R^a)S(=O)_2(R^b)$, —$OC_{2-6}alkylNR^aR^a$, —$OC_{2-6}alkylOR^a$, —$SR^a$, —$S(=O)(R^b)$, —$S(=O)_2(R^b)$, —$S(=O)_2NR^aR^a$, —$S(=O)_2N(R^a)C(=O)(R^b)$, —$S(=O)_2N(R^a)C(=O)O(R^b)$, —$S(=O)_2N(R^a)C(=O)NR^aR^a$, —$NR^aR^a$, —$N(R^a)C(=O)(R^b)$, —$N(R^a)C(=O)O(R^b)$, —$N(R^a)C(=O)NR^aR^a$, —$N(R^a)C(=NR^a)NR^aR^a$, —$N(R^a)S(=O)_2(R^b)$, —$N(R^a)S(=O)_2NR^aR^a$, —$NR^aC_{2-6}alkylNR^aR^a$ and —$NR^aC_{2-6}alkylOR^a$; or $R^8$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —$C(=O)(R^b)$, —$C(=O)O(R^b)$, —$C(=O)NR^aR^a$, —$C(=NR^a)NR^aR^a$, —$OR^a$, —$OC(=O)(R^b)$, —$OC(=O)NR^aR^a$, —$OC(=O)N(R^a)S(=O)_2(R^b)$, —$OC_{2-6}alkylNR^aR^a$, —$OC_{2-6}alkylOR^a$, —$SR^a$, —$S(=O)(R^b)$, —$S(=O)_2(R^b)$, —$S(=O)_2NR^aR^a$, —$S(=O)_2N(R^b)C(=O)(R^b)$, —$S(=O)_2N(R^b)C(=O)O(R^b)$, —$S(=O)_2N(R^a)C(=O)NR^aR^a$, —$NR^aR^a$, —$N(R^a)C(=O)(R^b)$, —$N(R^a)C(=O)O ($R^b$), —N($R^a$)C(=O)N$R^a R^a$, —N($R^a$)C(=N$R^a$)N$R^a R^a$, —N($R^a$)S(=O)$_2$($R^b$), —N($R^a$)S(=O)$_2$N$R^a R^a$, —N$R^a$C$_{2-6}$alkylN$R^a R^a$ and —N$R^a$C$_{2-6}$alkylO$R^a$; or $R^8$ is C$_{1-4}$alkyl substituted by 0, 1, 2 or 3 groups selected from C$_{1-4}$haloalkyl, halo, cyano, nitro, —C(=O)($R^b$), —C(=O)O($R^b$), —C(=O)N$R^a R^a$, —C(=N$R^a$)N$R^a R^a$, —O$R^a$, —OC(=O)($R^b$), —OC(=O)N$R^a R^a$, —OC(=O)N($R^a$)S(=O)$_2$($R^b$), —OC$_{2-6}$alkylN$R^a R^a$, —OC$_{2-6}$alkylO$R^a$, —S$R^a$, —S(=O)($R^b$), —S(=O)$_2$($R^b$), —S(=O)$_2$N$R^a R^a$, —S(=O)$_2$N($R^a$)C(=O)($R^b$), —S(=O)$_2$N($R^a$)C(=O)O($R^b$), —S(=O)$_2$N($R^a$)C(=O)N$R^a R^a$, —N$R^a R^a$, —N($R^a$)C(=O)($R^b$), —N($R^a$)C(=O)O($R^b$), —N($R^a$)C(=O)N$R^a R^a$, —N($R^a$)C(=N$R^a$)N$R^a R^a$, —N($R^a$)S(=O)$_2$($R^b$), —N($R^a$)S(=O)$_2$N$R^a R^a$, —N$R^a$C$_{2-6}$alkylN$R^a R^a$ and —N$R^a$C$_{2-6}$alkylO$R^a$;

$R^9$ is independently, at each instance, selected from H, C$_{1-8}$alkyl, C$_{1-4}$haloalkyl, halo, cyano, nitro, —C(=O)($R^b$), —C(=O)O($R^b$), —C(=O)N$R^a R^a$, —C(=N$R^a$)N$R^a R^a$, —O$R^a$, —OC(=O)($R^b$), —OC(=O)N$R^a R^a$, —OC(=O)N($R^a$)S(=O)$_2$($R^b$), —OC$_{2-6}$alkylN$R^a R^a$, —OC$_{2-6}$alkylO$R^a$, —S$R^a$, —S(=O)($R^b$), —S(=O)$_2$($R^b$), —S(=O)$_2$N$R^a R^a$, —S(=O)$_2$N($R^a$)C(=O)($R^b$), —S(=O)$_2$N($R^a$)C(=O)O($R^b$), —S(=O)$_2$N($R^a$)C(=O)N$R^a R^a$, —N$R^a R^a$, —N($R^a$)C(=O)($R^b$), —N($R^a$)C(=O)O($R^b$), —N($R^a$)C(=O)N$R^a R^a$, —N($R^a$)C(=N$R^a$)N$R^a R^a$, —N($R^a$)S(=O)$_2$($R^b$), —N($R^a$)S(=O)$_2$N$R^a R^a$, —N$R^a$C$_{2-6}$alkylN$R^a R^a$ and —N$R^a$C$_{2-6}$alkylO$R^a$; or $R^9$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)($R^b$), —C(=O)O($R^b$), —C(=O)N$R^a R^a$, —C(=N$R^a$)N$R^a R^a$, —O$R^a$, —OC(=O)($R^b$), —OC(=O)N$R^a R^a$, —OC(=O)N($R^a$)S(=O)$_2$($R^b$), —OC$_{2-6}$alkylN$R^a R^a$, —OC$_{2-6}$alkylO$R^a$, —S$R^a$, —S(=O)($R^b$), —S(=O)$_2$($R^b$), —S(=O)$_2$N$R^a R^a$, —S(=O)$_2$N($R^a$)C(=O)($R^b$), —S(=O)$_2$N($R^a$)C(=O)O($R^b$), —S(=O)$_2$N($R^a$)C(=O)N$R^a R^a$, —N$R^a R^a$, —N($R^a$)C(=O)($R^b$), —N($R^a$)C(=O)O($R^b$), —N($R^a$)C(=O)N$R^a R^a$, —N($R^a$)C(=N$R^a$)N$R^a R^a$, —N($R^a$)S(=O)$_2$($R^b$), —N($R^a$)S(=O)$_2$N$R^a R^a$, —N$R^a$C$_{2-6}$alkylN$R^a R^a$ and —N$R^a$C$_{2-6}$alkylO$R^a$; or $R^9$ is C$_{1-4}$alkyl substituted by 0, 1, 2 or 3 groups selected from C$_{1-4}$haloalkyl, halo, cyano, nitro, —C(=O)($R^b$), —C(=O)O($R^b$), —C(=O)N$R^a R^a$, —C(=N$R^a$)N$R^a R^a$, —O$R^a$, —OC(=O)($R^b$), —OC(=O)N$R^a R^a$, —OC(=O)N($R^a$)S(=O)$_2$($R^b$), —OC$_{2-6}$alkylN$R^a R^a$, —OC$_{2-6}$alkylO$R^a$, —S$R^a$, —S(=O)($R^b$), —S(=O)$_2$($R^b$), —S(=O)$_2$N$R^a R^a$, —S(=O)$_2$N($R^a$)C(=O)($R^b$), —S(=O)$_2$N($R^a$)C(=O)O($R^b$), —S(=O)$_2$N($R^a$)C(=O)N$R^a R^a$, —N$R^a R^a$, —N($R^a$)C(=O)($R^b$), —N($R^a$)C(=O)O($R^b$), —N($R^a$)C(=O)N$R^a R^a$, —N($R^a$)C(=N$R^a$)N$R^a R^a$, —N($R^a$)S(=O)$_2$($R^b$), —N($R^a$)S(=O)$_2$N$R^a R^a$, —N$R^a$C$_{2-6}$alkylN$R^a R^a$ and —N$R^a$C$_{2-6}$alkylO$R^a$; wherein at least one of $R^5$, $R^6$, $R^7$, $R^8$ and $R^9$ is other than H;

$R^{10}$ is (A) C$_{1-8}$alkyl substituted by 0, 1, 2 or 3 substituents independently selected from halo, nitro, cyano, —O$R^m$, —O$R^n$, —OC$_{2-6}$alkylN$R^a R^m$, —OC$_{2-6}$alkylO$R^m$, —N$R^a R^m$, —N$R^a R^n$, —N$R^m$C$_{2-6}$alkylN$R^a R^m$, —N$R^m$C$_{2-6}$alkylO$R^m$, —CO$_2 R^k$, —C(=O)$R^k$, —C(=O)N$R^a R^m$, —C(=O)N$R^a R^n$, —N$R^m$C(=O)$R^k$, —N$R^m$C(=O)$R^n$, —N$R^m$C(=O)N$R^a R^m$, —N$R^m$CO$_2 R^k$, —C$_{1-8}$alkylO$R^m$, —C$_{1-6}$alkylN$R^a R^m$, —S(=O)$_n R^k$, —S(=O)$_2$N$R^a R^m$, —N$R^a$S(=O)$_2 R^k$ and —OC(=O)N$R^a R^m$, and additionally substituted by 0, 1 or 2$R^i$ groups, and additionally substituted by 0, 1, 2, 3, 4 or 5 substituents independently selected from Br, Cl, F and I; or (B) a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 0, 1, 2 or 3 substituents independently selected from $R^k$, $R^h$, halo, nitro, cyano, —O$R^k$, —O$R^n$, —OC$_{2-6}$alkylN$R^a R^m$, —OC$_{2-6}$alkylO$R^m$, —N$R^a R^m$, —N$R^a R^n$, —N$R^m$C$_{2-6}$alkylN$R^a R^m$, —N$R^m$C$_{2-6}$alkylO$R^m$, naphthyl, —CO$_2 R^k$, —C(=O)$R^k$, —C(=O)N$R^a R^m$, —C(=O)N$R^a R^n$, —N$R^m$C(=O)$R^k$, —N$R^m$C(=O)$R^n$, —N$R^m$C(=O)N$R^a R^m$, —N$R^m$CO$_2 R^k$, —C$_{1-8}$alkylO$R^m$, —C$_{1-6}$alkylN$R^a R^m$, —S(=O)$_n R^k$, —S(=O)$_2$N$R^a R^m$, —N$R^a$S(=O)$_2 R^k$ and —OC(=O)N$R^a R^m$, and the ring is additionally substituted by 0, 1, 2, 3, 4 or 5 substituents independently selected from Br, Cl, F and I; or (C) —N($R^a$)—C$_{1-8}$alkyl, wherein the C$_{1-8}$alkyl is substituted by 0, 1, 2 or 3 substituents independently selected from $R^h$, halo, nitro, cyano, —O$R^k$, —O$R^n$, —OC$_{2-6}$alkylN$R^a R^m$, —OC$_{2-6}$alkylO$R^m$, —N$R^a R^m$, —N$R^a R^n$, —N$R^m$C$_{2-6}$alkylN$R^a R^m$, —N$R^m$C$_{2-6}$alkylO$R^m$, naphthyl, —CO$_2 R^k$, —C(=O)$R^k$, —C(=O)N$R^a R^m$, —C(=O)N$R^a R^n$, —N$R^m$C(=O)$R^k$, —N$R^m$C(=O)$R^n$, —N$R^m$C(=O)N$R^a R^m$, —N$R^m$CO$_2 R^k$, —C$_{1-8}$alkylO$R^m$, —C$_{1-6}$alkylN$R^a R^m$, —S(=O)$_n R^k$, —S(=O)$_2$N$R^a R^m$, —N$R^a$S(=O)$_2 R^k$ and —OC(=O)N$R^a R^m$, and additionally substituted by 0, 1, 2, 3, 4 or 5 substituents independently selected from Br, Cl, F and I; or (D) —OC$_{1-8}$alkyl, wherein the C$_{1-8}$alkyl is substituted by 0, 1, 2 or 3 substituents independently selected from $R^k$, $R^h$, halo, nitro, cyano, —O$R^k$, —OC$_{2-6}$alkylN$R^a R^m$, —OC$_{2-6}$alkylO$R^m$, —N$R^a R^m$, —N$R^a R^n$, —N$R^m$C$_{2-6}$alkylN$R^a R^m$, —N$R^m$C$_{2-6}$alkylO$R^m$, naphthyl, —CO$_2 R^k$, —C(=O)$R^k$, —C(=O)N$R^a R^m$, —C(=O)N$R^a R^n$, —N$R^m$C(=O)$R^k$, —N$R^m$C(=O)$R^n$, —N$R^m$C(=O)N$R^a R^m$, —N$R^m$CO$_2 R^k$, —C$_{1-8}$alkylO$R^m$, —C$_{1-6}$alkylN$R^a R^m$, —S(=O)$_n R^k$, —S(=O)$_2$N$R^a R^m$, —N$R^a$S(=O)$_2 R^k$ and —OC(=O)N$R^a R^m$, and additionally substituted by 0, 1, 2, 3, 4 or 5 substituents independently selected from Br, Cl, F and I; or (E) H, cyano, —O$R^i$, —S$R^i$, —N($R^a$)$R^i$, —OH or —NH$_2$;

$R^{11}$ is (A) C$_{1-8}$alkyl substituted by 0, 1, 2 or 3 substituents independently selected from halo, nitro, cyano, —O$R^m$, —O$R^n$, —OC$_{2-6}$alkylN$R^a R^m$, —OC$_{2-6}$alkylO$R^m$, —N$R^a R^m$, —N$R^a R^n$, —N$R^m$C$_{2-6}$alkylN$R^a R^m$, —N$R^m$C$_{2-6}$alkylO$R^m$, —CO$_2 R^k$, —C(=O)$R^k$, —C(=O)N$R^a R^m$, —C(=O)N$R^a R^n$, —N$R^m$C(=O)$R^k$, —N$R^m$C(=O)$R^n$, —N$R^m$C(=O)N$R^a R^m$, —N$R^m$CO$_2 R^k$, —C$_{1-8}$alkylO$R^m$, —C$_{1-6}$alkylN$R^a R^m$, —S(=O)$_n R^k$, —S(=O)$_2$N$R^a R^m$, —N$R^a$S(=O)$_2 R^k$ and —OC(=O)N$R^a R^m$, and additionally substituted by 0, 1 or 2$R^i$ groups, and additionally substituted by 0, 1, 2, 3, 4 or 5 substituents independently selected from Br, Cl, F and I; or (B) a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 0, 1, 2 or 3 substituents independently selected from $R^k$, $R^h$, halo, nitro, cyano, —$OR^k$, —$OR^n$, —$OC_{2-6}$alkylN$R^aR^m$, —$OC_{2-6}$alkylO$R^m$, —$NR^aR^m$, —$NR^aR^n$, —$NR^mC_{2-6}$alkylN$R^aR^m$, —$NR^mC_{2-6}$alkylO$R^m$, naphthyl, —$CO_2R^k$, —$C(=O)R^k$, —$C(=O)NR^aR^m$, —$C(=O)NR^aR^n$, —$NR^mC(=O)R^k$, —$NR^mC(=O)R^n$, —$NR^mC(=O)NR^aR^m$, —$NR^mCO_2R^k$, —$C_{1-8}$alkylO$R^m$, —$C_{1-6}$alkylN$R^aR^m$, —$S(=O)_nR^k$, —$S(=O)_2NR^aR^m$, —$NR^aS(=O)_2R^k$ and —$OC(=O)NR^aR^m$, and the ring is additionally substituted by 0, 1, 2, 3, 4 or 5 substituents independently selected from Br, Cl, F and I; or (C) —N($R^a$)—$C_{1-8}$alkyl, wherein the $C_{1-8}$alkyl is substituted by 0, 1, 2 or 3 substituents independently selected from $R^h$, halo, nitro, cyano, —$OR^k$, —$OR^n$, —$OC_{2-6}$alkylN$R^aR^m$, —$OC_{2-6}$alkylO$R^m$, —$NR^aR^m$, —$NR^aR^n$, —$NR^mC_{2-6}$alkylN$R^aR^m$—$NR^mC_{2-6}$alkylO$R^m$, naphthyl, —$CO_2R^k$, —$C(=O)R^k$, —$C(=O)NR^aR^m$, —$C(=O)NR^aR^n$, $NR^mC(=O)R^k$, —$NR^mC(=O)R^n$, —$NR^mC(=O)NR^aR^m$, —$NR^mCO_2R^k$, —$C_{1-8}$alkylO$R^m$, —$C_{1-6}$alkylN$R^aR^m$, —$S(=O)_nR^k$, —$S(=O)_2NR^aR^m$, —$NR^aS(=O)_2R^k$ and —$OC(=O)NR^aR^m$, and additionally substituted by 0, 1, 2, 3, 4 or 5 substituents independently selected from Br, Cl, F and I; or (D) —$OC_{1-8}$alkyl, wherein the $C_{1-8}$alkyl is substituted by 0, 1, 2 or 3 substituents independently selected from $R^k$, $R^h$, halo, nitro, cyano, —$OR^k$, —$OC_{2-6}$alkylN$R^aR^m$, —$OC_{2-6}$alkylO$R^m$, —$NR^aR^m$, —$NR^aR^m$n, —$NR^mC_{2-6}$alkylN$R^aR^m$, —$NR^mC_{2-6}$alkylO$R^m$, naphthyl, —$CO_2R^k$, —$C(=O)R^k$, —$C(=O)NR^aR^m$, —$C(=O)NR^aR^n$, $NR^mC(=O)R^k$, —$NR^mC(=O)R^n$, —$NR^mC(=O)NR^aR^m$, —$NR^mCO_2R^k$, —$C_{1-8}$alkylO$R^m$, $C_{1-6}$alkylN$R^aR^m$, —$S(=O)_nR^k$, —$S(=O)_2NR^aR^m$, —$NR^aS(=O)_2R^k$ and —$OC(=O)NR^aR^m$, and additionally substituted by 0, 1, 2, 3, 4 or 5 substituents independently selected from Br, Cl, F and I; or (E) H, cyano, —$OR^i$, —$SR^i$, —N($R^a$)$R^i$, —OH or —$NH_2$;

$R^a$ is independently, at each instance, H or $R^b$;

$R^b$ is independently, at each instance, phenyl, benzyl or $C_{1-6}$alkyl, the phenyl, benzyl and $C_{1-6}$alkyl being substituted by 0, 1, 2 or 3 substituents selected from halo, $C_{1-4}$alkyl, $C_{1-3}$haloalkyl, —$OC_{1-4}$alkyl, OH, —$NH_2$, —$NHC_{1-4}$alkyl, —N($C_{1-4}$alkyl)$C_{1-4}$alkyl;

$R^c$ is independently, in each instance, phenyl substituted by 0, 1 or 2 groups selected from halo, $C_{1-4}$alkyl, $C_{1-3}$haloalkyl, —$OR^a$ and —$NR^aR^a$; or $R^c$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo groups, wherein the heterocycle or fused phenyl ring is substituted by 0, 1, 2 or 3 substituents selected from halo, $C_{1-4}$alkyl, $C_{1-3}$haloalkyl, —$OR^a$ and —$NR^aR^a$;

$R^e$ is, independently, in each instance, $C_{1-9}$alkyl substituted by 0, 1, 2, 3 or 4 substituents selected from halo, cyano, nitro, —$C(=O)R^b$, —$C(=O)OR^b$, $C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}$alkylN$R^aR^a$, —$OC_{2-6}$alkylO$R^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkylN$R^aR^a$ and —$NR^aC_{2-6}$alkylO$R^a$; and wherein the $C_{1-9}$alkyl is additionally substituted by 0 or 1 groups independently selected from $R^g$;

$R^f$ is, independently, in each instance, $R^e$ or H;

$R^g$ is, independently, in each instance, a saturated or unsaturated 5- or 6-membered monocyclic ring containing 1, 2 or 3 atoms selected from N, O and S, so long as the combination of O and S atoms is not greater than 2, wherein the carbon atoms of the ring are substituted by 0 or 1 oxo groups;

$R^h$ is, independently, in each instance, phenyl or a saturated, partially saturated or unsaturated 5- or 6-membered monocyclic ring containing 1, 2 or 3 atoms selected from N, O and S, so long as the combination of O and S atoms is not greater than 2, wherein the ring is substituted by 0 or 1 oxo or thioxo groups, wherein the phenyl or monocycle are substituted by 0, 1, 2 or 3 substituents selected from halo, cyano, nitro, —$C(=O)R^e$, —$C(=O)OR^e$, —$C(=O)NR^aR^f$, —$C(=NR^a)NR^aR^f$, —$OR^f$, —$OC(=O)R^e$, —$OC(=O)NR^aR^f$, —$OC(=O)N(R^a)S(=O)_2R^e$, —$OC_{2-6}$alkylN$R^aR^f$, —$OC_{2-6}$alkylO$R^f$, —$SR^f$, —$S(=O)R^e$, —$S(=O)_2R^e$, —$S(=O)_2NR^aR^f$, —$S(=O)_2N(R^a)C(=O)R^e$, —$S(=O)_2N(R^a)C(=O)OR^e$, —$S(=O)_2N(R^a)C(=O)NR^aR^f$, —$NR^aR^f$, —$N(R^a)C(=O)R^e$, —$N(R^a)C(=O)OR^e$, —$N(R^a)C(=O)NR^aR^f$, —$N(R^a)C(=NR^a)NR^aR^f$, —$N(R^a)S(=O)_2R^e$, —$N(R^a)S(=O)_2NR^aR^f$, —$NR^aC_{2-6}$alkylN$R^aR^a$ and —$NR^aC_{2-6}$alkylO$R^f$;

$R^i$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 0, 1, 2 or 3 substituents independently selected from $R^f$, $R^g$, $R^c$, halo, nitro, cyano, —$OR^e$, $OR^g$, —$OC_{2-6}$alkylN$R^aR^f$, —$OC_{2-6}$alkylO$R^f$, —$NR^aR^f$, —$NR^aR^g$, —$NR^jC_{2-6}$alkylN$R^aR^f$, —$NR^jC_{2-6}$alkylO$R^f$, naphthyl, —$CO_2R^e$, —$C(=O)R^e$, —$C(=O)NR^aR^e$, —$C(=O)NR^aR^g$, —$NR^jC(=O)R^e$, —$NR^jC(=O)R^g$, —$NR^jC(=O)NR^aR^f$, —$NR^jCO_2R^e$, —$C_{1-8}$alkylO$R^f$, —$C_{1-6}$alkylN$R^aR^f$, —$S(=O)_nR^e$, —$S(=O)_2NR^aR^f$, —$NR^aS(=O)_2R^e$ and —$OC(=O)NR^aR^f$, and the ring is additionally substituted by 0, 1, 2, 3, 4 or 5 substituents independently selected from Br, Cl, F and I;

$R^k$ is, independently, in each instance, $C_{1-9}$alkyl or $C_{1-4}$alkyl(phenyl) wherein either is substituted by 0, 1, 2, 3 or 4 substituents selected from halo, $C_{1-4}$haloalkyl, cyano, nitro, —$C(=O)R^a$, —$C(=O)OR^a$, —$C(=O)NR^aR^a$, —$C(=NR^a)NR^aR^a$, —$OR^a$, —$OC(=O)R^a$, —$OC(=O)NR^aR^a$, —$OC(=O)N(R^a)S(=O)_2R^a$, —$OC_{2-6}$alkylN$R^aR^a$, —$OC_{2-6}$alkylO$R^a$, —$SR^a$, —$S(=O)R^a$, —$S(=O)_2R^a$, —$S(=O)_2NR^aR^a$, —$S(=O)_2N(R^a)C(=O)R^a$, —$S(=O)_2N(R^a)C(=O)OR^a$, —$S(=O)_2N(R^a)C(=O)NR^aR^a$, —$NR^aR^a$, —$N(R^a)C(=O)R^a$, —$N(R^a)C(=O)OR^a$, —$N(R^a)C(=O)NR^aR^a$, —$N(R^a)C(=NR^a)NR^aR^a$, —$N(R^a)S(=O)_2R^a$, —$N(R^a)S(=O)_2NR^aR^a$, —$NR^aC_{2-6}$alkylN$R^aR^a$ and —$NR^aC_{2-6}$alkylO$R^a$; and wherein the $C_{1-9}$alkyl is additionally substituted by 0 or 1 groups independently selected from $R^h$ and additionally substituted by 0, 1, 2, 3, 4 or 5 substituents independently selected from Br, Cl, F and I;

$R^m$ is, independently, in each instance, $R^e$ or H; and $R^n$ is, independently, in each instance, a saturated, partially saturated or unsaturated 5- or 6-membered monocyclic ring containing 1, 2 or 3 atoms selected from N, O and S, so long as the combination of O and S atoms is not greater than 2, wherein the ring is substituted by 0 or 1 oxo or thioxo groups.

Another aspect of the current invention relates to compounds having the general structure:

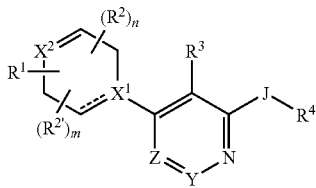

or any pharmaceutically-acceptable salt thereof, wherein:

represents a single or double bond;
 J is NH, O or S;
 $X^1$ is N or C;
 $X^2$ is N or C;
 Y is N or $C(R^{11})$;
 Z is N or $C(R^{10})$, wherein no more than one of Y and Z is N;
 n 0, 1 or 2;
 m is 0 or 1;

wherein
 A) when $X^1$ and $X^2$ are both C
 $R^1$ is —$OR^b$, —$NR^aR^b$, —$SR^b$, —$S(=O)R^b$, —$S(=O)_2R^b$ or $C_{1-6}$alkyl substituted by 0, 1, 2 or 3 substituents independently selected from $C_{1-4}$haloalkyl, halo, cyano, oxo, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}$alkylNR$^a$R$^a$, —$OC_{2-6}$alkylOR$^a$, —$SR^a$—$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkylNR$^a$R$^a$ and —$NR^aC_{2-6}$alkylOR$^a$, and additionally substituted by 0 or 1 substituents selected from a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 1, 2 or 3 substituents selected from $C_{1-8}$alkyl, $C_{1-4}$haloalkyl, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}$alkylNR$^a$R$^a$, —$OC_{2-6}$alkylOR$^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkylNR$^a$R$^a$ and —$NR^aC_{2-6}$alkylOR$^a$; or $R^1$ is $C_{1-6}$heteroalkyl chain substituted by 0, 1, 2 or 3 substituents independently selected from $C_{1-4}$haloalkyl, halo, cyano, oxo, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}$alkylNR$^a$R$^a$, —$OC_{2-6}$alkylOR$^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkylNR$^a$R$^a$ and —$NR^aC_{2-6}$alkylOR$^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}$alkylNR$^a$R$^a$, —$OC_{2-6}$alkylOR$^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkylNR$^a$R$^a$ and —$NR^aC_{2-6}$alkylOR$^a$;

B) when at least one of $X^1$ and $X^2$ is N, and J is NH, then
 $R^1$ is $C_{1-6}$alkyl substituted by 0, 1, 2 or 3 substituents independently selected from $C_{1-4}$haloalkyl, halo, cyano, oxo, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}$alkylOR$^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkylNR$^a$R$^a$ and —$NR^aC_{2-6}$alkylOR$^a$, and additionally substituted by a substituent selected from
 i) a saturated, partially saturated or unsaturated 5-, 6- or 7-membered ring containing 1, 2, 3 or 4 atoms selected from N, O and S, wherein the carbon atoms of the ring are substituted by 0, 1 or 2 oxo groups and the ring is substituted by 1, 2 or 3 substituents selected from $C_{1-8}$alkyl, $C_{1-4}$haloalkyl, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}$alkylNR$^a$R$^a$, —$OC_{2-6}$alkylOR$^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkylNR$^a$R$^a$ and —$NR^aC_{2-6}$alkylOR$^a$; and
 ii) phenyl substituted by 0, 1, 2 or 3 substituents from $C_{1-8}$alkyl, $C_{1-4}$haloalkyl, halo, cyano, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}$alkylNR$^a$R$^a$, —$OC_{2-6}$alkylOR$^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkylNR$^a$R$^a$ and —$NR^aC_{2-6}$alkylOR$^a$; or
 $R^1$ is $C_{1-6}$heteroalkyl chain substituted by 0, 1, 2 or 3 substituents independently selected from $C_{1-4}$haloalkyl, halo, cyano, oxo, nitro, —$C(=O)R^b$, —$C(=O)OR^b$, —$C(=O)NR^aR^a$, —$C(=NR^a)NR^aR^a$, —$OR^a$, —$OC(=O)R^b$, —$OC(=O)NR^aR^a$, —$OC(=O)N(R^a)S(=O)_2R^b$, —$OC_{2-6}$alkylNR$^a$R$^a$, —$OC_{2-6}$alkylOR$^a$, —$SR^a$, —$S(=O)R^b$, —$S(=O)_2R^b$, —$S(=O)_2NR^aR^a$, —$S(=O)_2N(R^a)C(=O)R^b$, —$S(=O)_2N(R^a)C(=O)OR^b$, —$S(=O)_2N(R^a)C(=O)NR^aR^a$, —$NR^aR^a$, —$N(R^a)C(=O)R^b$, —$N(R^a)C(=O)OR^b$, —$N(R^a)C(=O)NR^aR^a$, —$N(R^a)C(=NR^a)NR^aR^a$, —$N(R^a)S(=O)_2R^b$, —$N(R^a)S(=O)_2NR^aR^a$, —$NR^aC_{2-6}$alkylN- $R^aR^a$ and —$NR^aC_{2-6}$alkylOR$^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and C) when at least one of $X^1$ and $X^2$ is N, and J is O, then Y and Z are both CH; and $R^1$ is $C_{1-6}$alkyl substituted by 0, 1, 2 or 3 substituents independently selected from $C_{1-4}$haloalkyl, halo, cyano, oxo, nitro, —C(=O)R$^b$, —C(O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; or $R^1$ is $C_{1-6}$heteroalkyl chain substituted by 0, 1, 2 or 3 substituents independently selected from $C_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

$R^2$ is, independently, in each instance, $C_{1-6}$alkyl, $C_{1-4}$haloalkyl, F, Cl, or Br;

$R^{2'}$ is —OR$^b$, —NR$^a$R$^b$, —SR$^b$, —S(=O)R$^b$, —S(=O)$_2$R$^b$ or $C_{1-6}$alkyl substituted by 0, 1, 2 or 3 substituents independently selected from $C_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by 0 or 1 substituents selected from a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 1, 2 or 3 substituents selected from $C_{1-8}$alkyl, $C_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; or $R^{2'}$ is $C_{1-6}$heteroalkyl chain substituted by 0, 1, 2 or 3 substituents independently selected from $C_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)R$^b$, —C(=O)OR$^b$, —OC(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$;

$R^3$ is H or methyl;

R⁴ is

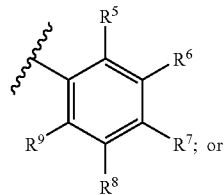

R⁴ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from $R^e$, $C_{1-4}$haloalkyl, halo, nitro, cyano, oxo, —$OR^f$, —S(=O)$_n$$R^e$, —O$C_{1-4}$haloalkyl, —O$C_{2-6}$alkylNR$^a$R$^f$, —O$C_{2-6}$alkylOR$^f$, —O$C_{1-6}$alkylC(=O)OR$^c$, —NR$^a$R$^f$, —NR$^a$$C_{1-4}$haloalkyl, —NR$^a$$C_{2-6}$alkylNR$^a$R$^f$, —NR$^a$$C_{2-6}$alkylOR$^f$, —C(=O)R$^e$, —C(=O)OR$^e$, —OC(=O)R$^e$, —C(=O)NR$^a$R$^f$ and —NR$^a$C(=O)R$^e$; and unsaturated carbon atoms may be additionally substituted by =O; and any available nitrogen atoms in the heterocycle and bridge are substituted by H, —$C_{1-6}$alkylOR$^f$, R$^e$, —$C_{1-6}$alkylNR$^a$R$^f$, —$C_{1-3}$alkylC(=O)OR$^e$, —$C_{1-3}$alkylC(=O)NR$^a$R$^f$, —$C_{1-3}$alkylOC(=O)R$^e$, —$C_{1-3}$alkylNR$^a$C(=O)R$^e$, —C(=O)R$^c$ or —$C_{1-3}$alkylR$^c$; or R⁴ is naphthyl substituted by 1, 2 or 3 substituents independently selected from $C_{1-4}$haloalkyl, halo, nitro, cyano, —S(=O)R$^e$, —O$C_{1-4}$haloalkyl, —O$C_{2-6}$alkylNR$^a$R$^f$, —O$C_{2-6}$alkylOR$^f$, —O$C_{1-6}$alkylC(=O)OR$^e$, —NR$^a$$C_{1-4}$haloalkyl, —NR$^a$$C_{2-6}$alkylNR$^a$R$^f$, —NR$^a$$C_{2-6}$alkylOR$^f$, —C(=O)R$^e$, —C(=O)OR$^e$, —OC(=O)R$^e$ and —C(=O)NR$^a$R$^f$;

R⁵ is independently, at each instance, selected from H, $C_{1-8}$alkyl, $C_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —O$C_{2-6}$alkylNR$^a$R$^a$, —O$C_{2-6}$alkylOR$^a$SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$$C_{2-6}$alkylNR$^a$ and —NR$^a$$C_{2-6}$alkylOR$^a$; or R⁵ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O) NR$^a$R$^a$, —OC(=O)N(R$^a$)S(=O)$_2$(R$^b$), —O$C_{2-6}$alkylNR$^a$R$^a$, —O$C_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$$C_{2-6}$alkylNR$^a$ and —NR$^a$$C_{2-6}$alkylOR$^a$; or R⁵ is $C_{1-4}$alkyl substituted by 0, 1, 2 or 3 groups selected from $C_{1-4}$haloalkyl, halo, cyano, nitro, —C(=O)(R$^b$), —C(=O)O(R$^b$), —C(=O) NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —O$C_{2-6}$alkylNR$^a$R$^a$, —O$C_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O) (R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$$C_{2-6}$alkylNR$^a$ and —NR$^a$$C_{2-6}$alkylOR$^a$;

R⁶ is independently, at each instance, selected from H, $C_{1-8}$alkyl, $C_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N (R$^a$)S(=O)$_2$(R$^b$), —O$C_{2-6}$alkylNR$^a$R$^a$, —O$C_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)S(=O)$_2$(R$^b$), —N(R$^a$)S(=O)$_2$NR$^a$R$^a$, —NR$^a$$C_{2-6}$alkylNR$^a$R$^a$ and —NR$^a$$C_{2-6}$alkylOR$^a$; or R⁶ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O) NR$^a$R$^a$, —OC(=O)N(R$^a$)S(=O)$_2$(R$^b$), —O$C_{2-6}$alkylNR$^a$R$^a$, —O$C_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O) NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$$C_{2-6}$alkylNR$^a$R$^a$ and —NR$^a$$C_{2-6}$alkylOR$^a$; or R⁶ is $C_{1-4}$alkyl substituted by 0, 1, 2 or 3 groups selected from $C_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O) (R$^b$), —OC(=O)NR$^a$R$^a$, —OC(=O)N(R$^a$)S(=O)$_2$(R$^b$), —O$C_{2-6}$alkylNR$^a$R$^a$, —O$C_{2-6}$alkylOR$^a$, —SR$^a$, —S(=O) (R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$$C_{2-6}$alkylNR$^a$R$^a$ and —NR$^a$$C_{2-6}$alkylOR$^a$; or R⁵ and R⁶ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 0, 1, 2 or 3 substituents selected from =O, R$^e$, halo, cyano, nitro, —C(=O)R$^e$, —C(=O)OR$^e$, —C(=O) NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —O$C_{2-6}$alkylNR$^a$R$^f$, —O$C_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)

$NR^aR^f$, $-N(R^f)C(=NR^a)NR^aR^f$, $-N(R^f)S(=O)_2R^e$, $-N(R^f)S(=O)_2NR^aR^f$, $-NR^fC_{2-6}alkylNR^aR^f$ and $-NR^fC_{2-6}alkylOR^f$;

$R^7$ is independently, at each instance, selected from H, $C_{1-8}$alkyl, $C_{1-4}$haloalkyl, halo, cyano, nitro, $-C(=O)(R^b)$, $-C(=O)O(R^b)$, $-C(=O)NR^aR^a$, $-C(=NR^a)NR^aR^a$, $-OR^a$, $-OC(=O)(R^b)$, $-C(=O)NR^aR^a$, $-OC(=O)N(R^a)S(=O)_2(R^b)$, $-OC_{2-6}alkylNR^aR^a$, $-OC_{2-6}alkylOR^a$, $-SR^a$, $-S(=O)(R^b)$, $-S(=O)_2(R^b)$, $-S(=O)_2NR^aR^a$, $-S(=O)_2N(R^a)C(=O)(R^b)$, $-S(=O)_2N(R^a)C(=O)O(R^b)$, $-S(=O)_2N(R^a)C(=O)NR^aR^a$, $-N(R^a)C(=O)(R^b)$, $-N(R^a)C(=O)O(R^b)$, $-N(R^a)C(=O)NR^aR^a$, $-N(R^a)C(=NR^a)NR^aR^a$, $-N(R^a)S(=O)_2(R^b)$, $-N(R^a)S(=O)_2NR^aR^a$, $-NR^aC_{2-6}alkylNR^aR^a$ and $-NR^aC_{2-6}alkylOR^a$; or $R^7$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, $-C(=O)(R^b)$, $-C(=O)O(R^b)$, $-C(=O)NR^aR^a$, $-C(=NR^a)NR^aR^a$, $-OR^a$, $-OC(=O)(R^b)$, $-OC(=O)NR^aR^a$, $-OC(=O)N(R^a)S(=O)_2(R^b)$, $-OC_{2-6}alkylNR^aR^a$, $-OC_{2-6}alkylOR^a$, $-SR^a$, $-S(=O)(R^b)$, $-S(=O)_2(R^b)$, $-S(=O)_2NR^aR^a$, $-S(=O)_2N(R^a)C(=O)(R^b)$, $-S(=O)_2N(R^a)C(=O)O(R^b)$, $-S(=O)_2N(R^a)C(=O)NR^aR^a$, $-NR^aR^a$, $-N(R^a)C(=O)(R^b)$, $-N(R^a)C(=O)O(R^b)$, $-N(R^a)C(=O)NR^aR^a$, $-N(R^a)C(=NR^a)NR^aR^a$, $-N(R^a)S(=O)_2(R^b)$, $-N(R^a)S(=O)_2NR^aR^a$, $-NR^aC_{2-6}alkylNR^aR^a$ and $-NR^aC_{2-6}alkylOR^a$; or $R^7$ is $C_{1-4}$alkyl substituted by 0, 1, 2 or 3 groups selected from $C_{1-4}$haloalkyl, halo, cyano, nitro, $-C(=O)(R^b)$, $-C(=O)O(R^b)$, $-C(=O)NR^aR^a$, $-C(=NR^a)NR^aR^a$, $-OR^a$, $-OC(=O)(R^b)$, $-OC(=O)NR^aR^a$, $-OC(=O)N(R^a)S(=O)_2(R^b)$, $-OC_{2-6}alkylNR^aR^a$, $-OC_{2-6}alkylOR^a$, $-SR^a$, $-S(=O)(R^b)$, $-S(=O)_2(R^b)$, $-S(=O)_2NR^aR^a$, $-S(=O)_2N(R^a)C(=O)(R^b)$, $-S(=O)_2N(R^a)C(=O)O(R^b)$, $-S(=O)_2N(R^a)C(=O)NR^aR^a$, $-NR^aR^a$, $-N(R^a)C(=O)(R^b)$, $-N(R^a)C(=O)O(R^b)$, $-N(R^a)C(=O)NR^aR^a$, $-N(R^a)C(=NR^a)NR^aR^a$, $-N(R^a)S(=O)_2(R^b)$, $-N(R^a)S(=O)_2NR^aR^a$, $-NR^aC_{2-6}alkylNR^aR^a$ and $-NR^aC_{2-6}alkylOR^a$; or $R^6$ and $R^7$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 0, 1, 2 or 3 substituents selected from =O, $R^e$, halo, cyano, nitro, $-C(=O)R^e$, $-C(=O)OR^e$, $-C(=O)NR^aR^f$, $-C(=NR^a)NR^aR^f$, $-OR^f$, $-OC(=O)R^e$, $-C(=O)NR^aR^f$, $OC(=O)N(R^f)S(=O)_2R^e$, $-OC_{2-6}alkylNR^aR^f$, $-OC_{2-6}alkylOR^f$, $-SR^f$, $-S(=O)R^e$, $-S(=O)_2R^e$, $-S(=O)_2NR^aR^f$, $-S(=O)_2N(R^f)C(=O)R^e$, $-S(=O)_2 N(R^f)C(=O)OR^e$, $-S(=O)_2N(R^f)C(=O)NR^aR^f$, $-NR^aR^f$, $-N(R^f)C(=O)R^e$, $-N(R^f)C(=O)OR^e$, $-N(R^f)C(=O)NR^aR^f$, $-N(R^f)C(=NR^a)NR^aR^f$, $-N(R^f)S(=O)_2 R^e$, $-N(R^f)S(=O)_2NR^aR^f$, $-NR^fC_{2-6}alkylNR^aR^f$ and $-NR^fC_{2-6}alkylOR^f$;

$R^8$ is independently, at each instance, selected from H, $C_{1-8}$alkyl, $C_{1-4}$haloalkyl, halo, cyano, nitro, $-C(=O)(R^b)$, $-C(=O)O(R^b)$, $-C(=O)NR^aR^a$, $-C(=NR^a)NR^aR^a$, $-OR^a$, $-OC(=O)(R^b)$, $-C(=O)NR^aR^a$, $-OC(=O)N(R^a)S(=O)_2(R^b)$, $-OC_{2-6}alkylNR^aR^a$, $-OC_{2-6}alkylOR^a$, $-SR^a$, $-S(=O)(R^b)$, $-S(=O)_2(R^b)$, $-S(=O)_2NR^aR^a$, $-S(=O)_2N(R^a)C(=O)(R^b)$, $-S(=O)_2N(R^a)C(=O)O(R^b)$, $-S(=O)_2N(R^a)C(=O)NR^aR^a$, $-N(R^a)C(=O)(R^b)$, $-N(R^a)C(=O)O(R^b)$, $-N(R^a)C(=O)NR^aR^a$, $-N(R^a)C(=NR^a)NR^aR^a$, $-N(R^a)S(=O)_2(R^b)$, $-N(R^a)S(=O)_2NR^aR^a$, $-NR^aC_{2-6}alkylNR^aR^a$ and $-NR^aC_{2-6}alkylOR^a$; or $R^8$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, $-C(=O)(R^b)$, $-C(=O)O(R^b)$, $-C(=O)NR^aR^a$, $-C(=NR^a)NR^aR^a$, $-OR^a$, $-OC(=O)(R^b)$, $-OC(=O)NR^aR^a$, $-OC(=O)N(R^a)S(=O)_2(R^b)$, $-OC_{2-6}alkylNR^aR^a$, $-OC_{2-6}alkylOR^a$, $-SR^a$, $-S(=O)(R^b)$, $-S(=O)_2(R^b)$, $-S(=O)_2NR^aR^a$, $-S(=O)_2N(R^a)C(=O)(R^b)$, $-S(=O)_2N(R^a)C(=O)O(R^b)$, $-S(=O)_2N(R^a)C(=O)NR^aR^a$, $-NR^aR^a$, $-N(R^a)C(=O)(R^b)$, $-N(R^a)C(=O)O(R^b)$, $-N(R^a)C(=O)NR^aR^a$, $-N(R^a)C(=NR^a)NR^aR^a$, $-N(R^a)S(=O)_2(R^b)$, $-N(R^a)S(=O)_2NR^aR^a$, $-NR^aC_{2-6}alkylNR^aR^a$ and $-NR^aC_{2-6}alkylOR^a$; or $R^8$ is $C_{1-4}$alkyl substituted by 0, 1, 2 or 3 groups selected from $C_{1-4}$haloalkyl, halo, cyano, nitro, $-C(=O)(R^b)$, $-C(=O)O(R^b)$, $-C(=O)NR^aR^a$, $-C(=NR^a)NR^aR^a$, $-OR^a$, $-OC(=O)(R^b)$, $-OC(=O)NR^aR^a$, $-OC(=O)N(R^a)S(=O)_2(R^b)$, $-OC_{2-6}alkylNR^aR^a$, $-OC_{2-6}alkylOR^a$, $-SR^a$, $-S(=O)(R^b)$, $-S(=O)_2(R^b)$, $-S(=O)_2NR^aR^a$, $-S(=O)_2N(R^a)C(=O)(R^b)$, $-S(=O)_2N(R^a)C(=O)O(R^b)$, $-S(=O)_2N(R^a)C(=O)NR^aR^a$, $-NR^aR^a$, $-N(R^a)C(=O)(R^b)$, $-N(R^a)C(=O)O(R^b)$, $-N(R^a)C(=O)NR^aR^a$, $-N(R^a)C(=NR^a)NR^aR^a$, $-N(R^a)S(=O)_2(R^b)$, $-N(R^a)S(=O)_2NR^aR^a$, $-NR^aC_{2-6}alkylNR^aR^a$ and $-NR^aC_{2-6}alkylOR^a$;

$R^9$ is independently, at each instance, selected from H, $C_{1-8}$alkyl, $C_{1-4}$haloalkyl, halo, cyano, nitro, $-C(=O)(R^b)$, $-C(=O)O(R^b)$, $-C(=O)NR^aR^a$, $-C(=NR^a)NR^aR^a$, $-OR^a$, $-OC(=O)(R^b)$, $-OC(=O)NR^aR^a$, $-OC(=O)N(R^a)S(=O)_2(R^b)$, $-OC_{2-6}alkylNR^aR^a$, $-OC_{2-6}alkylOR^aSR^a$, $-S(=O)(R^b)$, $-S(=O)_2(R^b)$, $-S(=O)_2NR^aR^a$, $-S(=O)_2N(R^a)C(=O)(R^b)$, $-S(=O)_2N(R^a)C(=O)O(R^b)$, $-S(=O)_2N(R^a)C(=O)NR^aR^a$, $-NR^aR^a$, $-N(R^a)C(=O)(R^b)$, $-N(R^a)C(=O)O(R^b)$, $-N(R^a)C(=O)NR^aR^a$, $-N(R^a)C(=NR^a)NR^aR^a$, $-N(R^a)S(=O)_2(R^b)$, $-N(R^a)S(=O)_2NR^aR^a$, $-NR^aC_{2-6}alkylNR^aR^a$ and $-NR^aC_{2-6}alkylOR^a$; or $R^9$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, $-C(=O)(R^b)$, $-C(=O)O(R^b)$, $-C(=O)NR^aR^a$, $-C(=NR^a)NR^aR^a$, $-OR^a$, $-OC(=O)(R^b)$, $-C(=O)NR^aR^a$, $-OC(=O)N(R^a)S(=O)_2(R^b)$, $-OC_{2-6}alkylNR^aR^a$, $-OC_{2-6}alkylOR^a$, $-SR^a$, $-S(=O)(R^b)$, $-S(=O)_2(R^b)$, $-S(=O)_2NR^aR^a$, $-S(=O)_2N(R^a)C(=O)(R^b)$, $-S(=O)_2N(R^a)C(=O)O(R^b)$, $-S(=O)_2N(R^a)C(=O)NR^aR^a$, $-NR^aR^a$, $-N(R^a)C(=O)(R^b)$, $-N(R^a)C(=O)O(R^b)$, $-N(R^a)C(=O)NR^aR^a$, $-N(R^a)C(=NR^a)NR^aR^a$, $-N(R^a)S(=O)_2(R^b)$, $-N(R^a)S(=O)_2NR^aR^a$, $-NR^aC_{2-6}alkylNR^aR^a$ and $-NR^aC_{2-6}alkylOR^a$; or $R^9$ is $C_{1-4}$alkyl substituted by 0, 1, 2 or 3 groups selected from $C_{1-4}$haloalkyl, halo, cyano, nitro, $-C(=O)(R^b)$, $-C(=O)O(R^b)$, $-C(=O)NR^aR^a$, $-C(=NR^a)NR^aR^a$, $-OR^a$, $-OC(=O)(R^b)$, $-OC(=O)NR^aR^a$, $-OC(=O)N(R^a)S(=O)_2(R^b)$, —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; wherein at least one of R$^5$, R$^6$, R$^7$, R$^8$ and R$^9$ is other than H;

R$^{10}$ is H, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^{10}$ is phenyl, R$^g$, C$_{1-8}$alkyl, C$_{1-4}$alkylphenyl, C$_{1-4}$alkylR$^g$, all of which are substituted by 0, 1, 2 or 3 groups selected from C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$ —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^{11}$ is, independently, in each instance, H, halo, —NH$_2$, —NHC$_{1-3}$alkyl, —N(C$_{1-3}$alkyl)C$_{1-3}$alkyl, or C$_{1-3}$alkyl;

R$^a$ is independently, at each instance, H or R$^b$;

R$^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, OH, —NH$_2$, —NHC$_{1-4}$alkyl, —N(C$_{1-4}$alkyl)C$_{1-4}$alkyl;

R$^c$ is independently, in each instance, phenyl substituted by 0, 1 or 2 groups selected from halo, C$_{1-4}$alkyl, C$_{1-3}$haloalkyl, —OR$^a$ and —NR$^a$R$^a$; or R$^c$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo groups, wherein the heterocycle or fused phenyl ring is substituted by 0, 1, 2 or 3 substituents selected from halo, C$_{1-4}$alkyl, C$_{1-3}$haloalkyl, —OR$^a$ and —NR$^a$R$^a$;

R$^e$ is, independently, in each instance, C$^{1-9}$alkyl substituted by 0, 1, 2, 3 or 4 substituents selected from halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and wherein the C$_{1-9}$alkyl is additionally substituted by 0 or 1 groups independently selected from R$^g$;

R$^f$ is, independently, in each instance, R$^e$ or H; and

R$^g$ is, independently, in each instance, a saturated or unsaturated 5- or 6-membered monocyclic ring containing 1, 2 or 3 atoms selected from N, O and S, so long as the combination of O and S atoms is not greater than 2, wherein the carbon atoms of the ring are substituted by 0 or 1 oxo groups.

In another embodiment, in conjunction with any one of the above and below embodiments, J is NH.

In another embodiment, in conjunction with any one of the above and below embodiments, J is O.

In another embodiment, in conjunction with any one of the above and below embodiments, J is S.

In another embodiment, in conjunction with any one of the above and below embodiments, X$^1$ is N.

In another embodiment, in conjunction with any one of the above and below embodiments, X$^1$ is C.

In another embodiment, in conjunction with any one of the above and below embodiments, X$^2$ is N.

In another embodiment, in conjunction with any one of the above and below embodiments, X$^2$ is C.

In another embodiment, in conjunction with any one of the above and below embodiments, Y is N and Z is C(R$^{10}$).

In another embodiment, in conjunction with any one of the above and below embodiments, Y is C(R$^{11}$) and Z is N.

In another embodiment, in conjunction with any one of the above and below embodiments, Y is C(R$^{11}$) and Z is C(R$^{10}$).

In another embodiment, in conjunction with any one of the above and below embodiments, n is 1 or 2.

In another embodiment, in conjunction with any one of the above and below embodiments, n is 0.

In another embodiment, in conjunction with any one of the above and below embodiments, m is 0 or 1.

In another embodiment, in conjunction with any one of the above and below embodiments, m is 0 or 1.

In another embodiment, in conjunction with any one of the above and below embodiments, X$^1$ and X$^2$ are both C; and R$^1$ is —OR$^b$ or C$_{1-6}$alkyl substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$ —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by 0 or 1 substituents selected from a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —C(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^1$ is C$_{1-6}$heteroalkyl chain substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkyNR$^a$R$^a$ and —NR$^a$C$_{2-6}$alkylOR$^a$.

In another embodiment, in conjunction with any one of the above and below embodiments, X$^1$ and X$^2$ are both C; and R$^1$ is C$_{1-6}$alkyl substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, at least one of X$^1$ and X$^2$ is N;

J is NH; and

R$^1$ is C$_{1-6}$alkyl substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylN-R$^a$R$^2$ and —NR$^a$C$_{2-6}$alkylOR$^a$, and additionally substituted by a substituent selected from i) a saturated, partially saturated or unsaturated 5-, 6- or 7-membered ring containing 1, 2, 3 or 4 atoms selected from N, O and S, wherein the carbon atoms of the ring are substituted by 0, 1 or 2 oxo groups and the ring is substituted by 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and ii) phenyl substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^1$ is C$_{1-6}$heteroalkyl chain substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —C(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, at least one of X$^1$ and X$^2$ is N;

J is NH; and

R$^1$ is C$_{1-6}$alkyl substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by a saturated, partially saturated or unsaturated 5-, 6- or 7-membered ring containing 1, 2, 3 or 4 atoms selected from N, O and S, wherein the carbon atoms of the ring are substituted by 0, 1 or 2 oxo groups and the ring is substituted by 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, at least one of X$^1$ and X$^2$ is N;

J is NH; and

R$^1$ is C$_{1-6}$alkyl substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by phenyl substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, at least one of X$^1$ and X$^2$ is N;

J is O;

Y and Z are both CH; and

R$^1$ is C$_{1-6}$alkyl substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^1$ is C$_{1-6}$heteroalkyl chain substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, at least one of X$^1$ and X$^2$ is N;

J is O;

Y and Z are both CH; and

R$^1$ is C$_{1-6}$alkyl substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C (=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, at least one of X$^1$ and X$^2$ is N;
J is O;
Y and Z are both CH; and
R$^1$ is C$_{1-6}$alkyl substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by a saturated, partially saturated or unsaturated 5-, 6- or 7-membered ring containing 1, 2, 3 or 4 atoms selected from N, O and S, wherein the carbon atoms of the ring are substituted by 0, 1 or 2 oxo groups and the ring is substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, at least one of X$^1$ and X$^2$ is N;
J is O;
Y and Z are both CH; and
R$^1$ is C$_{1-6}$alkyl substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by phenyl substituted by 0, 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, R$^2$ is C$_{1-6}$alkyl.

In another embodiment, in conjunction with any one of the above and below embodiments, R$^2$ is C$_{1-4}$haloalkyl.

In another embodiment, in conjunction with any one of the above and below embodiments, R$^2$ is, independently, in each instance, F, Cl, or Br.

In another embodiment, in conjunction with any one of the above and below embodiments, R$^{2'}$ is OR$^b$, —NR$^a$R$^b$, —SR$^b$, —S(=O)R$^b$ or —S(=O)$_2$R$^b$.

In another embodiment, in conjunction with any one of the above and below embodiments, R$^{2'}$ is C$_{1-6}$alkyl substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by 0 or 1 substituents selected from a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, R$^{2'}$ is C$_{1-6}$alkyl substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, R$^{2'}$ is C$_{1-6}$heteroalkyl chain substituted by 0, 1, 2 or 3 substituents independently selected from $C_{1-4}$haloalkyl, halo, cyano, oxo, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$.

In another embodiment, in conjunction with any one of the above and below embodiments, $R^4$ is

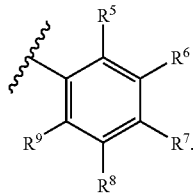

In another embodiment, in conjunction with any one of the above and below embodiments, $R^4$ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from $R^e$, $C_{1-4}$haloalkyl, halo, nitro, cyano, oxo, —O$R^f$, —S(=O)$_nR^e$, —O$C_{1-4}$haloalkyl, —O$C_{2-6}$alkylN$R^aR^f$, —O$C_{2-6}$alkylO$R^f$, —O$C_{1-6}$alkylC(=O)O$R^e$, —N$R^aR^f$, —N$R^aC$4haloalkyl, —N$R^aC_{2-6}$alkylN$R^aR^f$, —N$R^aC_{2-6}$alkylO$R^f$, —C(=O)$R^e$, —C(=O)O$R^e$, —OC(=O)$R^e$, —C(=O)N$R^aR^f$ and —N$R^aC$(=O)$R^e$; and unsaturated carbon atoms may be additionally substituted by =O; and any available nitrogen atoms in the heterocycle and bridge are substituted by H, —$C_{1-6}$alkylO$R^f$, $R^e$, —$C_{1-6}$alkylN$R^aR^f$, —$C_{1-3}$alkylC(=O)O$R^e$, —$C_{1-3}$alkylC(=O)N$R^aR^f$, —$C_{1-3}$alkylOC(=O)$R^e$, —$C_{1-3}$alkylN$R^aC$(=O)$R^e$, —C(=O)$R^e$ or —$C_{1-3}$alkyl$R^c$;

In another embodiment, in conjunction with any one of the above and below embodiments, $R^4$ is a saturated or unsaturated 5- or 6-membered ring heterocycle containing 1, 2 or 3 atoms selected from O, N and S that is vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from $R^e$, $C_{1-4}$haloalkyl, halo, nitro, cyano, oxo, —O$R^f$, —S(=O)$_nR^e$, —O$C_{1-4}$haloalkyl, —O$C_{2-6}$alkylN$R^aR^f$, —O$C_{2-6}$alkylO$R^f$, —O$C_{1-6}$alkylC(=O)O$R^e$, —N$R^aR^f$, —N$R^aC_{1-4}$haloalkyl, —N$R^aC_{2-6}$alkylN$R^aR^f$, —N$R^aC_{2-6}$alkylO$R^f$, —C(=O)$R^e$, —C(=O)O$R^e$, —Oc(=O)$R^e$, —C(=O)N$R^aR^f$ and —N$R^aC$(=O)$R^e$; and unsaturated carbon atoms may be additionally substituted by =O; and any available nitrogen atoms in the heterocycle and bridge are substituted by H, —$C_{1-6}$alkylO$R^f$, $R^e$, —$C_{1-6}$alkylN$R^aR^f$, —$C_{1-3}$alkylC(=O)O$R^e$, —$C_{1-3}$alkylC(=O)N$R^aR^f$, —$C_{1-3}$alkylOC(=O)$R^e$, —$C_{1-3}$alkylN$R^aC$(=O)$R^e$, —C(=O)$R^e$ or —$C_{1-3}$alkyl$R^c$.

In another embodiment, in conjunction with any one of the above and below embodiments, $R^4$ is naphthyl substituted by 1, 2 or 3 substituents independently selected from $C_{1-4}$haloalkyl, halo, nitro, cyano, —S(=O)$_nR^e$, —O$C_{1-4}$haloalkyl, —O$C_{2-6}$alkylN$R^aR^f$, —O$C_{2-6}$alkylO$R^f$, —O$C_{1-6}$alkylC(=O)O$R^e$, —N$R^aC_{1-4}$haloalkyl, —N$R^aC_{2-6}$alkylN$R^aR^f$, —N$R^aC_{2-6}$alkylO$R^f$, —C(=O)$R^e$, —C(=O)O$R^e$, —OC(=O)$R^e$ and —C(=O)N$R^aR^f$;

In another embodiment, in conjunction with any one of the above and below embodiments, $R^5$ is independently, at each instance, selected from H, $C_{1-8}$alkyl, $C_{1-4}$haloalkyl, halo, cyano, nitro, —C(=O)($R^b$), —C(=O)O($R^b$), —C(=O)N$R^aR^a$, —C(=N$R^a$)N$R^aR^a$, —O$R^a$, —OC(=O)($R^b$), —OC(=O)N$R^aR^a$, —OC(=O)N($R^a$)S(=O)$_2$($R^b$), —O$C_{2-6}$ alkylN$R^aR^a$, —O$C_{2-6}$alkylO$R^a$, —S$R^a$, —S(=O)($R^b$), —S(=O)$_2$($R^b$), —S(=O)$_2$N$R^aR^a$, —S(=O)$_2$N($R^a$)C(=O)($R^b$), —S(=O)$_2$N($R^a$)C(=O)O($R^b$), —S(=O)$_2$N($R^a$)C(=O)N$R^aR^a$, —N$R^aR^a$, —N($R^a$)C(=O)($R^b$), —N($R^a$)C(=O)O($R^b$), —N($R^a$)C(=O)N$R^aR^a$, —N($R^a$)C(=N$R^a$)N$R^aR^a$, —N($R^a$)S(=O)$_2$($R^b$), —N($R^a$)S(=O)$_2$N$R^aR^a$, —N$R^aC_{2-6}$alkylN$R^aR^a$ and —N$R^aC_{2-6}$alkylO$R^a$.

In another embodiment, in conjunction with any one of the above and below embodiments, $R^5$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($R^b$), —C(=O)O($R^b$), —C(=O)N$R^aR^a$, —C(=N$R^a$)N$R^aR^a$, —O$R^a$, —OC(=O)($R^b$), —OC(=O)N$R^aR^a$, —OC(=O)N($R^a$)S(=O)$_2$($R^b$), —O$C_{2-6}$alkylN$R^aR^a$, —O$C_{2-6}$alkylO$R^a$, —S$R^a$, —S(=O)($R^b$), —S(=O)$_2$($R^b$), —S(=O)$_2$N$R^aR^a$, —S(=O)$_2$N($R^a$)C(=O)($R^b$), —S(=O)$_2$N($R^a$)C(=O)O($R^b$), —S(=O)$_2$N($R^a$)C(=O)N$R^aR^a$, —N$R^aR^a$, —N($R^a$)C(=O)($R^b$), —N($R^a$)C(=O)O($R^b$), —N($R^a$)C(=O)N$R^aR^a$, —N($R^a$)C(=N$R^a$)N$R^aR^a$, —N($R^a$)S(=O)$_2$($R^b$), —N($R^a$)S(=O)$_2$N$R^aR^a$, —N$R^aC_{2-6}$alkylN$R^aR^a$ and —N$R^aC_{2-6}$alkylO$R^a$.

In another embodiment, in conjunction with any one of the above and below embodiments, $R^5$ is $C_{1-4}$alkyl substituted by 0, 1, 2 or 3 groups selected from $C_{1-4}$haloalkyl, halo, cyano, nitro, —C(=O)($R^b$), —C(=O)O($R^b$), —C(=O)N$R^aR^a$, —C(=N$R^a$)N$R^aR^a$, —O$R^a$, —OC(=O)($R^b$), —OC(=O)N$R^aR^a$, —OC(=O)N($R^a$)S(=O)$_2$($R^b$), —O$C_{2-6}$alkylN$R^aR^a$, —O$C_{2-6}$alkylO$R^a$, —S$R^a$, —S(=O)($R^b$), —S(=O)$_2$($R^b$), —S(=O)$_2$N$R^aR^a$, —S(=O)$_2$N($R^a$)C(=O)($R^b$), —S(=O)$_2$N($R^a$)C(=O)O($R^b$), —S(=O)$_2$N($R^a$)C(=O)N$R^aR^a$, —N$R^aR^a$, —N($R^a$)C(=O)($R^b$), —N($R^a$)C(=O)O($R^b$), —N($R^a$)C(=O)N$R^aR^a$, —N($R^a$)C(=N$R^a$)N$R^aR^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, R$^6$ is independently, at each instance, selected from H, C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, R$^6$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —C(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, R$^6$ is C$_{1-4}$alkyl substituted by 0, 1, 2 or 3 groups selected from C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, R$^5$ and R$^6$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 0, 1, 2 or 3 substituents selected from =O, R$^e$, halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —C(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$.

In another embodiment, in conjunction with any one of the above and below embodiments, R$^5$ and R$^6$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 1, 2 or 3 substituents selected from =O, R$^e$, halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$.

In another embodiment, in conjunction with any one of the above and below embodiments, R$^7$ is independently, at each instance, selected from H, C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —N(R$^a$)C(=O)(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, R$^7$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, R$^7$ is C$_{1-4}$alkyl substituted by 0, 1, 2 or 3 groups selected from C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —C(=O)(R$^b$), —C(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, R$^6$ and R$^7$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 0, 1, 2 or 3 substituents selected from =O, $R^e$, halo, cyano, nitro, —C(=O)$R^e$, —C(=O)$R^e$, —C(=O)N$R^aR^f$, —C(=N$R^a$)N$R^aR^f$, —O$R^f$, —OC(=O)$R^e$, —OC(=O)N$R^aR^f$, —OC(=O)N($R^f$)S(=O)$_2R^e$, —OC$_{2-6}$alkylN$R^aR^f$, —OC$_{2-6}$alkylO$R^f$, —S$R^f$, —S(=O)$R^e$, —S(=O)$_2R^e$, —S(=O)$_2$N$R^aR^f$, —S(=O)$_2$N($R^f$)C(=O)$R^e$, —S(=O)$_2$N($R^f$)C(=O)O$R^e$, —S(=O)$_2$N($R^f$)C(=O)N$R^aR^f$, —N$R^aR^f$, —N($R^f$)C(=O)$R^e$, —N($R^f$)C(=O)O$R^e$, —N($R^f$)C(=O)N$R^aR^f$, —N($R^f$)C(=N$R^a$)N$R^aR^f$, —N($R^f$)S(=O)$_2R^e$, —N($R^f$)S(=O)$_2$N$R^aR^f$, —N$R^f$C$_{2-6}$alkylN$R^aR^f$ and —N$R^f$C$_{2-6}$alkylO$R^f$.

In another embodiment, in conjunction with any one of the above and below embodiments, $R^6$ and $R^7$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 1, 2 or 3 substituents selected from =O, $R^e$, halo, cyano, nitro, —C(=O)$R^e$, —C(=O)O$R^e$, —C(=O)N$R^aR^f$, —C(=N$R^a$)N$R^aR^f$, —O$R^f$, —OC(=O)$R^e$, —OC(=O)N$R^aR^f$, —OC(=O)N($R^f$)S(=O)$_2R^e$, —OC$_{2-6}$alkylN$R^aR^f$, —OC$_{2-6}$alkylO$R^f$, —S$R^f$, —S(=O)$R^e$, —S(=O)$_2R^e$, —S(=O)$_2$N$R^aR^f$, —S(=O)$_2$N($R^f$)C(=O)$R^e$, —S(=O)$_2$N($R^f$)C(=O)O$R^e$, —S(=O)$_2$N($R^f$)C(=O)N$R^aR^f$, —N$R^aR^f$, —N($R^f$)C(=O)$R^e$, —N($R^f$)C(=O)O$R^e$, —N($R^f$)C(=O)N$R^aR^f$, —N($R^f$)C(=N$R^a$)N$R^aR^f$, —N($R^f$)S(=O)$_2R^e$, —N($R^f$)S(=O)$_2$N$R^aR^f$, —N$R^f$C$_{2-6}$alkylN$R^aR^a$ and —N$R^f$C$_{2-6}$alkylO$R^f$.

In another embodiment, in conjunction with any one of the above and below embodiments, $R^8$ is independently, at each instance, selected from H, $C_{1-8}$alkyl, $C_{1-4}$haloalkyl, halo, cyano, nitro, —C(=O)($R^b$), —C(=O)O($R^b$), —C(=O)N$R^aR^a$, —C(=N$R^a$)N$R^aR^a$, —O$R^a$, —OC(=O)($R^b$), —OC(=O)N$R^aR^a$, —OC(=O)N($R^a$)S(=O)$_2$($R^b$), —OC$_{2-6}$alkylN$R^aR^a$, —OC$_{2-6}$alkylO$R^a$, —S$R^a$, —S(=O)($R^b$), —S(=O)$_2$($R^b$), —S(=O)$_2$N$R^aR^a$, —S(=O)$_2$N($R^a$)C(=O)($R^b$), —S(=O)$_2$N($R^a$)C(=O)O($R^b$), —S(=O)$_2$N($R^a$)C(=O)N$R^aR^a$, —N$R^aR^a$, —N($R^a$)C(=O)($R^b$), —N($R^a$)C(=O)O($R^b$), —N($R^a$)C(=O)N$R^aR^a$, —N($R^a$)C(=N$R^a$)N$R^aR^a$, —N($R^a$)S(=O)$_2$($R^b$), —N($R^a$)S(=O)$_2$N$R^aR^a$, —N$R^a$C$_{2-6}$alkylN$R^aR^a$ and —N$R^a$C$_{2-6}$alkylO$R^a$.

In another embodiment, in conjunction with any one of the above and below embodiments, $R^8$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($R^b$), —C(=O)O($R^b$), —C(=O)N$R^aR^a$, —C(=N$R^a$)N$R^aR^a$, —O$R^a$, —OC(=O)($R^b$), —OC(=O)N$R^aR^a$, —OC(=O)N($R^a$)S(=O)$_2$($R^b$), —OC$_{2-6}$alkylN$R^aR^a$, —OC$_{2-6}$alkylO$R^a$, —S$R^a$, —S(=O)($R^b$), —S(=O)$_2$($R^b$), —S(=O)$_2$N$R^aR^a$, —S(=O)$_2$N($R^a$)C(=O)($R^b$), —S(=O)$_2$N($R^a$)C(=O)O($R^b$), —S(=O)$_2$N($R^a$)C(=O)N$R^aR^a$, —N$R^aR^a$, —N($R^a$)C(=O)($R^b$), —N($R^a$)C(=O)O($R^b$), —N($R^a$)C(=O)N$R^aR^a$, —N($R^a$)C(=N$R^a$)N$R^aR^a$, —N($R^a$)S(=O)$_2$($R^b$), —N($R^a$)S(=O)$_2$N$R^aR^a$, —N$R^a$C$_{2-6}$alkylN$R^aR^a$ and —N$R^a$C$_{2-6}$alkylO$R^a$.

In another embodiment, in conjunction with any one of the above and below embodiments, $R^8$ is $C_{1-4}$alkyl substituted by 0, 1, 2 or 3 groups selected from $C_{1-4}$haloalkyl, halo, cyano, nitro, —C(=O)($R^b$), —C(=O)O($R^b$), —C(=O)N$R^aR^a$, —C(=N$R^a$)N$R^aR^a$, —O$R^a$, —OC(=O)($R^b$), —C(=O)N$R^aR^a$, —OC(=O)N($R^a$)S(=O)$_2$($R^b$), —OC$_{2-6}$alkylN$R^aR^a$, —OC$_{2-6}$alkylO$R^a$, —S$R^a$, —S(=O)($R^b$), —S(=O)$_2$($R^b$), —S(=O)$_2$N$R^aR^a$, —S(=O)$_2$N($R^a$)C(=O)($R^b$), —S(=O)$_2$N($R^a$)C(=O)O($R^b$), —S(=O)$_2$N($R^a$)C(=O)N$R^aR^a$, —N$R^aR^a$, —N($R^a$)C(=O)($R^b$), —N($R^a$)C(=O)O($R^b$), —N($R^a$)C(=O)N$R^aR^a$, —N($R^a$)C(=N$R^a$)N$R^aR^a$, —N($R^a$)S(=O)$_2$($R^b$), —N($R^a$)S(=O)$_2$N$R^aR^a$, —N$R^a$C$_{2-6}$alkylN$R^aR^a$ and —N$R^a$C$_{2-6}$alkylO$R^a$.

In another embodiment, in conjunction with any one of the above and below embodiments, $R^9$ is independently, at each instance, selected from H, $C_{1-8}$alkyl, $C_{1-4}$haloalkyl, halo, cyano, nitro, —C(=O)($R^b$), —C(=O)O($R^b$), —C(=O)N$R^aR^a$, —C(=N$R^a$)N$R^aR^a$, —O$R^a$, —OC(=O)($R^b$), —OC(=O)N$R^aR^a$, —OC(=O)N($R^a$)S(=O)$_2$($R^b$), —OC$_{2-6}$alkylN$R^aR^a$, —OC$_{2-6}$alkylO$R^a$, —S$R^a$, —S(=O)($R^b$), —S(=O)$_2$($R^b$), —S(=O)$_2$N$R^aR^a$, —S(=O)$_2$N($R^a$)C(=O)($R^b$), —S(=O)$_2$N($R^a$)C(=O)O($R^b$), —S(=O)$_2$N($R^a$)C(=O)N$R^aR^a$, —N$R^aR^a$, —N($R^a$)C(=O)($R^b$), —N($R^a$)C(=O)O($R^b$), —N($R^a$)C(=O)N$R^aR^a$, —N($R^a$)C(=N$R^a$)N$R^aR^a$, —N($R^a$)S(=O)$_2$($R^b$), —N($R^a$)S(=O)$_2$N$R^aR^a$, —N$R^a$C$_{2-6}$alkylN$R^aR^a$ and —N$R^a$C$_{2-6}$alkylO$R^a$.

In another embodiment, in conjunction with any one of the above and below embodiments, $R^9$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from $C_{1-8}$alkyl, $C_{1-4}$haloalkyl, halo, cyano, nitro, —C(=O)($R^b$), —C(=O)O($R^b$), —C(=O)N$R^aR^a$, —C(=N$R^a$)N$R^aR^a$, —O$R^a$, —OC(=O)($R^b$), —OC(=O)N$R^aR^a$, —OC(=O)N($R^a$)S(=O)$_2$($R^b$), —OC$_{2-6}$alkylN$R^aR^a$, —OC$_{2-6}$alkylO$R^a$, —S$R^a$, —S(=O)($R^b$), —S(=O)$_2$($R^b$), —S(=O)$_2$N$R^aR^a$, —S(=O)$_2$N($R^a$)C(=O)($R^b$), —S(=O)$_2$N($R^a$)C(=O)O($R^b$), —S(=O)$_2$N($R^a$)C(=O)N$R^aR^a$, —N$R^aR^a$, —N($R^a$)C(=O)($R^b$), —N($R^a$)C(=O)O($R^b$), —N($R^a$)C(=O)N$R^aR^a$, —N($R^a$)C(=N$R^a$)N$R^aR^a$, —N($R^a$)S(=O)$_2$($R^b$), —N($R^a$)S(=O)$_2$N$R^aR^a$, —N$R^a$C$_{2-6}$alkylN$R^aR^a$ and —N$R^a$C$_{2-6}$alkylO$R^a$.

In another embodiment, in conjunction with any one of the above and below embodiments, $R^9$ is $C_{1-4}$alkyl substituted by 0, 1, 2 or 3 groups selected from $C_{1-4}$haloalkyl, halo, cyano, nitro, —C(=O)($R^b$), —C(=O)O($R^b$), —C(=O)N$R^aR^a$, —C(=N$R^a$)N$R^aR^a$, —O$R^a$, —OC(=O)($R^b$), —C(=O)N$R^aR^a$, —OC(=O)N($R^a$)S(=O)$_2$($R^b$), —OC$_{2-6}$alkylN$R^aR^a$, —OC$_{2-6}$alkylO$R^a$, —S$R^a$, —S(=O)($R^b$), —S(=O)$_2$($R^b$), —S(=O)$_2$N$R^aR^a$, —S(=O)$_2$N($R^a$)C(=O)($R^b$), —S(=O)$_2$N($R^a$)C(=O)O($R^b$), —S(=O)$_2$N($R^a$)C(=O)N$R^aR^a$, —N$R^aR^a$, —N($R^a$)C(=O)($R^b$), —N($R^a$)C(=O)O($R^b$), —N($R^a$)C(=O)N$R^aR^a$, —N($R^a$)C(=N$R^a$)N$R^aR^a$, —N($R^a$)S(=O)$_2$($R^b$), —N($R^a$)S(=O)$_2$N$R^aR^a$, —N$R^a$C$_{2-6}$alkylN$R^aR^a$ and —N$R^a$C$_{2-6}$alkylO$R^a$; wherein at least one of $R^5$, $R^6$, $R^7$, $R^8$ and $R^9$ is other than H.

In another embodiment, in conjunction with any one of the above and below embodiments, $R^{10}$ is H, $C_{1-4}$haloalkyl, halo, cyano, nitro, —C(=O)($R^b$), —C(=O)O($R^b$), —C(=O)N$R^aR^a$, —C(=N$R^a$)N$R^aR^a$, —O$R^a$, —OC(=O)($R^b$), —OC(=O)N$R^aR^a$, —OC(=O)N($R^a$)S(=O)$_2$($R^b$), —OC$_{2-6}$alkylN$R^aR^a$, —OC$_{2-6}$alkylO$R^a$, —S$R^a$, —S(=O)($R^b$), —S(=O)$_2$($R^b$), —S(=O)$_2$N$R^aR^a$, —S(=O)$_2$N($R^a$)C(=O)($R^b$), —S(=O)$_2$N($R^a$)C(=O)O($R^b$), —S(=O)$_2$N($R^a$)C(=O)N$R^aR^a$, —N$R^aR^a$, —N($R^a$)C(=O)($R^b$), —N($R^a$)C(=O)O($R^b$), —N($R^a$)C(=O)N$R^aR^a$, —N($R^a$)C(=N$R^a$)N$R^aR^a$, —N($R^a$)S(=O)$_2$($R^b$), —N($R^a$)S(=O)$_2$N$R^aR^a$, —N$R^a$C$_{2-6}$alkylN$R^aR^a$ and —N$R^a$C$_{2-6}$alkylO$R^a$.

In another embodiment, in conjunction with any one of the above and below embodiments, $R^{10}$ is phenyl, $R^g$, $C_{1-8}$alkyl, $C_{1-4}$alkylphenyl, $C_{1-4}$alkylR$^g$, all of which are substituted by 0, 1, 2 or 3 groups selected from $C_{1-8}$alkyl, $C_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$.

In another embodiment, in conjunction with any one of the above and below embodiments, $R^{11}$ is, independently, in each instance, H, halo, —NH$_2$, —NHC$_{1-3}$alkyl, —N(C$_{1-3}$alkyl)C$_{1-3}$alkyl, or C$_{1-3}$alkyl.

In another embodiment, in conjunction with any one of the above and below embodiments, $R^{11}$ is H.

In another embodiment, in conjunction with any one of the above and below embodiments, $R^{11}$ is, independently, in each instance, halo, —NH$_2$, —NHC$_{1-3}$alkyl, —N(C$_{1-3}$alkyl)C$_{1-3}$alkyl, or C$_{1-3}$alkyl.

Another aspect of the invention relates to a method of treating acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, anxiety, depression, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, comprising the step of administering a compound according to any of the above embodiments.

Another aspect of the invention relates to a pharmaceutical composition comprising a compound according to any of the above embodiments and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, anxiety, depression, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritus, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders.

Another aspect of the invention relates to a method of making a compound according to the above embodiments, comprising the step of:

reacting

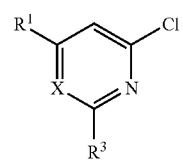

with R$_2$NH$_2$ to form

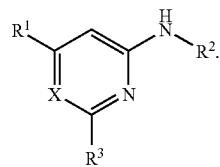

The compounds of this invention may have in general several asymmetric centers and are typically depicted in the form of racemic mixtures. This invention is intended to encompass racemic mixtures, partially racemic mixtures and separate enantiomers and diastereomers.

Unless otherwise specified, the following definitions apply to terms found in the specification and claims:

"C$_{\alpha-\beta}$alkyl" means an alkyl group comprising a minimum of α and a maximum of β carbon atoms in a branched, cyclical or linear relationship or any combination of the three, wherein α and β represent integers. The alkyl groups described in this section may also contain one or two double or triple bonds. Examples of C$_{1-6}$alkyl include, but are not limited to the following:

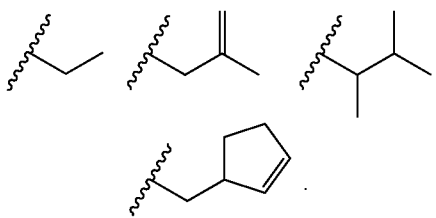

"C$_{3-6}$heteroalkyl chain" means a three to six atom chain made up of 2 to 5 carbon atoms and at least one heteroatom selected from S, O and N, wherein there should be no adjacent heteroatoms in the chain, including the linkage to the parent structure. Examples of C$_{1-6}$heteroalkyl chains include, but are not limited to the following:

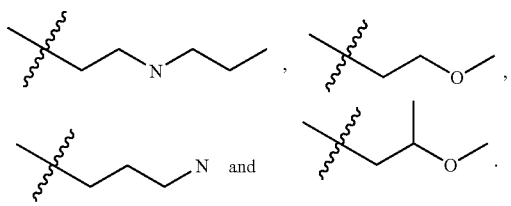

$C_{1-6}$heteroalkyl chains may be optionally substituted.

"Benzo group", alone or in combination, means the divalent radical $C_4H_4=$, one representation of which is —CH=CH—CH=CH—, that when vicinally attached to another ring forms a benzene-like ring—for example tetrahydronaphthylene, indole and the like. "Halo" or "halogen" means a halogen atoms selected from F, Cl, Br and I. "$C_{v-w}$haloalkyl" means an alkyl group, as described above, wherein any number—at least one—of the hydrogen atoms attached to the alkyl chain are replaced by F, Cl, Br or I. "Heterocycle" means a ring comprising at least one carbon atom and at least one other atom selected from N, O and S. Examples of heterocycles that may be found in the claims include, but are not limited to, the following:

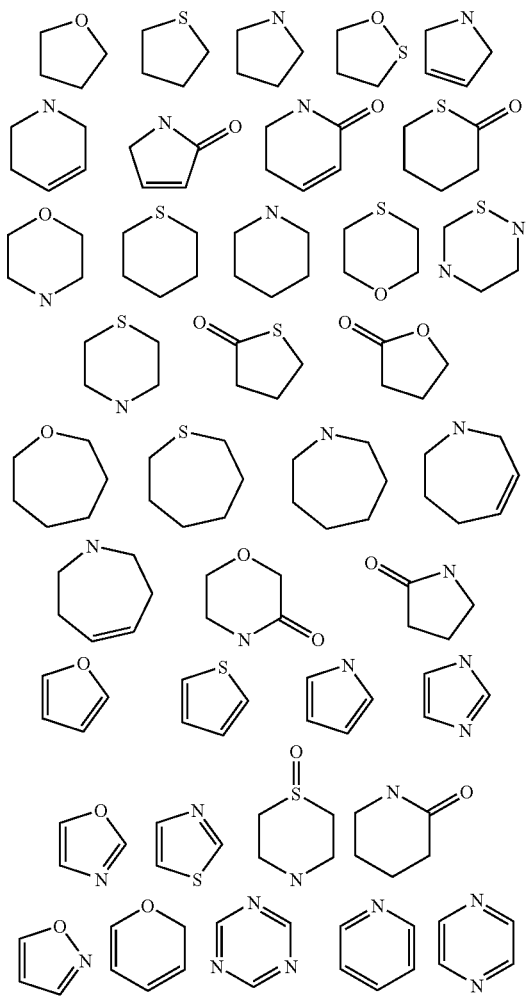

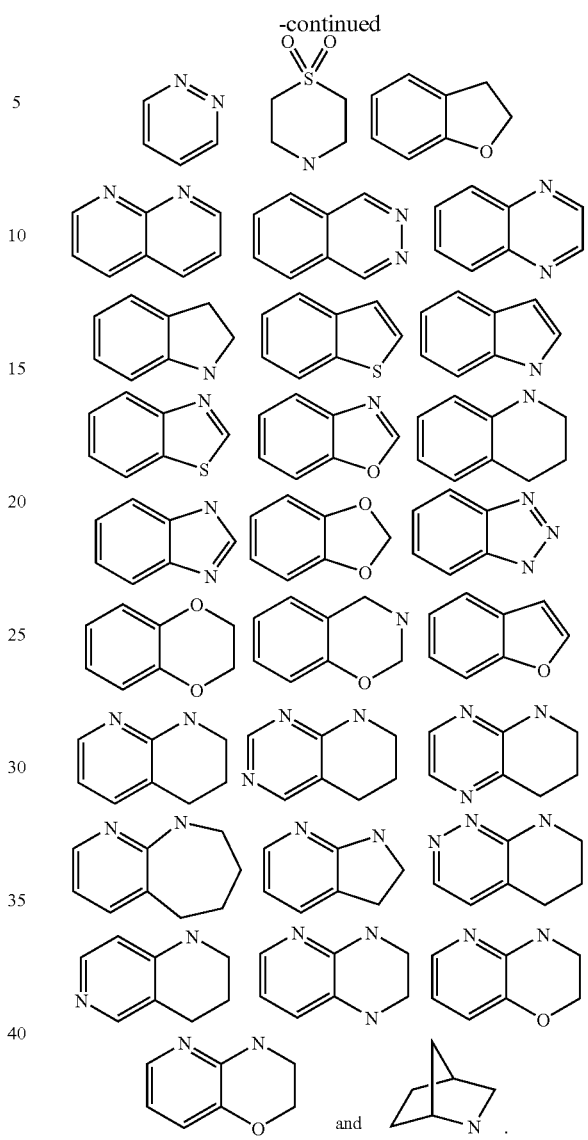

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups. Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

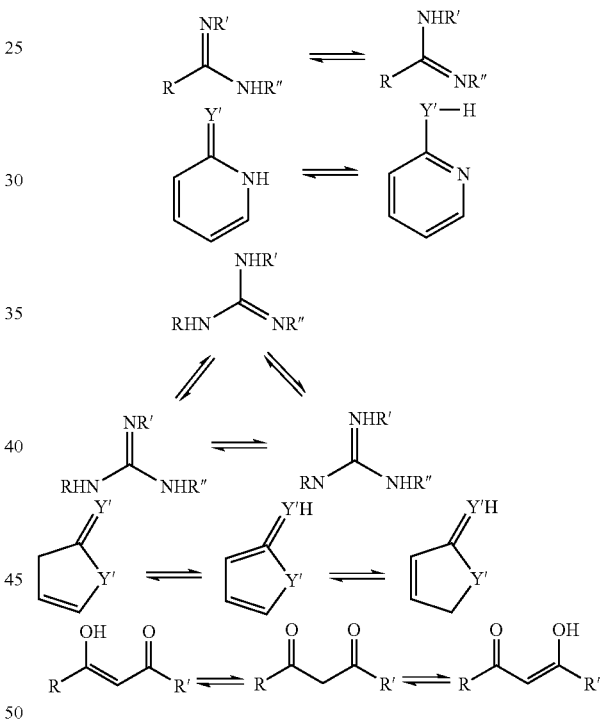

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism $R^e$ views 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species, embodiments and sub-embodiments using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

EXPERIMENTAL

Unless otherwise noted, all materials were obtained from commercial suppliers and used without further purification. All parts are by weight and temperatures are in degrees centigrade unless otherwise indicated. All microwave assisted reactions were conducted with a Smith Synthesizer from Personal Chemistry, Uppsala, Sweden. All compounds showed NMR spectra consistent with their assigned structures. Melting points were determined on a Buchi apparatus and are uncorrected. Mass spectral data was determined by electrospray ionization technique. All examples were purified to >90% purity as determined by high-performance liquid chromatography (HPLC). Unless otherwise stated, reactions were run at room temperature.

The following abbreviations are used:

| | |
|---|---|
| DMSO - | dimethyl sulfoxide |
| DMF - | N,N-dimethylformamide |
| THF - | tetrahydrofuran |
| $Et_2O$ - | diethyl ether |
| EtOAc - | ethyl acetate |
| MeOH - | methyl alcohol |
| EtOH - | ethyl alcohol |
| MeCN - | acetonitrile |
| MeI - | iodomethane |
| NMP - | 1-methyl-2-pyrrolidinone |
| DCM - | dichloromethane |
| TFA - | trifluoroacetic acid |
| MP-carbonate - | macroporous polystyrene anion-exchange resin that is a resin bound equivalent of tetraalkylammonium carbonate. |
| sat. - | saturated |
| h - | hour |
| min - | minutes |

EXAMPLE 1

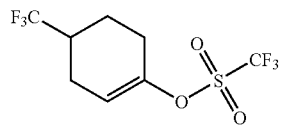

(a) Trifluoro-methanesulfonic acid 4-trifluoromethyl-cyclohex-1-enyl ester. To a solution of 4-trifluoromethylcyclohexanone (4.98 g, 30 mmol, Matrix) in THF (75 mL) was added dropwise lithium bis(trimethylsilyl)amide (30 mL, 30 mmol, 1M solution in THF, Aldrich) over a period of 30 min with stirring at −78° C. The mixture was stirred for 1 h at −78° C., and a solution of N-phenyltrifluoromethanesulfonimide (10.71 g, 30 mmol, Aldrich) in THF (75 mL) was added dropwise with stirring over a period of 30 min. The reaction mixture was stirred at −78° C. for 2 h and slowly warmed to room temperature with stirring over a period of 6 h. The reaction mixture was extracted with EtOAc (3×). The combined organic extracts were washed with water, dried over $Na_2SO_4$, and filtered. The filtrate was evaporated and the residue was purified by silica gel column chromatography (10% ethyl acetate/hexane) to give the title compound as a white solid.

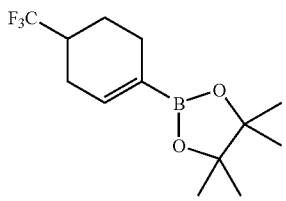

(b) 4,4,5,5-Tetramethyl-2-(4-trifluoromethyl-cyclohex-1-enyl)-[1,3,2]dioxaborolane. To a solution of trifluoromethanesulfonic acid 4-trifluoromethyl-cyclohex-1-enyl ester, Example 1(a), (6.1 g, 20.5 mmol) in dioxane (100 mL) was added bis(pinacolato)diboron (5.6 g, 22 mmol, Aldrich), potassium acetate (5.9 g, 60 mmol), $PdCl_2(dppf)$ (315 mg, 0.6 mmol, Strem) and dppf (332 mg, 0.6 mmol, Strem) under nitrogen atmosphere. The reaction mixture was heated at 80° C. with stirring for 18 h, cooled to room temperature, and filtered through Celite®. The filtrate was evaporated in vacuo and the residue was purified by silica gel column chromatography (10% ethyl acetate/hexane) to give the title compound as a white amorphous solid. MS (ESI, pos. ion.) m/z: 277 (M+1).

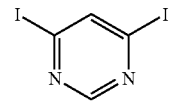

(c) 4,6-Diiodo-pyrimidine. A mixture of 4,6-dichloro-pyrimidine (1.0 g, 6.70 mmol, Aldrich), NaI (1.36 g, 9.00 mmol) and hydriodic acid (20 mL, 151.4 mmol) was heated at 40° C. with stirring for 1 h. The reaction mixture was stirred at room temperature for 20 h and basified with 10 N NaOH to pH 10. The resulting precipitate was filtered, washed with water, and dried in vacuo to give the title compound as a light-yellow solid. MS (ESI, pos. ion.) m/z: 332 (M+1).

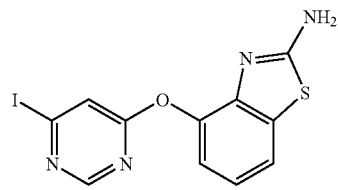

(d) 4-(6-Iodo-pyrimidin-4-yloxy)-benzothiazol-2-ylamine. A mixture of 4,6-diiodo-pyrimidine, Example 1(c), (723 mg, 2.18 mmol), 2-amino-benzothiazol-4-ol (361 mg, 2.18 mmol, Oakwood), and $K_2CO_3$ (425 mg, 3.07 mmol) in DMSO (3.0 mL) was heated at 80° C. for 1 h. The reaction mixture was allowed to cool to room temperature, diluted with water and stirred for 18 h. The resulting precipitate was filtered, washed with water, and dried in vacuo to give the title compound as a light-yellow solid. MS (ESI, pos. ion. m/z: 371 (M+1).

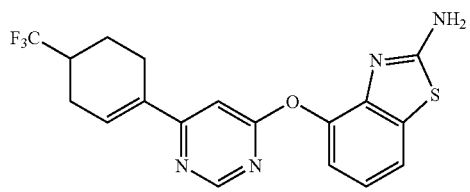

(e) 4-[6-(4-Trifluoromethyl-cyclohex-1-enyl)-pyrimidin-4-yloxy]-benzothiazol-2-ylamine. A mixture of 4-(6-iodo-pyrimidin-4-yloxy)-benzothiazol-2-ylamine, Example 1(d), (253 mg, 0.68 mmol), 4,4,5,5-tetramethyl-2-(4-trifluoromethyl-cyclohex-1-enyl)-[1,3,2]dioxaborolane, Example 1(b), (283 mg, 1.02 mmol), $PdCl_2(PPh_3)_2$ (48 mg, 0.07 mmol), and $Na_2CO_3$ (216 mg, 2.04 mmol) in DME/EtOH/$H_2O$ (2:1:2, 2.0 mL) was heated in a microwave synthesizer at 120° C. with stirring for 15 min. The reaction mixture was cooled to room temperature, diluted with water, and extracted with $CH_2Cl_2$. The combined organic layers were washed with brine, dried over $Na_2SO_4$, filtered, and evaporated in vacuo. The residue was purified by silica gel column chromatography (gradient: 0% to 4.0% MeOH/$CH_2Cl_2$) to give a yellow solid. The solid was suspended in MeOH, filtered, and washed with MeOH. The filter cake was dried in vacuo to give the title compound as a white solid. MS (ESI, pos. ion.) nz/z: 393 (M+1).

EXAMPLE 2

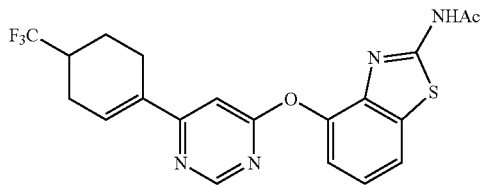

N-{4-[6-(4-Trifluoromethyl-cyclohex-1-enyl)-pyrimidin-4-yloxy]-benzothiazol-2-yl}-acetamide. To a suspension of 4-[6-(4-trifluoromethyl-cyclohex-1-enyl)-pyrimidin-4-yloxy]-benzothiazol-2-ylamine, Example 1(e), (85 mg, 0.22 mmol) in toluene was added acetic anhydride (82 μL, 0.86 mmol). The mixture was heated at 90° C. with stirring for 1 h. The reaction mixture was allowed to cool to room temperature and evaporated in vacuo to give the title compound as a white solid. MS (ESI, pos. ion.) m/z: 435 (M+1).

EXAMPLE 3

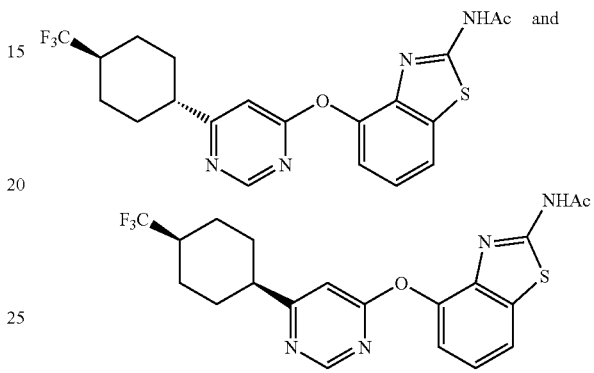

trans-N-{4-[6-(4-Trifluoromethyl-cyclohexyl)-pyrimidin-4-yloxy]-benzothiazol-2-yl}-acetamide and cis-N-{4-[6-(4-trifluoromethyl-cyclohexyl)-pyrimidin-4-yloxy]-benzothiazol-2-yl}-acetamide. To a mixture of N-{4-[6-(4-trifluoromethyl-cyclohex-1-enyl)-pyrimidin-4-yloxy]-benzothiazol-2-yl}-acetamide, Example 2, (94 mg, 0.22 mmol) and ammonium formate (272 mg, 4.32 mmol) in n-butanol (4 mL) was added palladium hydroxide (23 mg, 20 wt. % Pd on carbon, wet, Aldrich) at room temperature under nitrogen atmosphere. The reaction mixture was heated at 120° C. with stirring for 17 h, cooled to room temperature, filtered through Celite®, and washed with MeOH. The filtrates were combined and evaporated in vacuo. The residue was purified by silica gel column chromatography (gradient: 0-4% MeOH/$CH_2Cl_2$) to give the title compound as a 1:1.6 mixture of cis and trans isomers. MS (ESI, pos. ion) m/z: 437 (M+1).

EXAMPLE 4

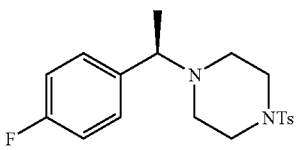

(a) 1-[(1R)-1-(4-Fluoro-phenyl)-ethyl]-4-(toluene-4-sulfonyl)-piperazine. A mixture of N,N-bis(2-chloroethyl)-p-toluenesulfonamide (tech. 90%, 46.8 g, 158 mmol, Lancaster) and (1R)-1-(4-fluorophenyl)ethanamine (20 g, 144 mmol, SynQuest) in N,N-diisopropylethylamine (50 mL) was heated at 125° C. with stirring under a nitrogen atmosphere for 18 h. The reaction mixture was allowed to cool to below 100° C. and a 7/3 mixture of EtOH/H₂O (120 mL) was added slowly with stirring. The mixture was left to reach room temperature and the stirring was continued for 2.5 h. The solid precipitate was filtered, and washed with H₂O (3×50 mL) and hexane (2×50 mL). The solids were dried in vacuo at 50° C. for 18 h, and stirred in 1:1 mixture of EtOH/H₂O (140 mL) for 75 min. The solid precipitate was filtered, washed with a 1:1 mixture of EtOH/H₂O (40 mL) and a 7:3 mixture of EtOH/H₂O (20 mL), and dried in vacuo at 50° C. for 6 h to give the title compound as an off-white solid. MS (ESI, pos. ion.) m/z: 363 (M+1).

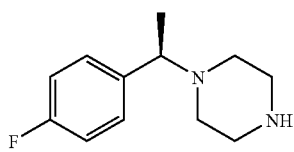

(b) 1-[(1R)-1-(4-Fluoro-phenyl)-ethyl]-piperazine. A mixture of 1-[(1R)-1-(4-fluoro-phenyl)-ethyl]-4-(toluene-4-sulfonyl)-piperazine, Example 4(a), (20 g, 55 mmol), 4-hydroxybenzoic acid (22.9 g, 166 mmol, Aldrich) and HBr solution in AcOH (33 wt %, 200 mL, Aldrich) was stirred at room temperature under nitrogen atmosphere for 48 h. Water (200 mL) was added slowly and the mixture was stirred for 2 h at room temperature. The solid precipitate was filtered and the filter cake was washed with H₂O (2×50 mL). The filtrate and the H₂O washes were combined and extracted with toluene (4×50 mL). The aqueous phase was cooled in an ice bath and treated portionwise with solid KOH (235 g) until pH>10. The aqueous solution was extracted with toluene (3×50 mL) and ethyl acetate (50 mL). The combined organic extracts were washed with brine (100 mL), dried over MgSO₄, filtered, and concentrated under reduced pressure. The reidue was dried in vacuo to yield the title compound as a pale-brown solid. MS (ESI, pos. ion.) nz/z: 209 (M+1).

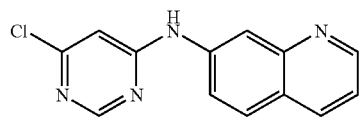

(c) (6-Chloropyrimidin-4-yl)-quinolin-7-yl-amine. A mixture of 4,6-dichloro-pyrimidine (1.04 g, 7.0 mmol, Lancaster), 7-aminoquinoline (1.00 g, 7.0 mmol, SynChem Inc.) and potassium carbonate (1.93 g, 14.0 mmol) in DMF (5.0 mL) was heated at 100° C. with stirring for 24 h. The reaction mixture was allowed to cool to room temperature, diluted with water, and the resulting solid precipitate was filtered. The filter cake was dissolved in a mixture of CH₂Cl₂ and MeOH (3:1), washed with water and brine, dried over Na₂SO₄, and filtered. The filtrate was evaporated under reduced pressure, and the brown-yellow solid residue was suspended in CH₂Cl₂, filtered, and washed with CH₂Cl₂. The filter cake was dried in vacuo to give the title compound as a light-yellow solid. MS (ESI, pos. ion.) m/z: 257 (M+1).

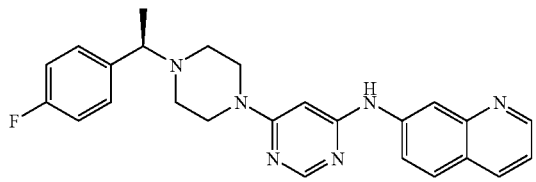

(d) (6-{4-[(1R)-1-(4-Fluorophenyl)-ethyl]-piperazin-1-yl}-pyrimidin-4-yl)-quinolin-7-yl-amine. To a mixture of (6-chloropyrimidin-4-yl)-quinolin-7-yl-amine, Example 4(c), (85 mg, 0.33 mmol) and 1-[(1R)-1-(4-fluorophenyl) ethyl]piperazine, Example 4(b), (103 mg, 0.49 mmol) in DMF (1.0 mL) was added potassium carbonate (68 mg, 0.49 mmol, Aldrich). The mixture was heated at 80° C. with stirring for 27 h, cooled to room temperature, diluted with water, and extracted with CH₂Cl₂. The combined organic extracts were washed with brine, dried over Na₂SO₄, filtered, and evaporated in vacuo. The residue was suspended in MeOH, filtered, and washed with MeOH. The filter cake was dried in vacuo to give the title compound as a light-yellow solid. M.p.: 206-207° C. MS (ESI, pos. ion.) m/z: 429 (M+1).

EXAMPLE 5

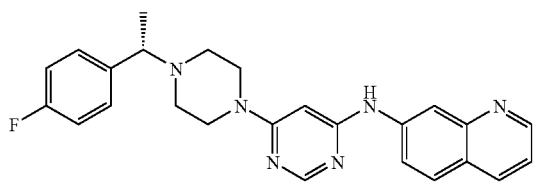

(6-{4-[(1S)-1-(4-Fluorophenyl)-ethyl]-piperazin-1-yl}-pyrimidin-4-yl)-quinolin-7-yl-amine. (6-Chloropyrimidin-4-yl)-quinolin-7-yl-amine, Example 4(c), (59 mg, 0.23 mmol) was reacted with 1-[(1S)-1-(4-fluorophenyl)ethyl] piperazine (57 mg, 0.27 mmol, prepared from (1S)-1-(4-fluorophenyl)ethylamine (SynQuest) according steps (a) and (b) of Example 4) under the conditions of Example 4(d) to give the title compound. M.p.: 206-207° C. MS (ESI, pos. ion.) m/z: 429 (M+1).

EXAMPLE 6

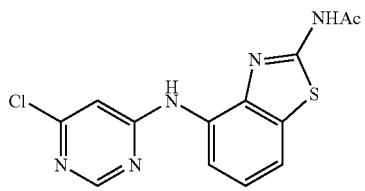

(a) N-[4-(6-Chloro-pyrimidin-4-ylamino)-benzothiazol-2-yl]-acetamide. A mixture of 4,6-dichloro-pyrimidine (87 mg, 0.58 mmol, Lancaster), N-(4-amino-benzothiazol-2-yl)-acetamide (0.121 g, 0.58 mmol, prepared according to the procedure described in WO03099284) and potassium carbonate (160 mg, 1.16 mmol, Aldrich) in DMF (1.0 mL)

was heated at 100° C. with stirring for 3 h. The reaction mixture was allowed to cool to room temperature, diluted with water, and extracted with CH$_2$Cl$_2$. The combined organic extracts were washed with brine, dried over Na$_2$SO$_4$, filtered, and concentrated under reduced pressure. The residue was suspended in CH$_2$Cl$_2$, filtered, and washed with CH$_2$Cl$_2$. The filter cake was dried in vacuo to give the title compound as a yellow solid. MS (ESI, pos. ion.) m/z: 320 (M+1).

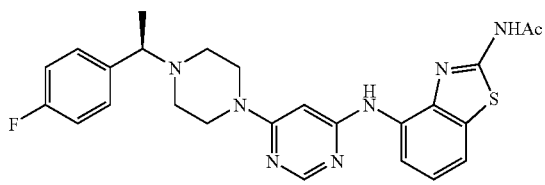

(b) N-[4-(6-{4-[(1R)-1-(4-Fluoro-phenyl)-ethyl]-piperazin-1-yl}-pyrimidin-4-ylamino)-benzothiazol-2-yl]-acetamide. N-[4-(6-Chloro-pyrimidin-4-ylamino)-benzothiazol-2-yl]-acetamide, Example 6(a), (76 mg, 0.24 mmol) was reacted with 1-[(1R)-1-(4-fluorophenyl)ethyl]piperazine, Example 4(b), (74 mg, 0.35 mmol) under the conditions of Example 4(d) to give the title product as a yellow solid. MS (ESI, pos. ion.) m/z: 492 (M+1).

EXAMPLE 7

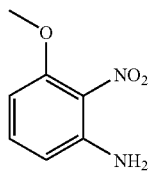

(a) 3-Methoxy-2-nitro-phenylamine. A mixture of 2-amino-3-nitrophenol (25.0 g, 162 mmol, Aldrich) and K$_2$CO$_3$ (27 g, 195 mmol) in DMF (65 ml) was stirred at room temperature for 1 h. Methyl iodide (12.2 mL, 195 mmol, Aldrich) was added and the reaction was stirred at room temperature for 30 h. The reaction was diluted with H$_2$O and extracted with EtOAc (3×). The combined organic layers were dried over Na$_2$SO$_4$, filtered and concentrated in vacuo. The dark-red solid was recrystallized from hexanes to yield the title compound as orange needles. MS (ESI, pos. ion.) m/z: 169 (M+1).

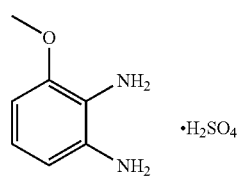

(b) 3-Methoxy-benzene-1,2-diamine sulfate. A mixture of 3-methoxy-2-nitro-phenylamine, Example 7(a), (4.6 g, 27 mmol), iron powder (10.7 g, 191 mmol, Aldrich), EtOH (130 mL) and H$_2$O (10 mL) was heated at 50° C. A solution of HCl (12 M, 1.7 mL) was added dropwise with stirring. The mixture was heated at reflux for 3 h and allowed to cool to room temperature. After neutralization with NaOH and filtration through Celite®, the solvent was removed in vacuo and the residue was partitioned between CH$_2$Cl$_2$ and sat. aq. NaHCO$_3$. After extraction with CH$_2$Cl$_2$ (3×), the combined organic layers were concentrated. The residue was re-dissolved in of EtOH (30 mL) and treated with concentrated H$_2$SO$_4$ until no more precipitate was formed. The resulting solid was removed by filtration, washed with EtOH and dried in vacuo for 20 h at room temperature to give the title compound as an off-white powder. MS (ESI, pos. ion.) m/z: 139 (M–HSO$_4^-$).

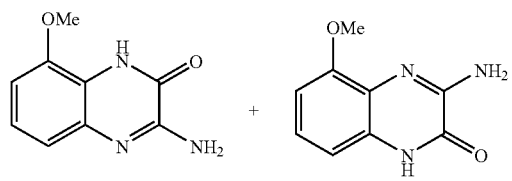

(c) 3-Amino-8-methoxy-1H-quinoxalin-2-one and 3-amino-5-methoxy-1H-quinoxalin-2-one. To a suspension of 3-methoxy-benzene-1,2-diamine sulfate, Example 7(b), (2.36 g, 10 mmol) in EtOH (15 mL) and H$_2$O (1 mL) was added NaHCO$_3$ (1.68 g, 20 mmol, J T Baker). When gas evolution was complete, ethoxy-imino-acetic acid ethyl ester (1.6 g, 11 mmol, prepared according to J. Chem. Soc. *Perkin. Trans.* 1, 1999, 1789) was added and the mixture was stirred at room temperature for 16 h. The reaction was diluted with sat. aq. NaHCO$_3$ and extracted with 25% i-PrOH/CHCl$_3$ (5×). The combined organic layers were dried over Na$_2$SO$_4$, filtered, and concentrated in vacuo. Purification by flash chromatography (gradient: 0-5% MeOH/CH$_2$Cl$_2$) afforded 3-amino-8-methoxy-1H-quinoxalin-2-one as a light-brown powder [MS (ESI, pos. ion.) m/z: 192 (M+1)] and 3-amino-5-methoxy-1H-quinoxalin-2-one as a light-brown powder [MS (ESI, pos. ion.) m/z: 192 (M+1)].

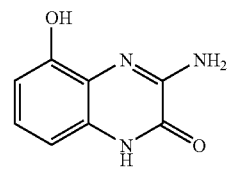

(d) 3-Amino-5-hydroxy-1H-quinoxalin-2-one. To a suspension of 3-amino-5-methoxy-1H-quinoxalin-2-one, Example 7(c), (0.47 g, 2.5 mmol) in benzene (25 mL) was added AlCl$_3$ (0.97 g, 7.4 mmol, Aldrich) and the mixture was heated to reflux with stirring for 2 h. The reaction mixture was allowed to cool to room temperature and quenched by careful addition of satd aq. NaHCO$_3$. The resulting mixture was extracted with 25% i-PrOH/CHCl$_3$ (5×). The combined organic extracts were dried over Na$_2$SO$_4$, filtered, and concentrated in vacuo to afford a brown powder. MS (ESI, pos. ion.) m/z: 178 (M+1).

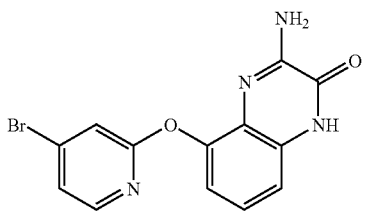

(e) 3-Amino-5-(4-bromo-pyridin-2-yloxy)-1H-quinoxalin-2-one. A mixture of 4-bromo-2-fluoropyridine (35 mg, 0.2 mmol, Asymchem), 3-amino-5-hydroxy-1H-quinoxalin-2-one, Example 7(d), (43 mg, 0.24 mmol) and cesium carbonate (98 mg, 0.3 mmol) in DMF (0.8 mL) was heated at 100° C. with stirring for 5 h. The reaction mixture was allowed to cool to room temperature and the solvent was evaporated in vacuo. The residue was purified by silica gel column chromatography (50% EtOAc/hexane) to give the title compound as a white solid. MS (ESI, pos. ion.) m/z: 335 (M+1).

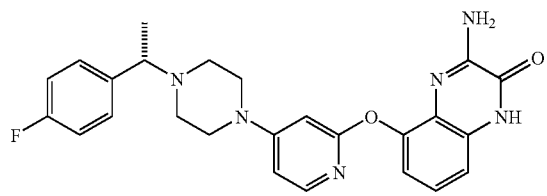

(f) 3-Amino-5-(4-{4-[(1S)-1-(4-fluoro-phenyl)-ethyl]-piperazin-1-yl}-pyridin-2-yloxy)-1H-quinoxalin-2-one. A mixture of 3-amino-5-(4-bromo-pyridin-2-yloxy)-1H-quinoxalin-2-one, Example 7(e), (17 mg, 0.05 mmol), 1-[(1S)-1-(4-fuoro-phenyl)-ethyl]-piperazine (20 mg, 0.1 mmol, prepared from (1S)-1-(4-fluorophenyl)ethylamine (SynQuest) according steps (a) and (b) of Example 4), diisopropylethylamine (13 uL, 0.08 mmol) and DMSO (1 mL) was heated in a microwave synthesizer at 150° C. for 10 min, then at 180° C. for 20 min. The reaction mixture was cooled to room temperature and partitioned between EtOAc and brine. The organic phase was separated, dried over Na$_2$SO$_4$, filtered and evaporated under reduced pressure. The residue was purified by thin layer chromatography (5% MeOH in CH$_2$Cl$_2$) to give the title compound. MS (ESI, pos. ion.) m/z: 461 (M+1).

EXAMPLES 8 AND 9

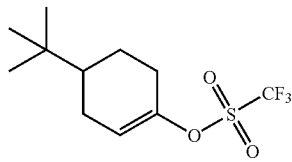

(a) Trifluoro-methanesulfonic acid 4-tert-butyl-cyclohex-1-enyl ester. To a solution of 4-tert-butylcyclohexanone (6.24 g, 40 mmol, Aldrich) in THF (100 mL) was added dropwise lithium bis(trimethylsilyl)amide (40 mL, 30 mmol, 1M solution in THF, Aldrich) over a period of 30 min with stirring at −78° C. The mixture was stirred for 1 h at −78° C., and a solution of N-phenyltrifluoromethanesulfonimide (14.28 g, 40 mmol, Aldrich) in THF (100 mL) was added dropwise with stirring over a period of 30 min. The reaction mixture was stirred at −78° C. for 2 h and slowly warmed to room temperature with stirring over a period of 6 h. The reaction mixture was extracted with EtOAc (3×).

The combined organic extracts were washed with water, dried over Na$_2$SO$_4$, and filtered. The filtrate was evaporated and the residue was purified by silica gel column chromatography (10% ethyl acetate/hexane) to give the title compound as an oil.

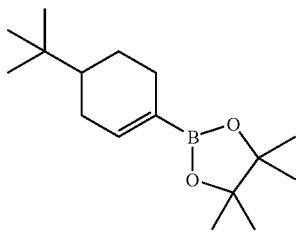

(b) 2-(4-tert-Butyl-cyclohex-1-enyl)-4,4,5,5-tetramethyl-[1,3,2]dioxaborolane. To a solution of trifluoro-methanesulfonic acid 4-tert-butyl-cyclohex-1-enyl ester, Example 8(a), (5.6 g, 21.2 mmol) in dioxane (100 mL) was added bis(pinacolato)diboron (5.6 g, 22 mmol, Aldrich), potassium acetate (6 g, 61 mmol), PdCl$_2$(dppf) (315 mg, 0.6 mmol, Strem) and dppf (332 mg, 0.6 mmol, Strem) under nitrogen atmosphere. The reaction mixture was heated at 80° C. with stirring for 18 h, allowed to cool to room temperature, and filtered through Celite®. The filtrate was evaporated in vacuo and the residue was purified by silica gel column chromatography (10% ethyl acetate/hexane) to give the title compound as a white amorphous solid. MS (ESI, pos. ion.) m/z: 265 (M+1).

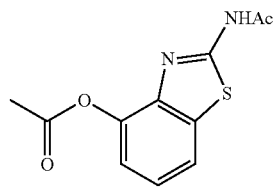

(c) Acetic acid 2-acetylamino-benzothiazol-4-yl ester. To the suspension of 2-amino-4-hydroxybenzothiazole (8.3 g, 50 mmol, Fluorochem Ltd.) in toluene (100 mL) was added acetic anhydride (47 mL, 500 mmol). The reaction mixture was heated at 110° C. for 16 h. The solvents were evaporated in vacuo to give the title compound as a tan solid. MS (ESI, pos. ion.) m/z: 251 (M+1).

(d) N-(4-Hydroxy-benzothiazol-2-yl)-acetamide. To the suspension of acetic acid 2-acetylamino-benzothiazol-4-yl ester, Example 8(c), (9.7 g, 39 mmol) in MeOH (200 mL) was added potassium carbonate (11 g, 78 mmol). The reaction mixture was stirred at 25° C. for 6 h, most of the solvent was evaporated in vacuo, and the residue was acidified with 10% HCl to pH 5. The mixture was then extracted with EtOAc (3×), the combined EtOAc extracts were washed with brine, dried over $Na_2SO_4$, filtered, and concentrated in vacuo to give the title compound as a tan solid. MS (ESI, pos. ion.) m/z: 209 (M+1).

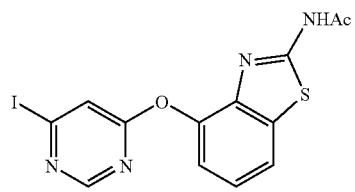

(e) N-[4-(6-Iodo-pyrimidin-4-yloxy)-benzothiazol-2-yl]-acetamide. A mixture of 4,6-diiodo-pyrimidine, Example 1(c), (724 mg, 2.18 mmol), 2 N-(4-hydroxy-benzothiazol-2-yl)-acetamide, Example 8(d), (426 mg, 2.05 mmol), and $K_2CO_3$ (425 mg, 3.07 mmol) in DMSO (3.0 mL) was heated at 80° C. with stirring for 1 h. The reaction mixture was allowed to cool to room temperature, diluted with water, and stirred for 18 h. The resulting precipitate was filtered, washed with water, and dried in vacuo to give a light-yellow solid. MS (ESI, pos. ion.) m/z: 413 (M+1).

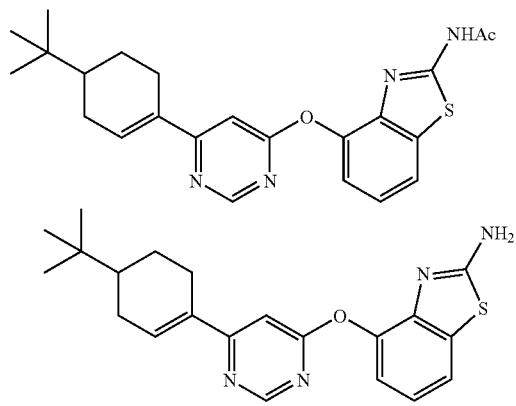

(f) N-{4-[6-(4-tert-Butyl-cyclohex-1-enyl)-pyrimidin-4-yloxy]-benzothiazol-2-yl}-acetamide and 4-[6-(4-tert-butyl-cyclohex-1-enyl)-pyrimidin-4-yloxy]-benzothiazol-2-ylamine. A mixture of N-[4-(6-iodo-pyrimidin-4-yloxy)-benzothiazol-2-yl]-acetamide, Example 8(e), (100 mg, 0.24 mmol), 2-(4-tert-butyl-cyclohex-1-enyl)-4,4,5,5-tetramethyl-[1,3,2]dioxaborolane, Example 8(b), (96 mg, 0.36 mmol), $PdCl_2(PPh_3)_2$ (17 mg, 0.02 mmol), and $Na_2CO_3$ (38 mg, 0.36 mmol) in $DME/EtOH/H_2O$ (2:1:2, 2.0 mL) was heated in a microwave at 120° C. with stirring for 15 min. The reaction mixture was cooled to room temperature, diluted with water, and extracted with $CH_2Cl_2$. The combined organic layers were washed with brine, dried over $Na_2SO_4$, filtered, and evaporated in vacuo. The residue was purified by silica gel column chromatography with eluent $MeOH/CH_2Cl_2$ (1:80) and with eluent $MeOH/CH_2Cl_2$ (1:50) to give N-{4-[6-(4-tert-butyl-cyclohex-1-enyl)-pyrimidin-4-yloxy]-benzothiazol-2-yl}-acetamide [M.p.: >200° C. (dec.); MS (ESI, pos. ion.) m/z: 423 (M+1)] and 4-[6-(4-tert-butyl-cyclohex-1-enyl)-pyrimidin-4-yloxy]-benzothiazol-2-ylamine [M.p.: 208.3-208.8° C.; MS (ESI, pos. ion.) m/z: 381 (M+1)].

EXAMPLE 10

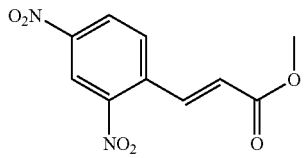

(a) Methyl-3-(2,4-dinitrophenyl)acrylate. A solution of 2,4-dinitrobenzaldehyde (3.292 g, 16.79 mmol, Aldrich) and methyl (triphenylphosphoranylidene)acetate (5.615 g, 16.79 mmol, Aldrich) in benzene (65 mL) was heated to reflux for 4 h. The reaction mixture was allowed to cool to room temperature and evaporated under reduced pressure. The residue was participated between EtOAc (300 mL) and water (100 mL). The EtOAc layer was separated, washed with brine (100 mL), dried over anhydrous sodium sulfate, filtered and concentrated to yield a yellowish-brown solid. This solid was dissolved in $Et_2O$ (100 mL) and the solution was filtered. The filtrate was evaporated under reduced pressure and the residue was purified by silica gel column chromatography (gradient: 0-10% EtOAc/hexane to give the title compound as pale-yellow amorphous solid. MS (ESI, pos. ion.) m/z: 253 (M+1).

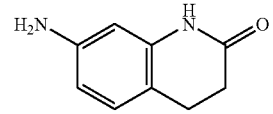

(b) 7-Amino-3,4-dihydroquinolin-2(1H)-one. To a solution of methyl-3-(2,4-dinitrophenyl)acrylate from step (a) above (4.3 g, 117 mmol) in EtOH (75 mL) and acetic acid (8 mL) was added 10% Pd/C (1.4 g) and the mixture was shaken under hydrogen atmosphere (60 psi) on a Parr shaker for 6 h. The catalyst was filtered through a Celite® pad and the filter cake was washed with EtOH (2×35 mL). The combined filtrates were concentrated and the residue dried under vacuo to give the title compound as a yellowish-brown solid. MS (ESI, pos. ion.) m/z: 163 (M+1).

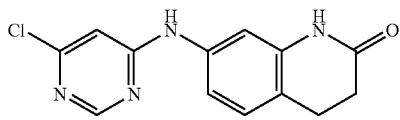

(c) 7-(6-Chloropyrimidin-4-ylamino)-3,4-dihydroquinolin-2(1H)-one. A mixture of 7-amino-3,4-dihydroquinolin-2(1H)-one from step (b) above (0.4 g, 2.47 mmol), 4,6-dichloropyrimidine (0.33 g, 2.22 mmol, Aldrich) and diisopropylethylamine (0.7 mL, 4.02 mmol) in EtOH (2.8 mL) was heated in a microwave synthesizer at 110° C. for 6 min. The reaction mixture was cooled to room temperature and diluted with MeOH (3 mL). The solid precipitate was filtered and dried under vacuo to give the title compound as pale-yellow amorphous solid. MS (ESI, pos. ion.) m/z: 275 (M+1).

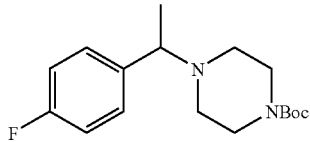

(d) 4-[1-(4-Fluoro-phenyl)-ethyl]-piperazine-1-carboxylic acid tert-butyl ester. To a solution of piperazine-1-carboxylic acid tert-butyl ester (0.39 g, 2.2 mmol, Fluka) and 4-fluoro-acetophenone (0.39 mL, 3.3 mmol, Aldrich) in THF (2 mL) was added titanium(IV) isopropoxide (1.9 mL, 6.6 mmol, Aldrich) and the mixture was stirred at 75° C. for 18 h under nitrogen atmosphere. The reaction mixture was cooled to −48° C. and treated with NaBH(OAc)$_3$ (1.23 g, 6.44 mmol, Aldrich) and methanol (1 mL). The mixture was allowed to warm to room temperature over 3.5 h and diluted with EtOAc (100 mL). The EtOAc solution was washed with aqueous NaOH (1N, 3×100 mL). The organic layer was separated, dried over Na$_2$SO$_4$, filtered, and concentrated in vacuo. The residue was purified by silica gel column chromatography (gradient: 04% MeOH/CH$_2$Cl$_2$) to give the title compound as a yellow oil. MS (ESI, pos. ion.) m/z: 309.2 (M+1).

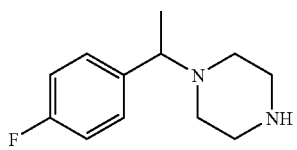

(e) 1-[1-(4-Fluoro-phenyl)-ethyl]-piperazine. To a solution of 4-[1-(4-fluoro-phenyl)-ethyl]-piperazine-1-carboxylic acid tert-butyl ester, from step (d) above (0.42 g, 1.36 mmol) in CH$_2$Cl$_2$ (5 mL) was added TFA (0.5 mL, 6.5 mmol, Aldrich) dropwise with stirring at 0° C. The reaction mixture was stirred at room temperature for 18 h and evaporated under reduced pressure. The residue was dried in vacuo to give the crude title compound, which was used in the next step without additional purification.

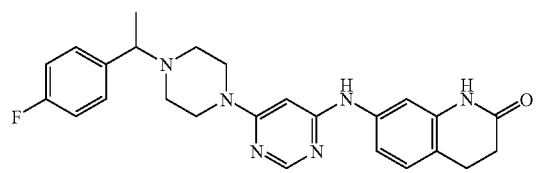

(f) 7-(6-(4-(1-(4-Fluorophenyl)ethyl)piperazin-1-yl)pyrimidin-4-ylamino)-3,4-dihydroquinolin-2(1H)-one. A mixture of 7-(6-chloropyrimidin-4-ylamino)-3,4-dihydroquinolin-2(1H)-one from step (c) above (0.117 g, 0.43 mmol), 1-(1-(4-fluorophenyl)ethyl)piperazine from step (e) above (0.090 g, 0.43 mmol) and diisopropylethylamine (0.15 mL, 0.86 mmol) in EtOH (2.5 mL) was heated in a microwave synthesizer at 170° C. for 6 min. The reaction mixture was cooled to room temperature and the solvent was evaporated under reduced pressure. To the residue was added 5:1 mixture of MeOH/DMSO (4 mL) and the precipitate was collected by filtration. The filter cake was separated and dried under vacuo to give the title compound as off-white amorphous solid. MS (ESI, pos. ion.) m/z: 447 (M+1).

EXAMPLE 11

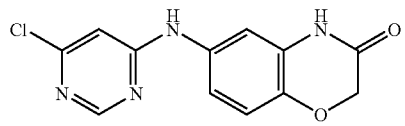

(a) 6-(6-Chloropyrimidin-4-ylamino)-2H-benzo[b][1,4]oxazin-3(4H)-one. 6-Amino-2H-benzo[b][1,4]oxazin-3(4H)-one (0.336 g, 2.05 mmol, Bionet Research) was reacted with 4,6-dichloropyrimidine (0.305 g, 2.05 mmol, Aldrich) under the conditions of Example 1(c) to give the title compound as pale-yellow amorphous solid. MS (ESI, pos. ion.) m/z: 277 (M+1).

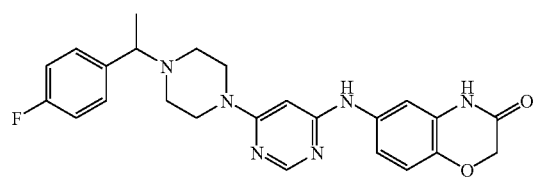

(b) 6-(6-(4-(1-(4-Fluorophenyl)ethyl)piperazin-1-yl)pyrimidin-4-ylamino)-2benzo[b][1,4]oxazin-3(4H)-one. 6-(6-Chloropyrimidin-4-ylamino)-2H-benzo[b][1,4]oxazin-3 (4H)-one from step (a) above (0.112 g, 0.41 mmol) was reacted with 1-(1-(4-fluorophenyl)ethyl)piperazine, Example 10(e), (0.086 g, 0.41 mmol) under the conditions of Example 10(d). The crude product was purified by preparative HPLC [gradient 10-90% MeCN (0.1% TFA)/H$_2$O (0.1% TFA)] to give the desired product as a TFA salt. The salt was dissolved in DCM (25 mL) and neutralized with sat. NaHCO$_3$ (5 mL). The DCM layer was separated, dried over anhydrous sodium sulfate, and filtered. The filtrate was evaporated and the residue was dried in vacuo to give the title compound as amorphous white solid. MS (ESI, pos. ion) m/z: 449 (M+1).

EXAMPLE 12

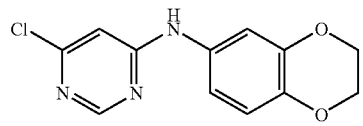

(a) 6-Chloro-N-(2,3-dihydrobenzo[b][1,4]dioxin-6-yl)pyrimidin-4-amine. A solution of 2,3-dihydrobenzo[b][1,4]dioxin-6-amine (0.532 g, 3.52 mmol, Aldrich) and 4,6-dichloropyrimidine (0.528 g, 3.54 mmol, Aldrich) in EtOH (2.5 mL) was stirred with PS-DIEA resin (1.512 g, 5.63 mmol, 3.72 mmol/g, Argonaut) at room temperature for 2 h and then heated in a microwave synthesizer at 160° C. for 6 min. The reaction mixture was cooled to room temperature and the resin was removed by filtration. The resin was washed with methanol (10 mL) and the combined filtrate was evaporated under reduced pressure. The gummy residue was purified by silica gel column chromatography (gradient: 0-10% MeOH/DCM) to afford the title compound as pale-yellow amorphous solid. MS (ESI, pos. ion.) m/z: 264 (M+1).

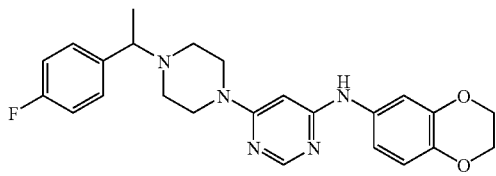

(b) N-(2,3-Dihydrobenzo[b][1,4]dioxin-6-yl)-6-(4-(1-(4-fluorophenyl)ethyl)piperazin-1-yl)pyrimidin-4-amine. 6-Chloro-N-(2,3-dihydrobenzo[b][1,4]dioxin-6-yl)pyrimidin-4-amine from step (a) above (0.167 g, 0.63 mmol) was reacted with 1-(1-(4-fluorophenyl)ethyl)piperazine, Example 10(e), (0.135 g, 0.65 mmol) in EtOH (3.0 mL) under the conditions of Example 11(b) to give the title compound as amorphous off-white solid. MS (ESI, pos. ion.) m/z: 436 (M+1).

EXAMPLE 13

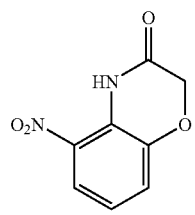

(a) 5-Nitro-2H-benzo[b][1,4]oxazin-3(4H)-one. A mixture of 2-amino-3-nitrophenol (0.776 g, 5.04 mmol, Aldrich) and ethyl bromoacetate (1.56 mL, 14.03 mmol, Aldrich) in diisopropylethylamine (1.25 mL, 7.15 mmol) was heated in a microwave synthesizer at 150° C. for 10 min. The reaction mixture was cooled to room temperature and evaporated under reduced pressure. The residue was purified by silica gel column chromatography (gradient: 0-10% MeOH/DCM) to afford the title compound as pale-yellow amorphous solid. MS (ESI, pos. ion.) m/z: 195 (M+1).

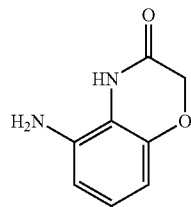

(b) 5-Amino-2H-benzo[b][1,4]oxazin-3(4H)-one. To a solution of 5-nitro-2H-benzo[b][1,4]oxazin-3(4H)-one from step (a) above (0.915 g, 4.71 mmol) in EtOH (100 mL) was added 10% Pd/C (0.34 g) and the mixture was shaken under hydrogen atmosphere (45 psi) on a Parr shaker for 18 h. The catalyst was filtered through a Celite® pad and the filter cake was washed with EtOH (2×35 mL). The combined filtrates were evaporated under reduced pressure and the residue was dissolved in MeOH (25 mL). The solution was cooled to −5° C. in a freezer overnight and the precipitate was collected by filtration. The filter cake was separated and dried under vacuo to give the title compound as a white amorphous solid. MS (ESI, pos. ion.) m/z: 165 (M+1).

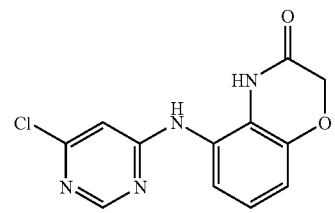

(c) 5-(6-Chloropyrimidin-4-ylamino)-2H-benzo[b][1,4]oxazin-3(4H)-one. A mixture of 5-amino-2H-benzo[b][1,4]oxazin-3(4H)-one from step (b) above (0.168 g, 1.02 mmol), 4,6-dichloropyrimidine (0.155 g, 1.04 mmol, Aldrich) and diisopropylethylamine (0.36 mL, 2.07 mmol) in 3:1 mixture of EtOH/NMP (4 mL) was heated in a microwave synthesizer at 150° C. for 6 min. The reaction mixture was cooled to room temperature and filtered to remove the insoluble solid. The filtrate was evaporated under reduced pressure. The reddish-brown residue was purified by silica gel column chromatography (gradient: 0-10% MeOH/DCM) to afford the title compound as pale-yellow amorphous solid. MS (ESI, pos. ion) nz/z: 277 (M+1).

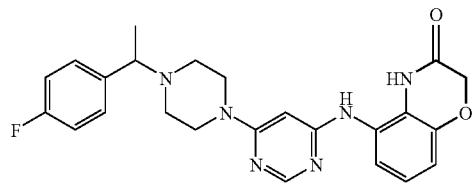

(d) 5-(6-(4-(1-(4-Fluorophenyl)ethyl)piperazin-1-yl)pyrimidin-4-ylamino)-2H-benzo[b][1,4]oxazin-3(4H)-one. 5-(6-Chloropyrimidin-4-ylamino)-2H-benzo-[b][1,4]oxazin-3(4H)-one from step (c) above (0.093 g, 0.34 mmol) was reacted with 1-(1-(4-fluorophenyl)ethyl)piperazine, Example 10(e), (0.079 g, 0.38 mmol) under the conditions of Example 13(c) to give the title compound as light-yellow amorphous solid. MS (ESI, pos. ion.) m/z: 449 (M+1).

EXAMPLE 14

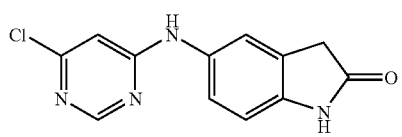

(a) 5-(6-Chloropyrimidin-4-ylamino)indolin-2-one. 4,6-Dichloropyrimidine (149 mg, 1 mmol, Aldrich) in EtOH (5 mL) was reacted with 5-aminoindolin-2-one (150 mg, 1 mmol, Combi Blocks) under the conditions of Example 10(c) to give the title compound as a pale-yellow oil. MS (ESI, pos. ion.) m/z: 261 (M+1).

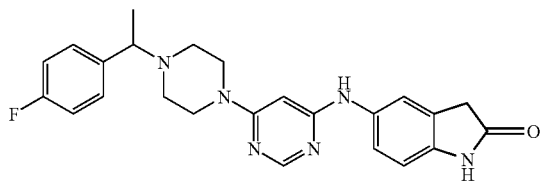

(b) 5-(6-(4-(1-(4-Fluorophenyl)ethyl)piperazin-1-yl)pyrimidin-4-ylamino)indolin-2-one. A mixture of 5-(6-chloropyrimidin-4-ylamino)indolin-2-one from step (a) above (65 mg, 0.25 mmol) and 1-(1-(4-fluorophenyl)ethyl)piperazine, Example 10(e), (63 mg, 0.3 mmol) in DMSO (2 mL) was heated in a microwave synthesizer at 170° C. for 5 min. The reaction mixture was cooled to room temperature and evaporated in vacuo. The residue was purified by silica gel column chromatography (gradient: 2-10% MeOH/DCM) to give the title compound as a pale-yellow solid. MS (ESI, pos. ion.) m/z: 433.2 (M+1).

EXAMPLE 15

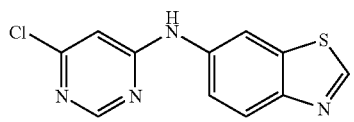

(a) N-(6-Chloropyrimidin-4-yl)benzo[d]thiazol-6-amine. 4,6-Dichloropyrimidine (148 mg, 1 mmol, Aldrich) was reacted with benzo[d]thiazol-6-amine (150 mg, 1 mmol, Aldrich) under the conditions of Example 12(a) to give the title compound. MS (ESI, pos. ion.) m/z: 263(M+1).

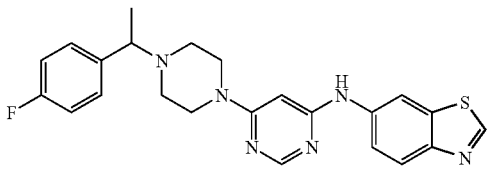

(b) N-(6-(4-(1-(4-Fluorophenyl)ethyl)piperazin-1-yl)pyrimidin-4-yl)benzo[d]thiazol-6-amine. A mixture of N-(6-chloropyrimidin-4-yl)benzo[d]thiazol-6-amine from step (a) above (60 mg, 0.22 mmol), 1-(1-(4-fluorophenyl)ethyl) piperazine, Example 10(e), (55 mg, 0.26 mmol) and PS-DIEA resin (0.25 g, 3.3 mmol/g, Argonaut Technologies) in EtOH (5 mL) was heated in a microwave synthesizer at 150° C. for 5 min. The reaction mixture was cooled to room temperature, filtered from the resin, and the filter cake was washed with MeOH and DCM. The combined filtrates were evaporated under reduced pressure and the residue was purified by silica gel column chromatography (gradient: 2-10% MeOH/DCM) to give the title compound as an oil. MS (ESI, pos. ion.) m/z: 435.2 (M+1).

EXAMPLE 16

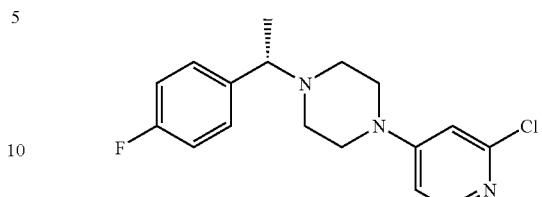

(a) (S)-1-(2-Chloropyridin-4-yl)-4-(1-(4-fluorophenyl) ethyl)piperazine. A mixture of 1-[(1S)-1-(4-fluoro-phenyl)-ethyl]-piperazine (208 mg, 1.0 mmol, prepared from (1S)-1-(4-fluorophenyl)ethylamine (SynQuest) according steps (a) and (b) of Example 4), 2-chloro-4-iodo-pyridine (240 mg, 1.0 mmol, Lancaster), $Pd_2(dba)_3$ (5 mg, 0.001 mmol. Strem) and t-BuONa (135 mg, 1.4 mmol, Aldrich) in toluene (5 mL) was stirred at 80° C. for 18 h under $N_2$ atmosphere. The reaction mixture was allowed to cool to room temperature, diluted with water (10 mL) and extracted with EtOAc (2×20 mL). The combined organic extracts were dried over $Na_2SO_4$, filtered and evaporated in vacuo. The residue was purified by silica gel column chromatography (20% EtOAc/hexane) to give the desired product as a gum. MS (ESI, pos. ion.) m/e: 320 (M+1).

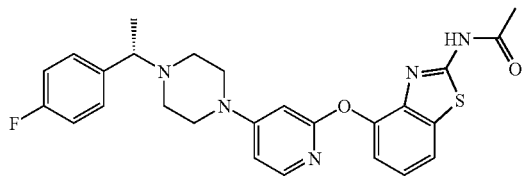

(b) (S)-N-(4-(4-(4-(1-(4-Fluorophenyl)ethyl)piperazin-1-yl) pyridin-2-yloxy)benzo[d]thiazol-2-yl)acetamide. A mixture of (S)-1-(2-chloro-pyridin-4-yl)-4-[1-(4-fluoro-phenyl)-ethyl]-piperazine from step (a) above (62 mg, 0.2 mmol), N-(4-hydroxy-benzothiazol-2-yl)-acetamide, Example 8(d), (62 mg, 0.3 mmol), CuI (38 mg, 0.2 mmol, Aldrich) and $K_2CO_3$ (55 mg, 0.4 mmol) in DMF (1 mL) was heated in a microwave synthesizer at 220° C. for 15 min. The reaction mixture was cooled to room temperature and partitioned between EtOAc and sat. $NH_4Cl$. The organic phase was separated, dried over $Na_2SO_4$ and filtered. The filtrate was evaporated in vacuo and the residue was purified by silica gel column chromatography, eluting with 10% MeOH/EtOAc to give the desired product mixed with a side product resulting from a reaction of N-deacetylation. The mixture was dissolved in $CH_2Cl_2$ (1 mL), and to the solution was added DMAP (10 mg, Aldrich) and $Ac_2O$ (0.05 mL, Aldrich). The solution was stirred at room temperature for 4 h and evaporated in vacuo. The residue was purified by silica gel column chromatography (10% MeOH/EtOAc) to give the desired product as a gum. MS (ESI, pos. ion.) m/e: 492 (M+1).

EXAMPLE 17

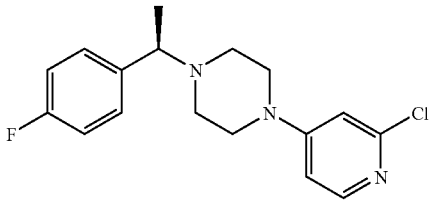

(a) (R)-1-(2-Chloropyridin-4-yl)-4-(1-(4-fluorophenyl)ethyl)piperazine. 1-[(1R)-1-(4-Fluoro-phenyl)-ethyl]-piperazine, Example 4(b), (208 mg, 1.0 mmol) was reacted with 2-chloro-4-iodo-pyridine (240 mg, 1.0 mmol, Lacaster) under the conditions of Example 16(a) to give the title compound as a gum. MS (ESI, pos. ion.) m/e: 320 (M+1)

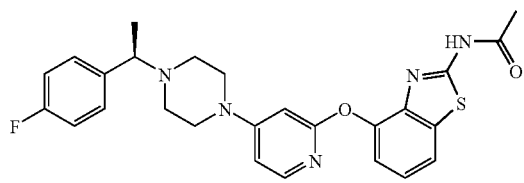

(b) (R)—N-(4-(4-(4-(1-(4-Fluorophenyl)ethyl)piperazin-1-yl)pyridin-2-yloxy)benzo[d]thiazol-2-yl)acetamide. 1-(2-Chloro-pyridin-4-yl)-4-[1-(4-fluoro-phenyl)-ethyl]-piperazine from step (a) above (62 mg, 0.2 mmol) was reacted with N-(4-hydroxy-benzothiazol-2-yl)-acetamide, Example 8(d), (62 mg, 0.3 mmol) under the conditions of Example 16(b) to give the desired product as a gum. MS (ESI, pos. ion.) m/e: 492 (M+1).

EXAMPLE 18

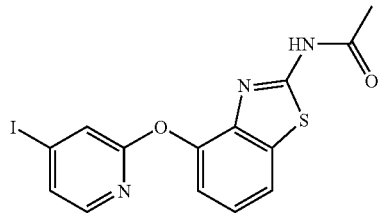

(a) N-(4-(4-Iodopyridin-2-yloxy)benzo[d]thiazol-2-yl)acetamide. To a solution of N-(4-hydroxy-benzothiazol-2-yl)-acetamide, Example 8(d), (4.68 g, 22 mmol) in DMF (30 mL) was added sodium hydride (60% in mineral oil, 0.96 g, 24 mmol) in small portions with stirring under nitrogen. The reaction mixture was stirred at room temperature for 10 min and 2-fluoro-4-iodopyridine (3.35 g, 15 mmol, Asymchem) was added in one portion. The reaction mixture was heated at 160° C. with stirring for 3 h. After cooling to room temperature, the mixture was diluted with water, and extracted with EtOAc (3×). The combined organic extracts were washed with brine, dried over $Na_2SO_4$, filtered, and evaporated in vacuo. The residue was purified by silica gel column chromatography (gradient 10-20% EtOAc/hexane) give the title compound as a white solid. MS (ESI, pos. ion.) m/z: 412 (M+1).

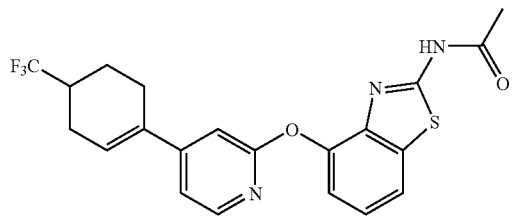

(b) N-(4-(4-(4-(Trifluoromethyl)Cyclohex-1-enyl)pyridin-2-yloxy)benzo[d]thiazol-2-yl)acetamide. A mixture of N-(4-(4-iodopyridin-2-yloxy)benzo[d]thiazol-2-yl)acetamide from step (a) above (0.25 g, 0.6 mmol), 4,4,5,5-tetramethyl-2-(4-trifluoromethyl-cyclohex-1-enyl)-[1,3,2]dioxaborolane, Example 1(b), (0.25 g, 0.9 mmol) and sodium carbonate (95 mg, 0.9 mmol) in DME (1.4 mL), EtOH (0.4 mL) and water (0.6 mL) was purged with nitrogen for 5 min. Dichlorobis(triphenylphosphine)palladium(II) (42 mg, 0.06 mmol) was added and the mixture was heated at 80° C. with stirring for 1.5 h under nitrogen. After cooling to room temperature, the reaction mixture was filtered through a pad of Celite® and the filtrate evaporated under reduced pressure. The residue was purified by silica gel column chromatography (gradient: 10-30% EtOAc/hexane) to give the title compound as a white solid. MS (ESI, pos. ion.) m/z: 434 (M+1). Other compounds included in this invention that can be made using the above methods and procedures are set forth below in Tables 1-5.

TABLE 1

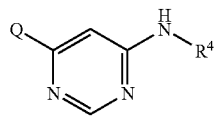

| Ex # | Q | $R^4$ |
|---|---|---|
| 20 | 4-(trifluoromethyl)-1-cyclohexen-1-yl | 2-(acetylamino)-1,3-benzothiazol-4-yl |
| 21 | 4-(trifluoromethyl)cyclohexyl | 2-(acetylamino)-1,3-benzothiazol-4-yl |
| 22 | 1-[1-(4-fluoro-phenyl)-ethyl]-1,2,3,6-tetrahydro-pyridin-4-yl | 2-(acetylamino)-1,3-benzothiazol-4-yl |

TABLE 1-continued

| Ex # | Q | R⁴ |
|---|---|---|
| 23 | 1-[1-(4-fluoro-phenyl)-ethyl]-piperidin-4-yl | 2-(acetylamino)-1,3-benzothiazol-4-yl |
| 24 | ((2,4-difluorophenyl)ethyl)-1-piperazinyl | 2-(amino)-1,3-benzothiazol-4-yl |
| 25 | ((2-fluorophenyl)ethyl)-1-piperazinyl | 2-(amino)-1,3-benzothiazol-4-yl |
| 26 | ((3-fluorophenyl)ethyl)-1-piperazinyl | 2-(amino)-1,3-benzothiazol-4-yl |
| 27 | ((4-bromophenyl)ethyl)-1-piperazinyl | 2-(amino)-1,3-benzothiazol-4-yl |
| 28 | ((4-chlorophenyl)ethyl)-1-piperazinyl | 2-(amino)-1,3-benzothiazol-4-yl |
| 29 | ((4-fluorophenyl)ethyl)-1-piperazinyl | 2-(amino)-1,3-benzothiazol-4-yl |
| 30 | ((4-fluorophenyl)propyl)-3-methyl-1-piperazinyl | 2-(amino)-1,3-benzothiazol-4-yl |
| 31 | ((4-trifluoromethyl)phenyl)ethyl)-1-piperazinyl | 2-(amino)-1,3-benzothiazol-4-yl |
| 32 | 4-(1,1-dimethylethyl)-1-cyclohexen-1-yl | 2-(amino)-1,3-benzothiazol-4-yl |
| 33 | 4-(1,1-dimethylethyl)-1-cyclohexyl | 2-(amino)-1,3-benzothiazol-4-yl |
| 34 | 4-(trifluoromethyl)-1-cyclohexen-1-yl | 2-(amino)-1,3-benzothiazol-4-yl |
| 35 | 4-(trifluoromethyl)cyclohexyl | 2-(amino)-1,3-benzothiazol-4-yl |
| 36 | 1-[1-(4-fluoro-phenyl)-ethyl]-1,2,3,6-tetrahydro-pyridin-4-yl | 2-(amino)-1,3-benzothiazol-4-yl |
| 37 | 1-[1-(4-fluoro-phenyl)-ethyl]-piperidin-4-yl | 2-(amino)-1,3-benzothiazol-4-yl |
| 38 | ((2,4-difluorophenyl)ethyl)-1-piperazinyl | 2-aminoquinolin-8-yl |
| 39 | ((2-fluorophenyl)ethyl)-1-piperazinyl | 2-aminoquinolin-8-yl |
| 40 | ((3-fluorophenyl)ethyl)-1-piperazinyl | 2-aminoquinolin-8-yl |
| 41 | ((4-bromophenyl)ethyl)-1-piperazinyl | 2-aminoquinolin-8-yl |
| 42 | ((4-chlorophenyl)ethyl)-1-piperazinyl | 2-aminoquinolin-8-yl |
| 43 | ((4-fluorophenyl)ethyl)-1-piperazinyl | 2-aminoquinolin-8-yl |
| 44 | ((4-fluorophenyl)propyl)-3-methyl-1-piperazinyl | 2-aminoquinolin-8-yl |
| 45 | ((4-trifluoromethyl)phenyl)ethyl)-1-piperazinyl | 2-aminoquinolin-8-yl |
| 46 | 4-(1,1-dimethylethyl)-1-cyclohexen-1-yl | 2-aminoquinolin-8-yl |
| 47 | 4-(1,1-dimethylethyl)-1-cyclohexyl | 2-aminoquinolin-8-yl |
| 48 | 4-(trifluoromethyl)-1-cyclohexen-1-yl | 2-aminoquinolin-8-yl |
| 49 | 4-(trifluoromethyl)cyclohexyl | 2-aminoquinolin-8-yl |
| 50 | 1-[1-(4-fluoro-phenyl)-ethyl]-1,2,3,6-tetrahydro-pyridin-4-yl | 2-aminoquinolin-8-yl |
| 51 | 1-[1-(4-fluoro-phenyl)-ethyl]-piperidin-4-yl | 2-aminoquinolin-8-yl |
| 52 | ((2,4-difluorophenyl)ethyl)-1-piperazinyl | 3,4-dihydro-2(1H)-quinoxalinone-5-yl |
| 53 | ((2-fluorophenyl)ethyl)-1-piperazinyl | 3,4-dihydro-2(1H)-quinoxalinone-5-yl |
| 54 | ((3-fluorophenyl)ethyl)-1-piperazinyl | 3,4-dihydro-2(1H)-quinoxalinone-5-yl |
| 55 | ((4-bromophenyl)ethyl)-1-piperazinyl | 3,4-dihydro-2(1H)-quinoxalinone-5-yl |
| 56 | ((4-chlorophenyl)ethyl)-1-piperazinyl | 3,4-dihydro-2(1H)-quinoxalinone-5-yl |
| 57 | ((4-fluorophenyl)ethyl)-1-piperazinyl | 3,4-dihydro-2(1H)-quinoxalinone-5-yl |
| 58 | ((4-fluorophenyl)propyl)-3-methyl-1-piperazinyl | 3,4-dihydro-2(1H)-quinoxalinone-5-yl |
| 59 | ((4-trifluoromethyl)phenyl)ethyl)-1-piperazinyl | 3,4-dihydro-2(1H)-quinoxalinone-5-yl |
| 60 | 4-(1,1-dimethylethyl)-1-cyclohexen-1-yl | 3,4-dihydro-2(1H)-quinoxalinone-5-yl |
| 61 | 4-(1,1-dimethylethyl)-1-cyclohexyl | 3,4-dihydro-2(1H)-quinoxalinone-5-yl |
| 62 | 4-(trifluoromethyl)-1-cyclohexen-1-yl | 3,4-dihydro-2(1H)-quinoxalinone-5-yl |
| 63 | 4-(trifluoromethyl)cyclohexyl | 3,4-dihydro-2(1H)-quinoxalinone-5-yl |
| 64 | 1-[1-(4-fluoro-phenyl)-ethyl]-1,2,3,6-tetrahydro-pyridin-4-yl | 3,4-dihydro-2(1H)-quinoxalinone-5-yl |
| 65 | 1-[1-(4-fluoro-phenyl)-ethyl]-piperidin-4-yl | 3,4-dihydro-2(1H)-quinoxalinone-5-yl |
| 66 | ((2,4-difluorophenyl)ethyl)-1-piperazinyl | 3-amino-1H-quinoxalin-2-one-5-yl |
| 67 | ((2-fluorophenyl)ethyl)-1-piperazinyl | 3-amino-1H-quinoxalin-2-one-5-yl |
| 68 | ((3-fluorophenyl)ethyl)-1-piperazinyl | 3-amino-1H-quinoxalin-2-one-5-yl |
| 69 | ((4-bromophenyl)ethyl)-1-piperazinyl | 3-amino-1H-quinoxalin-2-one-5-yl |
| 70 | ((4-chlorophenyl)ethyl)-1-piperazinyl | 3-amino-1H-quinoxalin-2-one-5-yl |
| 71 | ((4-fluorophenyl)ethyl)-1-piperazinyl | 3-amino-1H-quinoxalin-2-one-5-yl |
| 72 | ((4-fluorophenyl)propyl)-3-methyl-1-piperazinyl | 3-amino-1H-quinoxalin-2-one-5-yl |
| 73 | ((4-trifluoromethyl)phenyl)ethyl)-1-piperazinyl | 3-amino-1H-quinoxalin-2-one-5-yl |
| 74 | 4-(1,1-dimethylethyl)-1-cyclohexen-1-yl | 3-amino-1H-quinoxalin-2-one-5-yl |
| 75 | 4-(1,1-dimethylethyl)-1-cyclohexyl | 3-amino-1H-quinoxalin-2-one-5-yl |
| 76 | 4-(trifluoromethyl)-1-cyclohexen-1-yl | 3-amino-1H-quinoxalin-2-one-5-yl |
| 77 | 4-(trifluoromethyl)cyclohexyl | 3-amino-1H-quinoxalin-2-one-5-yl |
| 78 | 1-[1-(4-fluoro-phenyl)-ethyl]-1,2,3,6-tetrahydro-pyridin-4-yl | 3-amino-1H-quinoxalin-2-one-5-yl |
| 79 | 1-[1-(4-fluoro-phenyl)-ethyl]-piperidin-4-yl | 3-amino-1H-quinoxalin-2-one-5-yl |
| 80 | ((2,4-difluorophenyl)ethyl)-1-piperazinyl | 3-isoquinolinol-8-yl |

TABLE 1-continued

| Ex # | Q | R⁴ |
|---|---|---|
| 81 | ((2-fluorophenyl)ethyl)-1-piperazinyl | 3-isoquinolinol-8-yl |
| 82 | ((3-fluorophenyl)ethyl)-1-piperazinyl | 3-isoquinolinol-8-yl |
| 83 | ((4-bromophenyl)ethyl)-1-piperazinyl | 3-isoquinolinol-8-yl |
| 84 | ((4-chlorophenyl)ethyl)-1-piperazinyl | 3-isoquinolinol-8-yl |
| 85 | ((4-fluorophenyl)ethyl)-1-piperazinyl | 3-isoquinolinol-8-yl |
| 86 | ((4-fluorophenyl)propyl)-3-methyl-1-piperazinyl | 3-isoquinolinol-8-yl |
| 87 | ((4-trifluoromethyl)phenyl)ethyl)-1-piperazinyl | 3-isoquinolinol-8-yl |
| 88 | 4-(1,1-dimethylethyl)-1-cyclohexen-1-yl | 3-isoquinolinol-8-yl |
| 89 | 4-(1,1-dimethylethyl)-1-cyclohexyl | 3-isoquinolinol-8-yl |
| 90 | 4-(trifluoromethyl)-1-cyclohexen-1-yl | 3-isoquinolinol-8-yl |
| 91 | 4-(trifluoromethyl)cyclohexyl | 3-isoquinolinol-8-yl |
| 92 | 1-[1-(4-fluoro-phenyl)-ethyl]-1,2,3,6-tetrahydro-pyridin-4-yl | 3-isoquinolinol-8-yl |
| 93 | 1-[1-(4-fluoro-phenyl)-ethyl]-piperidin-4-yl | 3-isoquinolinol-8-yl |
| 94 | ((2,4-difluorophenyl)ethyl)-1-piperazinyl | quinolin-7-yl |
| 95 | ((2-fluorophenyl)ethyl)-1-piperazinyl | quinolin-7-yl |
| 96 | ((3-fluorophenyl)ethyl)-1-piperazinyl | quinolin-7-yl |
| 97 | ((4-bromophenyl)ethyl)-1-piperazinyl | quinolin-7-yl |
| 98 | ((4-chlorophenyl)ethyl)-1-piperazinyl | quinolin-7-yl |
| 100 | ((4-fluorophenyl)propyl)-3-methyl-1-piperazinyl | quinolin-7-yl |
| 101 | ((4-trifluoromethyl)phenyl)ethyl)-1-piperazinyl | quinolin-7-yl |
| 102 | 4-(1,1-dimethylethyl)-1-cyclohexen-1-yl | quinolin-7-yl |
| 103 | 4-(1,1-dimethylethyl)-1-cyclohexyl | quinolin-7-yl |
| 104 | 4-(trifluoromethyl)-1-cyclohexen-1-yl | quinolin-7-yl |
| 105 | 4-(trifluoromethyl)cyclohexyl | quinolin-7-yl |
| 106 | 1-[1-(4-fluoro-phenyl)-ethyl]-1,2,3,6-tetrahydro-pyridin-4-yl | quinolin-7-yl |
| 107 | 1-[1-(4-fluoro-phenyl)-ethyl]-piperidin-4-yl | quinolin-7-yl |
| 108 | ((2,4-difluorophenyl)ethyl)-1-piperazinyl | quinolin-8-yl |
| 109 | ((2-fluorophenyl)ethyl)-1-piperazinyl | quinolin-8-yl |
| 110 | ((3-fluorophenyl)ethyl)-1-piperazinyl | quinolin-8-yl |
| 111 | ((4-bromophenyl)ethyl)-1-piperazinyl | quinolin-8-yl |
| 112 | ((4-chlorophenyl)ethyl)-1-piperazinyl | quinolin-8-yl |
| 113 | ((4-fluorophenyl)ethyl)-1-piperazinyl | quinolin-8-yl |
| 114 | ((4-fluorophenyl)propyl)-3-methyl-1-piperazinyl | quinolin-8-yl |
| 115 | ((4-trifluoromethyl)phenyl)ethyl)-1-piperazinyl | quinolin-8-yl |
| 116 | 4-(1,1-dimethylethyl)-1-cyclohexen-1-yl | quinolin-8-yl |
| 117 | 4-(1,1-dimethylethyl)-1-cyclohexyl | quinolin-8-yl |
| 118 | 4-(trifluoromethyl)-1-cyclohexen-1-yl | quinolin-8-yl |
| 119 | 4-(trifluoromethyl)cyclohexyl | quinolin-8-yl |
| 120 | 1-[1-(4-fluoro-phenyl)-ethyl]-1,2,3,6-tetrahydro-pyridin-4-yl | quinolin-8-yl |
| 121 | 1-[1-(4-fluoro-phenyl)-ethyl]-piperidin-4-yl | quinolin-8-yl |

TABLE 2

| Ex # | Q | R⁴ |
|---|---|---|
| 122 | ((2,4-difluorophenyl)ethyl)-1-piperazinyl | 2-(acetylamino)-1,3-benzothiazol-4-yl |
| 123 | ((2-fluorophenyl)ethyl)-1-piperazinyl | 2-(acetylamino)-1,3-benzothiazol-4-yl |
| 124 | ((3-fluorophenyl)ethyl)-1-piperazinyl | 2-(acetylamino)-1,3-benzothiazol-4-yl |
| 125 | ((4-bromophenyl)ethyl)-1-piperazinyl | 2-(acetylamino)-1,3-benzothiazol-4-yl |
| 126 | ((4-chlorophenyl)ethyl)-1-piperazinyl | 2-(acetylamino)-1,3-benzothiazol-4-yl |
| 127 | ((4-fluorophenyl)ethyl)-1-piperazinyl | 2-(acetylamino)-1,3-benzothiazol-4-yl |
| 128 | ((4-fluorophenyl)propyl)-3-methyl-1-piperazinyl | 2-(acetylamino)-1,3-benzothiazol-4-yl |
| 129 | ((4-trifluoromethyl)phenyl)ethyl)-1-piperazinyl | 2-(acetylamino)-1,3-benzothiazol-4-yl |
| 130 | 4-(1,1-dimethylethyl)-1-cyclohexen-1-yl | 2-(acetylamino)-1,3-benzothiazol-4-yl |

TABLE 2-continued

| Ex # | Q | R⁴ |
|---|---|---|
| 131 | 4-(1,1-dimethylethyl)-1cyclohexyl | 2-(acetylamino)-1,3-benzothiazol-4-yl |
| 132 | 4-(trifluoromethyl)-1-cyclohexen-1-yl | 2-(acetylamino)-1,3-benzothiazol-4-yl |
| 133 | 4-(trifluoromethyl)cyclohexyl | 2-(acetylamino)-1,3-benzothiazol-4-yl |
| 134 | 1-[1-(4-fluoro-phenyl)-ethyl]-1,2,3,6-tetrahydro-pyridin-4-yl | 2-(acetylamino)-1,3-benzothiazol-4-yl |
| 135 | 1-[1-(4-fluoro-phenyl)-ethyl]-piperidin-4-yl | 2-(acetylamino)-1,3-benzothiazol-4-yl |
| 136 | ((2,4-difluorophenyl)ethyl)-1-piperazinyl | 2-(amino)-1,3-benzothiazol-4-yl |
| 137 | ((2-fluorophenyl)ethyl)-1-piperazinyl | 2-(amino)-1,3-benzothiazol-4-yl |
| 138 | ((3-fluorophenyl)ethyl)-1-piperazinyl | 2-(amino)-1,3-benzothiazol-4-yl |
| 139 | ((4-bromophenyl)ethyl)-1-piperazinyl | 2-(amino)-1,3-benzothiazol-4-yl |
| 140 | ((4-chlorophenyl)ethyl)-1-piperazinyl | 2-(amino)-1,3-benzothiazol-4-yl |
| 141 | ((4-fluorophenyl)ethyl)-1-piperazinyl | 2-(amino)-1,3-benzothiazol-4-yl |
| 142 | ((4-fluorophenyl)propyl)-3-methyl-1-piperazinyl | 2-(amino)-1,3-benzothiazol-4-yl |
| 143 | ((4-trifluoromethyl)phenyl)ethyl)-1-piperazinyl | 2-(amino)-1,3-benzothiazol-4-yl |
| 144 | 4-(1,1-dimethylethyl)-1-cyclohexen-1-yl | 2-(amino)-1,3-benzothiazol-4-yl |
| 145 | 4-(1,1-dimethylethyl)-1-cyclohexyl | 2-(amino)-1,3-benzothiazol-4-yl |
| 146 | 4-(trifluoromethyl)-1-cyclohexen-1-yl | 2-(amino)-1,3-benzothiazol-4-yl |
| 147 | 4-(trifluoromethyl)cyclohexyl | 2-(amino)-1,3-benzothiazol-4-yl |
| 148 | 1-[1-(4-fluoro-phenyl)-ethyl]-1,2,3,6-tetrahydro-pyridin-4-yl | 2-(amino)-1,3-benzothiazol-4-yl |
| 149 | 1-[1-(4-fluoro-phenyl)-ethyl]-piperidin-4-yl | 2-(amino)-1,3-benzothiazol-4-yl |
| 150 | ((2,4-difluorophenyl)ethyl)-1-piperazinyl | 2-aminoquinolin-8-yl |
| 151 | ((2-fluorophenyl)ethyl)-1-piperazinyl | 2-aminoquinolin-8-yl |
| 152 | ((3-fluorophenyl)ethyl)-1-piperazinyl | 2-aminoquinolin-8-yl |
| 153 | ((4-bromophenyl)ethyl)-1-piperazinyl | 2-aminoquinolin-8-yl |
| 154 | ((4-chlorophenyl)ethyl)-1-piperazinyl | 2-aminoquinolin-8-yl |
| 155 | ((4-fluorophenyl)ethyl)-1-piperazinyl | 2-aminoquinolin-8-yl |
| 156 | ((4-fluorophenyl)propyl)-3-methyl-1-piperazinyl | 2-aminoquinolin-8-yl |
| 157 | ((4-trifluoromethyl)phenyl)ethyl)-1-piperazinyl | 2-aminoquinolin-8-yl |
| 158 | 4-(1,1-dimethylethyl)-1-cyclohexen-1-yl | 2-aminoquinolin-8-yl |
| 159 | 4-(1,1-dimethylethyl)-1-cyclohexyl | 2-aminoquinolin-8-yl |
| 160 | 4-(trifluoromethyl)-1-cyclohexen-1-yl | 2-aminoquinolin-8-yl |
| 161 | 4-(trifluoromethyl)cyclohexyl | 2-aminoquinolin-8-yl |
| 162 | 1-[1-(4-fluoro-phenyl)-ethyl]-1,2,3,6-tetrahydro-pyridin-4-yl | 2-aminoquinolin-8-yl |
| 163 | 1-[1-(4-fluoro-phenyl)-ethyl]-piperidin-4-yl | 2-aminoquinolin-8-yl |
| 164 | ((2,4-difluorophenyl)ethyl)-1-piperazinyl | 3,4-dihydro-2(1H)-quinoxalinone-5-yl |
| 165 | ((2-fluorophenyl)ethyl)-1-piperazinyl | 3,4-dihydro-2(1H)-quinoxalinone-5-yl |
| 166 | ((3-fluorophenyl)ethyl)-1-piperazinyl | 3,4-dihydro-2(1H)-quinoxalinone-5-yl |
| 167 | ((4-bromophenyl)ethyl)-1-piperazinyl | 3,4-dihydro-2(1H)-quinoxalinone-5-yl |
| 168 | ((4-chlorophenyl)ethyl)-1-piperazinyl | 3,4-dihydro-2(1H)-quinoxalinone-5-yl |
| 169 | ((4-fluorophenyl)ethyl)-1-piperazinyl | 3,4-dihydro-2(1H)-quinoxalinone-5-yl |
| 170 | ((4-fluorophenyl)propyl)-3-methyl-1-piperazinyl | 3,4-dihydro-2(1H)-quinoxalinone-5-yl |
| 171 | ((4-trifluoromethyl)phenyl)ethyl)-1-piperazinyl | 3,4-dihydro-2(1H)-quinoxalinone-5-yl |
| 172 | 4-(1,1-dimethylethyl)-1-cyclohexen-1-yl | 3,4-dihydro-2(1H)-quinoxalinone-5-yl |
| 173 | 4-(1,1-dimethylethyl)-1-cyclohexyl | 3,4-dihydro-2(1H)-quinoxalinone-5-yl |
| 174 | 4-(trifluoromethyl)-1-cyclohexen-1-yl | 3,4-dihydro-2(1H)-quinoxalinone-5-yl |
| 175 | 4-(trifluoromethyl)cyclohexyl | 3,4-dihydro-2(1H)-quinoxalinone-5-yl |
| 176 | 1-[1-(4-fluoro-phenyl)-ethyl]-1,2,3,6-tetrahydro-pyridin-4-yl | 3,4-dihydro-2(1H)-quinoxalinone-5-yl |
| 177 | 1-[1-(4-fluoro-phenyl)-ethyl]-piperidin-4-yl | 3,4-dihydro-2(1H)-quinoxalinone-5-yl |
| 178 | ((2,4-difluorophenyl)ethyl)-1-piperazinyl | 3-amino-1H-quinoxalin-2-one-5-yl |
| 179 | ((2-fluorophenyl)ethyl)-1-piperazinyl | 3-amino-1H-quinoxalin-2-one-5-yl |
| 180 | ((3-fluorophenyl)ethyl)-1-piperazinyl | 3-amino-1H-quinoxalin-2-one-5-yl |
| 181 | ((4-bromophenyl)ethyl)-1-piperazinyl | 3-amino-1H-quinoxalin-2-one-5-yl |
| 182 | ((4-chlorophenyl)ethyl)-1-piperazinyl | 3-amino-1H-quinoxalin-2-one-5-yl |
| 183 | ((4-fluorophenyl)ethyl)-1-piperazinyl | 3-amino-1H-quinoxalin-2-one-5-yl |
| 184 | ((4-fluorophenyl)propyl)-3-methyl-1-piperazinyl | 3-amino-1H-quinoxalin-2-one-5-yl |
| 185 | ((4-trifluoromethyl)phenyl)ethyl)-1-piperazinyl | 3-amino-1H-quinoxalin-2-one-5-yl |
| 186 | 4-(1,1-dimethylethyl)-1-cyclohexen-1-yl | 3-amino-1H-quinoxalin-2-one-5-yl |
| 187 | 4-(1,1-dimethylethyl)-1-cyclohexyl | 3-amino-1H-quinoxalin-2-one-5-yl |
| 188 | 4-(trifluoromethyl)-1-cyclohexen-1-yl | 3-amino-1H-quinoxalin-2-one-5-yl |
| 189 | 4-(trifluoromethyl)cyclohexyl | 3-amino-1H-quinoxalin-2-one-5-yl |
| 190 | 1-[1-(4-fluoro-phenyl)-ethyl]-1,2,3,6-tetrahydro-pyridin-4-yl | 3-amino-1H-quinoxalin-2-one-5-yl |
| 191 | 1-[1-(4-fluoro-phenyl)-ethyl]-piperidin-4-yl | 3-amino-1H-quinoxalin-2-one-5-yl |
| 192 | ((2,4-difluorophenyl)ethyl)-1-piperazinyl | 3-isoquinolinol-8-yl |
| 193 | ((2-fluorophenyl)ethyl)-1-piperazinyl | 3-isoquinolinol-8-yl |

TABLE 2-continued

| Ex # | Q | R⁴ |
|---|---|---|
| 194 | ((3-fluorophenyl)ethyl)-1-piperazinyl | 3-isoquinolinol-8-yl |
| 195 | ((4-bromophenyl)ethyl)-1-piperazinyl | 3-isoquinolinol-8-yl |
| 196 | ((4-chlorophenyl)ethyl)-1-piperazinyl | 3-isoquinolinol-8-yl |
| 197 | ((4-fluorophenyl)ethyl)-1-piperazinyl | 3-isoquinolinol-8-yl |
| 198 | ((4-fluorophenyl)propyl)-3-methyl-1-piperazinyl | 3-isoquinolinol-8-yl |
| 199 | ((4-trifluoromethyl)phenyl)ethyl)-1-piperazinyl | 3-isoquinolinol-8-yl |
| 200 | 4-(1,1-dimethylethyl)-1-cyclohexen-1-yl | 3-isoquinolinol-8-yl |
| 201 | 4-(1,1-dimethylethyl)-1-cyclohexyl | 3-isoquinolinol-8-yl |
| 202 | 4-(trifluoromethyl)-1-cyclohexen-1-yl | 3-isoquinolinol-8-yl |
| 203 | 4-(trifluoromethyl)cyclohexyl | 3-isoquinolinol-8-yl |
| 204 | 1-[1-(4-fluoro-phenyl)-ethyl]-1,2,3,6-tetrahydro-pyridin-4-yl | 3-isoquinolinol-8-yl |
| 205 | 1-[1-(4-fluoro-phenyl)-ethyl]-piperidin-4-yl | 3-isoquinolinol-8-yl |
| 206 | ((2,4-difluorophenyl)ethyl)-1-piperazinyl | quinolin-7-yl |
| 207 | ((2-fluorophenyl)ethyl)-1-piperazinyl | quinolin-7-yl |
| 208 | ((3-fluorophenyl)ethyl)-1-piperazinyl | quinolin-7-yl |
| 209 | ((4-bromophenyl)ethyl)-1-piperazinyl | quinolin-7-yl |
| 210 | ((4-chlorophenyl)ethyl)-1-piperazinyl | quinolin-7-yl |
| 211 | ((4-fluorophenyl)ethyl)-1-piperazinyl | quinolin-7-yl |
| 212 | ((4-fluorophenyl)propyl)-3-methyl-1-piperazinyl | quinolin-7-yl |
| 213 | ((4-trifluoromethyl)phenyl)ethyl)-1-piperazinyl | quinolin-7-yl |
| 214 | 4-(1,1-dimethylethyl)-1-cyclohexen-1-yl | quinolin-7-yl |
| 215 | 4-(1,1-dimethylethyl)-1-cyclohexyl | quinolin-7-yl |
| 216 | 4-(trifluoromethyl)-1-cyclohexen-1-yl | quinolin-7-yl |
| 217 | 4-(trifluoromethyl)cyclohexyl | quinolin-7-yl |
| 218 | 1-[1-(4-fluoro-phenyl)-ethyl]-1,2,3,6-tetrahydro-pyridin-4-yl | quinolin-7-yl |
| 219 | 1-[1-(4-fluoro-phenyl)-ethyl]-piperidin-4-yl | quinolin-7-yl |
| 220 | ((2,4-difluorophenyl)ethyl)-1-piperazinyl | quinolin-8-yl |
| 221 | ((2-fluorophenyl)ethyl)-1-piperazinyl | quinolin-8-yl |
| 222 | ((3-fluorophenyl)ethyl)-1-piperazinyl | quinolin-8-yl |
| 223 | ((4-bromophenyl)ethyl)-1-piperazinyl | quinolin-8-yl |
| 224 | ((4-chlorophenyl)ethyl)-1-piperazinyl | quinolin-8-yl |
| 225 | ((4-fluorophenyl)ethyl)-1-piperazinyl | quinolin-8-yl |
| 226 | ((4-fluorophenyl)propyl)-3-methyl-1-piperazinyl | quinolin-8-yl |
| 227 | ((4-trifluoromethyl)phenyl)ethyl)-1-piperazinyl | quinolin-8-yl |
| 228 | 4-(1,1-dimethylethyl)-1-cyclohexen-1-yl | quinolin-8-yl |
| 229 | 4-(1,1-dimethylethyl)-1-cyclohexyl | quinolin-8-yl |
| 230 | 4-(trifluoromethyl)-1-cyclohexen-1-yl | quinolin-8-yl |
| 231 | 4-(trifluoromethyl)cyclohexyl | quinolin-8-yl |
| 232 | 1-[1-(4-fluoro-phenyl)-ethyl]-1,2,3,6-tetrahydro-pyridin-4-yl | quinolin-8-yl |
| 233 | 1-[1-(4-fluoro-phenyl)-ethyl]-piperidin-4-yl | quinolin-8-yl |

TABLE 3

| Ex # | Q | R⁴ |
|---|---|---|
| 234 | ((2,4-difluorophenyl)ethyl)-1-piperazinyl | 2-(acetylamino)-1,3-benzothiazol-4-yl |
| 235 | ((2-fluorophenyl)ethyl)-1-piperazinyl | 2-(acetylamino)-1,3-benzothiazol-4-yl |
| 236 | ((3-fluorophenyl)ethyl)-1-piperazinyl | 2-(acetylamino)-1,3-benzothiazol-4-yl |
| 237 | ((4-bromophenyl)ethyl)-1-piperazinyl | 2-(acetylamino)-1,3-benzothiazol-4-yl |
| 238 | ((4-chlorophenyl)ethyl)-1-piperazinyl | 2-(acetylamino)-1,3-benzothiazol-4-yl |
| 239 | ((4-fluorophenyl)ethyl)-1-piperazinyl | 2-(acetylamino)-1,3-benzothiazol-4-yl |
| 240 | ((4-fluorophenyl)propyl)-3-methyl-1-piperazinyl | 2-(acetylamino)-1,3-benzothiazol-4-yl |
| 241 | ((4-trifluoromethyl)phenyl)ethyl)-1-piperazinyl | 2-(acetylamino)-1,3-benzothiazol-4-yl |
| 242 | 4-(1,1-dimethylethyl)-1-cyclohexen-1-yl | 2-(acetylamino)-1,3-benzothiazol-4-yl |
| 243 | 4-(1,1-dimethylethyl)-1-cyclohexyl | 2-(acetylamino)-1,3-benzothiazol-4-yl |
| 244 | 4-(trifluoromethyl)-1-cyclohexen-1-yl | 2-(acetylamino)-1,3-benzothiazol-4-yl |
| 245 | 4-(trifluoromethyl)cyclohexyl | 2-(acetylamino)-1,3-benzothiazol-4-yl |

TABLE 3-continued

| Ex # | Q | R⁴ |
|---|---|---|
| 246 | 1-[1-(4-fluoro-phenyl)-ethyl]-1,2,3,6-tetrahydro-pyridin-4-yl | 2-(acetylamino)-1,3-benzothiazol-4-yl |
| 247 | 1-[1-(4-fluoro-phenyl)-ethyl]-piperidin-4-yl | 2-(acetylamino)-1,3-benzothiazol-4-yl |
| 248 | ((2,4-difluorophenyl)ethyl)-1-piperazinyl | 2-(amino)-1,3-benzothiazol-4-yl |
| 249 | ((2-fluorophenyl)ethyl)-1-piperazinyl | 2-(amino)-1,3-benzothiazol-4-yl |
| 250 | ((3-fluorophenyl)ethyl)-1-piperazinyl | 2-(amino)-1,3-benzothiazol-4-yl |
| 251 | ((4-bromophenyl)ethyl)-1-piperazinyl | 2-(amino)-1,3-benzothiazol-4-yl |
| 252 | ((4-chlorophenyl)ethyl)-1-piperazinyl | 2-(amino)-1,3-benzothiazol-4-yl |
| 253 | ((4-fluorophenyl)ethyl)-1-piperazinyl | 2-(amino)-1,3-benzothiazol-4-yl |
| 254 | ((4-fluorophenyl)propyl)-3-methyl-1-piperazinyl | 2-(amino)-1,3-benzothiazol-4-yl |
| 255 | ((4-trifluoromethyl)phenyl)ethyl)-1-piperazinyl | 2-(amino)-1,3-benzothiazol-4-yl |
| 256 | 4-(1,1-dimethylethyl)-1-cyclohexen-1-yl | 2-(amino)-1,3-benzothiazol-4-yl |
| 257 | 4-(1,1-dimethylethyl)-1-cyclohexyl | 2-(amino)-1,3-benzothiazol-4-yl |
| 258 | 4-(trifluoromethyl)-1-cyclohexen-1-yl | 2-(amino)-1,3-benzothiazol-4-yl |
| 259 | 4-(trifluoromethyl)cyclohexyl | 2-(amino)-1,3-benzothiazol-4-yl |
| 260 | 1-[1-(4-fluoro-phenyl)-ethyl]-1,2,3,6-tetrahydro-pyridin-4-yl | 2-(amino)-1,3-benzothiazol-4-yl |
| 261 | 1-[1-(4-fluoro-phenyl)-ethyl]-piperidin-4-yl | 2-(amino)-1,3-benzothiazol-4-yl |
| 262 | ((2,4-difluorophenyl)ethyl)-1-piperazinyl | 2-aminoquinolin-8-yl |
| 263 | ((2-fluorophenyl)ethyl)-1-piperazinyl | 2-aminoquinolin-8-yl |
| 264 | ((3-fluorophenyl)ethyl)-1-piperazinyl | 2-aminoquinolin-8-yl |
| 265 | ((4-bromophenyl)ethyl)-1-piperazinyl | 2-aminoquinolin-8-yl |
| 266 | ((4-chlorophenyl)ethyl)-1-piperazinyl | 2-aminoquinolin-8-yl |
| 267 | ((4-fluorophenyl)ethyl)-1-piperazinyl | 2-aminoquinolin-8-yl |
| 268 | ((4-fluorophenyl)propyl)-3-methyl-1-piperazinyl | 2-aminoquinolin-8-yl |
| 269 | ((4-trifluoromethyl)phenyl)ethyl)-1-piperazinyl | 2-aminoquinolin-8-yl |
| 270 | 4-(1,1-dimethylethyl)-1-cyclohexen-1-yl | 2-aminoquinolin-8-yl |
| 271 | 4-(1,1-dimethylethyl)-1-cyclohexyl | 2-aminoquinolin-8-yl |
| 272 | 4-(trifluoromethyl)-1-cyclohexen-1-yl | 2-aminoquinolin-8-yl |
| 273 | 4-(trifluoromethyl)cyclohexyl | 2-aminoquinolin-8-yl |
| 274 | 1-[1-(4-fluoro-phenyl)-ethyl]-1,2,3,6-tetrahydro-pyridin-4-yl | 2-aminoquinolin-8-yl |
| 275 | 1-[1-(4-fluoro-phenyl)-ethyl]-piperidin-4-yl | 2-aminoquinolin-8-yl |
| 276 | ((2,4-difluorophenyl)ethyl)-1-piperazinyl | 3,4-dihydro-2(1H)-quinoxalinone-5-yl |
| 277 | ((2-fluorophenyl)ethyl)-1-piperazinyl | 3,4-dihydro-2(1H)-quinoxalinone-5-yl |
| 278 | ((3-fluorophenyl)ethyl)-1-piperazinyl | 3,4-dihydro-2(1H)-quinoxalinone-5-yl |
| 279 | ((4-bromophenyl)ethyl)-1-piperazinyl | 3,4-dihydro-2(1H)-quinoxalinone-5-yl |
| 280 | ((4-chlorophenyl)ethyl)-1-piperazinyl | 3,4-dihydro-2(1H)-quinoxalinone-5-yl |
| 281 | ((4-fluorophenyl)ethyl)-1-piperazinyl | 3,4-dihydro-2(1H)-quinoxalinone-5-yl |
| 282 | ((4-fluorophenyl)propyl)-3-methyl-1-piperazinyl | 3,4-dihydro-2(1H)-quinoxalinone-5-yl |
| 283 | ((4-trifluoromethyl)phenyl)ethyl)-1-piperazinyl | 3,4-dihydro-2(1H)-quinoxalinone-5-yl |
| 284 | 4-(1,1-dimethylethyl)-1-cyclohexen-1-yl | 3,4-dihydro-2(1H)-quinoxalinone-5-yl |
| 285 | 4-(1,1-dimethylethyl)-1-cyclohexyl | 3,4-dihydro-2(1H)-quinoxalinone-5-yl |
| 286 | 4-(trifluoromethyl)-1-cyclohexen-1-yl | 3,4-dihydro-2(1H)-quinoxalinone-5-yl |
| 287 | 4-(trifluoromethyl)cyclohexyl | 3,4-dihydro-2(1H)-quinoxalinone-5-yl |
| 288 | 1-[1-(4-fluoro-phenyl)-ethyl]-1,2,3,6-tetrahydro-pyridin-4-yl | 3,4-dihydro-2(1H)-quinoxalinone-5-yl |
| 289 | 1-[1-(4-fluoro-phenyl)-ethyl]-piperidin-4-yl | 3,4-dihydro-2(1H)-quinoxalinone-5-yl |
| 290 | ((2,4-difluorophenyl)ethyl)-1-piperazinyl | 3-amino-1H-quinoxalin-2-one-5-yl |
| 291 | ((2-fluorophenyl)ethyl)-1-piperazinyl | 3-amino-1H-quinoxalin-2-one-5-yl |
| 292 | ((3-fluorophenyl)ethyl)-1-piperazinyl | 3-amino-1H-quinoxalin-2-one-5-yl |
| 293 | ((4-bromophenyl)ethyl)-1-piperazinyl | 3-amino-1H-quinoxalin-2-one-5-yl |
| 294 | ((4-chlorophenyl)ethyl)-1-piperazinyl | 3-amino-1H-quinoxalin-2-one-5-yl |
| 295 | ((4-fluorophenyl)ethyl)-1-piperazinyl | 3-amino-1H-quinoxalin-2-one-5-yl |
| 296 | ((4-fluorophenyl)propyl)-3-methyl-1-piperazinyl | 3-amino-1H-quinoxalin-2-one-5-yl |
| 297 | ((4-trifluoromethyl)phenyl)ethyl)-1-piperazinyl | 3-amino-1H-quinoxalin-2-one-5-yl |
| 298 | 4-(1,1-dimethylethyl)-1-cyclohexen-1-yl | 3-amino-1H-quinoxalin-2-one-5-yl |
| 299 | 4-(1,1-dimethylethyl)-1-cyclohexyl | 3-amino-1H-quinoxalin-2-one-5-yl |
| 300 | 4-(trifluoromethyl)-1-cyclohexen-1-yl | 3-amino-1H-quinoxalin-2-one-5-yl |
| 301 | 4-(trifluoromethyl)cyclohexyl | 3-amino-1H-quinoxalin-2-one-5-yl |
| 302 | 1-[1-(4-fluoro-phenyl)-ethyl]-1,2,3,6-tetrahydro-pyridin-4-yl | 3-amino-1H-quinoxalin-2-one-5-yl |
| 303 | 1-[1-(4-fluoro-phenyl)-ethyl]-piperidin-4-yl | 3-amino-1H-quinoxalin-2-one-5-yl |
| 304 | ((2,4-difluorophenyl)ethyl)-1-piperazinyl | 3-isoquinolinol-8-yl |
| 305 | ((2-fluorophenyl)ethyl)-1-piperazinyl | 3-isoquinolinol-8-yl |
| 306 | ((3-fluorophenyl)ethyl)-1-piperazinyl | 3-isoquinolinol-8-yl |
| 307 | ((4-bromophenyl)ethyl)-1-piperazinyl | 3-isoquinolinol-8-yl |
| 308 | ((4-chlorophenyl)ethyl)-1-piperazinyl | 3-isoquinolinol-8-yl |
| 309 | ((4-fluorophenyl)ethyl)-1-piperazinyl | 3-isoquinolinol-8-yl |
| 310 | ((4-fluorophenyl)propyl)-3-methyl-1-piperazinyl | 3-isoquinolinol-8-yl |

TABLE 3-continued

| Ex # | Q | R⁴ |
|---|---|---|
| 311 | ((4-trifluoromethyl)phenyl)ethyl)-1-piperazinyl | 3-isoquinolinol-8-yl |
| 312 | 4-(1,1-dimethylethyl)-1-cyclohexen-1-yl | 3-isoquinolinol-8-yl |
| 313 | 4-(1,1-dimethylethyl)-1-cyclohexyl | 3-isoquinolinol-8-yl |
| 314 | 4-(trifluoromethyl)-1-cyclohexen-1-yl | 3-isoquinolinol-8-yl |
| 315 | 4-(trifluoromethyl)cyclohexyl | 3-isoquinolinol-8-yl |
| 316 | 1-[1-(4-fluoro-phenyl)-ethyl]-1,2,3,6-tetrahydro-pyridin-4-yl | 3-isoquinolinol-8-yl |
| 317 | 1-[1-(4-fluoro-phenyl)-ethyl]-piperidin-4-yl | 3-isoquinolinol-8-yl |
| 318 | ((2,4-difluorophenyl)ethyl)-1-piperazinyl | quinolin-7-yl |
| 319 | ((2-fluorophenyl)ethyl)-1-piperazinyl | quinolin-7-yl |
| 320 | ((3-fluorophenyl)ethyl)-1-piperazinyl | quinolin-7-yl |
| 321 | ((4-bromophenyl)ethyl)-1-piperazinyl | quinolin-7-yl |
| 322 | ((4-chlorophenyl)ethyl)-1-piperazinyl | quinolin-7-yl |
| 323 | ((4-fluorophenyl)ethyl)-1-piperazinyl | quinolin-7-yl |
| 324 | ((4-fluorophenyl)propyl)-3-methyl-1-piperazinyl | quinolin-7-yl |
| 325 | ((4-trifluoromethyl)phenyl)ethyl)-1-piperazinyl | quinolin-7-yl |
| 326 | 4-(1,1-dimethylethyl)-1-cyclohexen-1-yl | quinolin-7-yl |
| 327 | 4-(1,1-dimethylethyl)-1-cyclohexyl | quinolin-7-yl |
| 328 | 4-(trifluoromethyl)-1-cyclohexen-1-yl | quinolin-7-yl |
| 329 | 4-(trifluoromethyl)cyclohexyl | quinolin-7-yl |
| 330 | 1-[1-(4-fluoro-phenyl)-ethyl]-1,2,3,6-tetrahydro-pyridin-4-yl | quinolin-7-yl |
| 331 | 1-[1-(4-fluoro-phenyl)-ethyl]-piperidin-4-yl | quinolin-7-yl |
| 332 | ((2,4-difluorophenyl)ethyl)-1-piperazinyl | quinolin-8-yl |
| 333 | ((2-fluorophenyl)ethyl)-1-piperazinyl | quinolin-8-yl |
| 334 | ((3-fluorophenyl)ethyl)-1-piperazinyl | quinolin-8-yl |
| 335 | ((4-bromophenyl)ethyl)-1-piperazinyl | quinolin-8-yl |
| 336 | ((4-chlorophenyl)ethyl)-1-piperazinyl | quinolin-8-yl |
| 337 | ((4-fluorophenyl)ethyl)-1-piperazinyl | quinolin-8-yl |
| 338 | ((4-fluorophenyl)propyl)-3-methyl-1-piperazinyl | quinolin-8-yl |
| 339 | ((4-trifluoromethyl)phenyl)ethyl)-1-piperazinyl | quinolin-8-yl |
| 340 | 4-(1,1-dimethylethyl)-1-cyclohexen-1-yl | quinolin-8-yl |
| 341 | 4-(1,1-dimethylethyl)-1-cyclohexyl | quinolin-8-yl |
| 342 | 4-(trifluoromethyl)-1-cyclohexen-1-yl | quinolin-8-yl |
| 343 | 4-(trifluoromethyl)cyclohexyl | quinolin-8-yl |
| 344 | 1-[1-(4-fluoro-phenyl)-ethyl]-1,2,3,6-tetrahydro-pyridin-4-yl | quinolin-8-yl |
| 345 | 1-[1-(4-fluoro-phenyl)-ethyl]-piperidin-4-yl | quinolin-8-yl |

TABLE 4

| Ex # | Q | R⁴ |
|---|---|---|
| 346 | ((2,4-difluorophenyl)ethyl)-1-piperazinyl | 2-(acetylamino)-1,3-benzothiazol-4-yl |
| 347 | ((2-fluorophenyl)ethyl)-1-piperazinyl | 2-(acetylamino)-1,3-benzothiazol-4-yl |
| 348 | ((3-fluorophenyl)ethyl)-1-piperazinyl | 2-(acetylamino)-1,3-benzothiazol-4-yl |
| 349 | ((4-bromophenyl)ethyl)-1-piperazinyl | 2-(acetylamino)-1,3-benzothiazol-4-yl |
| 350 | ((4-chlorophenyl)ethyl)-1-piperazinyl | 2-(acetylamino)-1,3-benzothiazol-4-yl |
| 352 | ((4-fluorophenyl)propyl)-3-methyl-1-piperazinyl | 2-(acetylamino)-1,3-benzothiazol-4-yl |
| 353 | ((4-trifluoromethyl)phenyl)ethyl)-1-piperazinyl | 2-(acetylamino)-1,3-benzothiazol-4-yl |
| 354 | 4-(1,1-dimethylethyl)-1-cyclohexen-1-yl | 2-(acetylamino)-1,3-benzothiazol-4-yl |
| 355 | 4-(1,1-dimethylethyl)-1-cyclohexyl | 2-(acetylamino)-1,3-benzothiazol-4-yl |
| 357 | 4-(trifluoromethyl)cyclohexyl | 2-(acetylamino)-1,3-benzothiazol-4-yl |
| 358 | 1-[1-(4-fluoro-phenyl)-ethyl]-1,2,3,6-tetrahydro-pyridin-4-yl | 2-(acetylamino)-1,3-benzothiazol-4-yl |
| 359 | 1-[1-(4-fluoro-phenyl)-ethyl]-piperidin-4-yl | 2-(acetylamino)-1,3-benzothiazol-4-yl |
| 360 | ((2,4-difluorophenyl)ethyl)-1-piperazinyl | 2-(amino)-1,3-benzothiazol-4-yl |
| 361 | ((2-fluorophenyl)ethyl)-1-piperazinyl | 2-(amino)-1,3-benzothiazol-4-yl |
| 362 | ((3-fluorophenyl)ethyl)-1-piperazinyl | 2-(amino)-1,3-benzothiazol-4-yl |
| 363 | ((4-bromophenyl)ethyl)-1-piperazinyl | 2-(amino)-1,3-benzothiazol-4-yl |
| 364 | ((4-chlorophenyl)ethyl)-1-piperazinyl | 2-(amino)-1,3-benzothiazol-4-yl |
| 365 | ((4-fluorophenyl)ethyl)-1-piperazinyl | 2-(amino)-1,3-benzothiazol-4-yl |

TABLE 4-continued

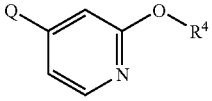

| Ex # | Q | R⁴ |
|---|---|---|
| 366 | ((4-fluorophenyl)propyl)-3-methyl-1-piperazinyl | 2-(amino)-1,3-benzothiazol-4-yl |
| 367 | ((4-trifluoromethyl)phenyl)ethyl)-1-piperazinyl | 2-(amino)-1,3-benzothiazol-4-yl |
| 368 | 4-(1,1-dimethylethyl)-1-cyclohexen-1-yl | 2-(amino)-1,3-benzothiazol-4-yl |
| 369 | 4-(1,1-dimethylethyl)-1-cyclohexyl | 2-(amino)-1,3-benzothiazol-4-yl |
| 370 | 4-(trifluoromethyl)-1-cyclohexen-1-yl | 2-(amino)-1,3-benzothiazol-4-yl |
| 371 | 4-(trifluoromethyl)cyclohexyl | 2-(amino)-1,3-benzothiazol-4-yl |
| 372 | 1-[1-(4-fluoro-phenyl)-ethyl]-1,2,3,6-tetrahydro-pyridin-4-yl | 2-(amino)-1,3-benzothiazol-4-yl |
| 373 | 1-[1-(4-fluoro-phenyl)-ethyl]-piperidin-4-yl | 2-(amino)-1,3-benzothiazol-4-yl |
| 374 | ((2,4-difluorophenyl)ethyl)-1-piperazinyl | 2-aminoquinolin-8-yl |
| 375 | ((2-fluorophenyl)ethyl)-1-piperazinyl | 2-aminoquinolin-8-yl |
| 376 | ((3-fluorophenyl)ethyl)-1-piperazinyl | 2-aminoquinolin-8-yl |
| 377 | ((4-bromophenyl)ethyl)-1-piperazinyl | 2-aminoquinolin-8-yl |
| 378 | ((4-chlorophenyl)ethyl)-1-piperazinyl | 2-aminoquinolin-8-yl |
| 379 | ((4-fluorophenyl)ethyl)-1-piperazinyl | 2-aminoquinolin-8-yl |
| 380 | ((4-fluorophenyl)propyl)-3-methyl-1-piperazinyl | 2-aminoquinolin-8-yl |
| 381 | ((4-trifluoromethyl)phenyl)ethyl)-1-piperazinyl | 2-aminoquinolin-8-yl |
| 382 | 4-(1,1-dimethylethyl)-1-cyclohexen-1-yl | 2-aminoquinolin-8-yl |
| 383 | 4-(1,1-dimethylethyl)-1-cyclohexyl | 2-aminoquinolin-8-yl |
| 384 | 4-(trifluoromethyl)-1-cyclohexen-1-yl | 2-aminoquinolin-8-yl |
| 385 | 4-(trifluoromethyl)cyclohexyl | 2-aminoquinolin-8-yl |
| 386 | 1-[1-(4-fluoro-phenyl)-ethyl]-1,2,3,6-tetrahydro-pyridin-4-yl | 2-aminoquinolin-8-yl |
| 387 | 1-[1-(4-fluoro-phenyl)-ethyl]-piperidin-4-yl | 2-aminoquinolin-8-yl |
| 388 | ((2,4-difluorophenyl)ethyl)-1-piperazinyl | 3,4-dihydro-2(1H)-quinoxalinone-5-yl |
| 389 | ((2-fluorophenyl)ethyl)-1-piperazinyl | 3,4-dihydro-2(1H)-quinoxalinone-5-yl |
| 390 | ((3-fluorophenyl)ethyl)-1-piperazinyl | 3,4-dihydro-2(1H)-quinoxalinone-5-yl |
| 391 | ((4-bromophenyl)ethyl)-1-piperazinyl | 3,4-dihydro-2(1H)-quinoxalinone-5-yl |
| 392 | ((4-chlorophenyl)ethyl)-1-piperazinyl | 3,4-dihydro-2(1H)-quinoxalinone-5-yl |
| 393 | ((4-fluorophenyl)ethyl)-1-piperazinyl | 3,4-dihydro-2(1H)-quinoxalinone-5-yl |
| 394 | ((4-fluorophenyl)propyl)-3-methyl-1-piperazinyl | 3,4-dihydro-2(1H)-quinoxalinone-5-yl |
| 395 | ((4-trifluoromethyl)phenyl)ethyl)-1-piperazinyl | 3,4-dihydro-2(1H)-quinoxalinone-5-yl |
| 396 | 4-(1,1-dimethylethyl)-1-cyclohexen-1-yl | 3,4-dihydro-2(1H)-quinoxalinone-5-yl |
| 397 | 4-(1,1-dimethylethyl)-1-cyclohexyl | 3,4-dihydro-2(1H)-quinoxalinone-5-yl |
| 398 | 4-(trifluoromethyl)-1-cyclohexen-1-yl | 3,4-dihydro-2(1H)-quinoxalinone-5-yl |
| 399 | 4-(trifluoromethyl)cyclohexyl | 3,4-dihydro-2(1H)-quinoxalinone-5-yl |
| 400 | 1-[1-(4-fluoro-phenyl)-ethyl]-1,2,3,6-tetrahydro-pyridin-4-yl | 3,4-dihydro-2(1H)-quinoxalinone-5-yl |
| 401 | 1-[1-(4-fluoro-phenyl)-ethyl]-piperidin-4-yl | 3,4-dihydro-2(1H)-quinoxalinone-5-yl |
| 402 | ((2,4-difluorophenyl)ethyl)-1-piperazinyl | 3-amino-1H-quinoxalin-2-one-5-yl |
| 403 | ((2-fluorophenyl)ethyl)-1-piperazinyl | 3-amino-1H-quinoxalin-2-one-5-yl |
| 404 | ((3-fluorophenyl)ethyl)-1-piperazinyl | 3-amino-1H-quinoxalin-2-one-5-yl |
| 405 | ((4-bromophenyl)ethyl)-1-piperazinyl | 3-amino-1H-quinoxalin-2-one-5-yl |
| 406 | ((4-chlorophenyl)ethyl)-1-piperazinyl | 3-amino-1H-quinoxalin-2-one-5-yl |
| 408 | ((4-fluorophenyl)propyl)-3-methyl-1-piperazinyl | 3-amino-1H-quinoxalin-2-one-5-yl |
| 409 | ((4-trifluoromethyl)phenyl)ethyl)-1-piperazinyl | 3-amino-1H-quinoxalin-2-one-5-yl |
| 410 | 4-(1,1-dimethylethyl)-1-cyclohexen-1-yl | 3-amino-1H-quinoxalin-2-one-5-yl |
| 411 | 4-(1,1-dimethylethyl)-1-cyclohexyl | 3-amino-1H-quinoxalin-2-one-5-yl |
| 412 | 4-(trifluoromethyl)-1-cyclohexen-1-yl | 3-amino-1H-quinoxalin-2-one-5-yl |
| 413 | 4-(trifluoromethyl)cyclohexyl | 3-amino-1H-quinoxalin-2-one-5-yl |
| 414 | 1-[1-(4-fluoro-phenyl)-ethyl]-1,2,3,6-tetrahydro-pyridin-4-yl | 3-amino-1H-quinoxalin-2-one-5-yl |
| 415 | 1-[1-(4-fluoro-phenyl)-ethyl]-piperidin-4-yl | 3-amino-1H-quinoxalin-2-one-5-yl |
| 416 | ((2,4-difluorophenyl)ethyl)-1-piperazinyl | 3-isoquinolinol-8-yl |
| 417 | ((2-fluorophenyl)ethyl)-1-piperazinyl | 3-isoquinolinol-8-yl |
| 418 | ((3-fluorophenyl)ethyl)-1-piperazinyl | 3-isoquinolinol-8-yl |
| 419 | ((4-bromophenyl)ethyl)-1-piperazinyl | 3-isoquinolinol-8-yl |
| 420 | ((4-chlorophenyl)ethyl)-1-piperazinyl | 3-isoquinolinol-8-yl |
| 421 | ((4-fluorophenyl)ethyl)-1-piperazinyl | 3-isoquinolinol-8-yl |
| 422 | ((4-fluorophenyl)propyl)-3-methyl-1-piperazinyl | 3-isoquinolinol-8-yl |
| 423 | ((4-trifluoromethyl)phenyl)ethyl)-1-piperazinyl | 3-isoquinolinol-8-yl |
| 424 | 4-(1,1-dimethylethyl)-1-cyclohexen-1-yl | 3-isoquinolinol-8-yl |
| 425 | 4-(1,1-dimethylethyl)-1-cyclohexyl | 3-isoquinolinol-8-yl |
| 426 | 4-(trifluoromethyl)-1-cyclohexen-1-yl | 3-isoquinolinol-8-yl |
| 427 | 4-(trifluoromethyl)cyclohexyl | 3-isoquinolinol-8-yl |
| 428 | 1-[1-(4-fluoro-phenyl)-ethyl]-1,2,3,6-tetrahydro-pyridin-4-yl | 3-isoquinolinol-8-yl |
| 429 | 1-[1-(4-fluoro-phenyl)-ethyl]-piperidin-4-yl | 3-isoquinolinol-8-yl |
| 430 | ((2,4-difluorophenyl)ethyl)-1-piperazinyl | quinolin-7-yl |
| 431 | ((2-fluorophenyl)ethyl)-1-piperazinyl | quinolin-7-yl |
| 432 | ((3-fluorophenyl)ethyl)-1-piperazinyl | quinolin-7-yl |

TABLE 4-continued

| Ex # | Q | R⁴ |
|------|---|-----|
| 433 | ((4-bromophenyl)ethyl)-1-piperazinyl | quinolin-7-yl |
| 434 | ((4-chlorophenyl)ethyl)-1-piperazinyl | quinolin-7-yl |
| 435 | ((4-fluorophenyl)ethyl)-1-piperazinyl | quinolin-7-yl |
| 436 | ((4-fluorophenyl)propyl)-3-methyl-1-piperazinyl | quinolin-7-yl |
| 437 | ((4-trifluoromethyl)phenyl)ethyl)-1-piperazinyl | quinolin-7-yl |
| 438 | 4-(1,1-dimethylethyl)-1-cyclohexen-1-yl | quinolin-7-yl |
| 439 | 4-(1,1-dimethylethyl)-1-cyclohexyl | quinolin-7-yl |
| 440 | 4-(trifluoromethyl)-1-cyclohexen-1-yl | quinolin-7-yl |
| 441 | 4-(trifluoromethyl)cyclohexyl | quinolin-7-yl |
| 442 | 1-[1-(4-fluoro-phenyl)-ethyl]-1,2,3,6-tetrahydro-pyridin-4-yl | quinolin-7-yl |
| 443 | 1-[1-(4-fluoro-phenyl)-ethyl]-piperidin-4-yl | quinolin-7-yl |
| 444 | ((2,4-difluorophenyl)ethyl)-1-piperazinyl | quinolin-8-yl |
| 445 | ((2-fluorophenyl)ethyl)-1-piperazinyl | quinolin-8-yl |
| 446 | ((3-fluorophenyl)ethyl)-1-piperazinyl | quinolin-8-yl |
| 447 | ((4-bromophenyl)ethyl)-1-piperazinyl | quinolin-8-yl |
| 448 | ((4-chlorophenyl)ethyl)-1-piperazinyl | quinolin-8-yl |
| 449 | ((4-fluorophenyl)ethyl)-1-piperazinyl | quinolin-8-yl |
| 450 | ((4-fluorophenyl)propyl)-3-methyl-1-piperazinyl | quinolin-8-yl |
| 451 | ((4-trifluoromethyl)phenyl)ethyl)-1-piperazinyl | quinolin-8-yl |
| 452 | 4-(1,1-dimethylethyl)-1-cyclohexen-1-yl | quinolin-8-yl |
| 453 | 4-(1,1-dimethylethyl)-1-cyclohexyl | quinolin-8-yl |
| 454 | 4-(trifluoromethyl)-1-cyclohexen-1-yl | quinolin-8-yl |
| 455 | 4-(trifluoromethyl)cyclohexyl | quinolin-8-yl |
| 456 | 1-[1-(4-fluoro-phenyl)-ethyl]-1,2,3,6-tetrahydro-pyridin-4-yl | quinolin-8-yl |
| 457 | 1-[1-(4-fluoro-phenyl)-ethyl]-piperidin-4-yl | quinolin-8-yl |

TABLE 5

| Ex # | Q | R⁴ |
|------|---|-----|
| 459 | 4-(1,1-dimethylethyl)-1-cyclohexen-1-yl | 2-(amino)-1,3-benzothiazol-4-yl |
| 460 | 4-(1,1-dimethylethyl)-1-cyclohexen-1-yl | 2-aminoquinolin-8-yl |
| 461 | 4-(1,1-dimethylethyl)-1-cyclohexen-1-yl | 3,4-dihydro-2(1H)-quinoxalinone-5-yl |
| 462 | 4-(1,1-dimethylethyl)-1-cyclohexen-1-yl | 3-amino-1H-quinoxalin-2-one-5-yl |
| 463 | 4-(1,1-dimethylethyl)-1-cyclohexen-1-yl | 3-isoquinolinol-8-yl |
| 464 | 4-(1,1-dimethylethyl)-1-cyclohexen-1-yl | quinolin-7-yl |
| 465 | 4-(1,1-dimethylethyl)-1-cyclohexen-1-yl | quinolin-8-yl |
| 466 | 4-(1,1-dimethylethyl)-1-cyclohexyl | 2-(acetylamino)-1,3-benzothiazol-4-yl |
| 467 | 4-(1,1-dimethylethyl)-1-cyclohexyl | 2-(amino)-1,3-benzothiazol-4-yl |
| 468 | 4-(1,1-dimethylethyl)-1-cyclohexyl | 2-aminoquinolin-8-yl |
| 469 | 4-(1,1-dimethylethyl)-1-cyclohexyl | 3,4-dihydro-2(1H)-quinoxalinone-5-yl |
| 470 | 4-(1,1-dimethylethyl)-1-cyclohexyl | 3-amino-1H-quinoxalin-2-one-5-yl |
| 471 | 4-(1,1-dimethylethyl)-1-cyclohexyl | 3-isoquinolinol-8-yl |
| 472 | 4-(1,1-dimethylethyl)-1-cyclohexyl | quinolin-7-yl |
| 473 | 4-(1,1-dimethylethyl)-1-cyclohexyl | quinolin-8-yl |
| 476 | 4-(trifluoromethyl)-1-cyclohexen-1-yl | 2-aminoquinolin-8-yl |
| 477 | 4-(trifluoromethyl)-1-cyclohexen-1-yl | 3,4-dihydro-2(1H)-quinoxalinone-5-yl |
| 478 | 4-(trifluoromethyl)-1-cyclohexen-1-yl | 3-amino-1H-quinoxalin-2-one-5-yl |
| 479 | 4-(trifluoromethyl)-1-cyclohexen-1-yl | 3-isoquinolinol-8-yl |
| 480 | 4-(trifluoromethyl)-1-cyclohexen-1-yl | quinolin-7-yl |
| 481 | 4-(trifluoromethyl)-1-cyclohexen-1-yl | quinolin-8-yl |
| 483 | 4-(trifluoromethyl)cyclohexyl | 2-(amino)-1,3-benzothiazol-4-yl |
| 484 | 4-(trifluoromethyl)cyclohexyl | 2-aminoquinolin-8-yl |
| 485 | 4-(trifluoromethyl)cyclohexyl | 3,4-dihydro-2(1H)-quinoxalinone-5-yl |
| 486 | 4-(trifluoromethyl)cyclohexyl | 3-amino-1H-quinoxalin-2-one-5-yl |
| 487 | 4-(trifluoromethyl)cyclohexyl | 3-isoquinolinol-8-yl |
| 488 | 4-(trifluoromethyl)cyclohexyl | quinolin-7-yl |
| 489 | 4-(trifluoromethyl)cyclohexyl | quinolin-8-yl |

TABLE 6

| Ex # | Q | R⁴ |
|---|---|---|
| 490 | 4-(1,1-dimethylethyl)-1-cyclohexen-1-yl | 2-(acetylamino)-1,3-benzothiazol-4-yl |
| 491 | 4-(1,1-dimethylethyl)-1-cyclohexen-1-yl | 2-(amino)-1,3-benzothiazol-4-yl |
| 492 | 4-(1,1-dimethylethyl)-1-cyclohexen-1-yl | 2-aminoquinolin-8-yl |
| 493 | 4-(1,1-dimethylethyl)-1-cyclohexen-1-yl | 3,4-dihydro-2(1H)-quinoxalinone-5-yl |
| 494 | 4-(1,1-dimethylethyl)-1-cyclohexen-1-yl | 3-amino-1H-quinoxalin-2-one-5-yl |
| 495 | 4-(1,1-dimethylethyl)-1-cyclohexen-1-yl | 3-isoquinolinol-8-yl |
| 496 | 4-(1,1-dimethylethyl)-1-cyclohexen-1-yl | quinolin-7-yl |
| 497 | 4-(1,1-dimethylethyl)-1-cyclohexen-1-yl | quinolin-8-yl |
| 498 | 4-(1,1-dimethylethyl)-1-cyclohexyl | 2-(acetylamino)-1,3-benzothiazol-4-yl |
| 499 | 4-(1,1-dimethylethyl)-1-cyclohexyl | 2-(amino)-1,3-benzothiazol-4-yl |
| 500 | 4-(1,1-dimethylethyl)-1-cyclohexyl | 2-aminoquinolin-8-yl |
| 501 | 4-(1,1-dimethylethyl)-1-cyclohexyl | 3,4-dihydro-2(1H)-quinoxalinone-5-yl |
| 502 | 4-(1,1-dimethylethyl)-1-cyclohexyl | 3-amino-1H-quinoxalin-2-one-5-yl |
| 503 | 4-(1,1-dimethylethyl)-1-cyclohexyl | 3-isoquinolinol-8-yl |
| 504 | 4-(1,1-dimethylethyl)-1-cyclohexyl | quinolin-7-yl |
| 505 | 4-(1,1-dimethylethyl)-1-cyclohexyl | quinolin-8-yl |
| 506 | 4-(trifluoromethyl)-1-cyclohexen-1-yl | 2-(acetylamino)-1,3-benzothiazol-4-yl |
| 507 | 4-(trifluoromethyl)-1-cyclohexen-1-yl | 2-(amino)-1,3-benzothiazol-4-yl |
| 508 | 4-(trifluoromethyl)-1-cyclohexen-1-yl | 2-aminoquinolin-8-yl |
| 509 | 4-(trifluoromethyl)-1-cyclohexen-1-yl | 3,4-dihydro-2(1H)-quinoxalinone-5-yl |
| 510 | 4-(trifluoromethyl)-1-cyclohexen-1-yl | 3-amino-1H-quinoxalin-2-one-5-yl |
| 511 | 4-(trifluoromethyl)-1-cyclohexen-1-yl | 3-isoquinolinol-8-yl |
| 512 | 4-(trifluoromethyl)-1-cyclohexen-1-yl | quinolin-7-yl |
| 513 | 4-(trifluoromethyl)-1-cyclohexen-1-yl | quinolin-8-yl |
| 514 | 4-(trifluoromethyl)cyclohexyl | 2-(acetylamino)-1,3-benzothiazol-4-yl |
| 515 | 4-(trifluoromethyl)cyclohexyl | 2-(amino)-1,3-benzothiazol-4-yl |
| 516 | 4-(trifluoromethyl)cyclohexyl | 2-aminoquinolin-8-yl |
| 517 | 4-(trifluoromethyl)cyclohexyl | 3,4-dihydro-2(1H)-quinoxalinone-5-yl |
| 518 | 4-(trifluoromethyl)cyclohexyl | 3-amino-1H-quinoxalin-2-one-5-yl |
| 519 | 4-(trifluoromethyl)cyclohexyl | 3-isoquinolinol-8-yl |
| 520 | 4-(trifluoromethyl)cyclohexyl | quinolin-7-yl |
| 521 | 4-(trifluoromethyl)cyclohexyl | quinolin-8-yl |
| 522 | ((2,4-difluorophenyl)ethyl)-1-piperazinyl | 2-(acetylamino)-1,3-benzothiazol-4-yl |
| 523 | ((2-fluorophenyl)ethyl)-1-piperazinyl | 2-(acetylamino)-1,3-benzothiazol-4-yl |
| 524 | ((3-fluorophenyl)ethyl)-1-piperazinyl | 2-(acetylamino)-1,3-benzothiazol-4-yl |
| 525 | ((4-bromophenyl)ethyl)-1-piperazinyl | 2-(acetylamino)-1,3-benzothiazol-4-yl |
| 526 | ((4-chlorophenyl)ethyl)-1-piperazinyl | 2-(acetylamino)-1,3-benzothiazol-4-yl |
| 527 | ((4-fluorophenyl)ethyl)-1-piperazinyl | 2-(acetylamino)-1,3-benzothiazol-4-yl |
| 528 | ((4-fluorophenyl)propyl)-3-methyl-1-piperazinyl | 2-(acetylamino)-1,3-benzothiazol-4-yl |
| 529 | ((4-trifluoromethyl)phenyl)ethyl)-1-piperazinyl | 2-(acetylamino)-1,3-benzothiazol-4-yl |
| 530 | 4-(1,1-dimethylethyl)-1-cyclohexen-1-yl | 2-(acetylamino)-1,3-benzothiazol-4-yl |
| 531 | 4-(1,1-dimethylethyl)-1-cyclohexyl | 2-(acetylamino)-1,3-benzothiazol-4-yl |

Capsaicin-induced $Ca^{2+}$ Influx in Primary Dorsal Root Ganglion Neurons

Embryonic 19 day old (E19) dorsal root ganglia (DRG) were dissected from timed-pregnant, terminally anesthetized Sprague-Dawley rats (Charles River, Wilmington, Mass.) and collected in ice-cold L-15 media (Life Technologies, Grand Island, N.Y.) containing 5% heat inactivated horse serum (Life Technologies). The DRG were then dissociated into single cell suspension using a papain dissociation system (Worthington Biochemical Corp., Freehold, N.J.). The dissociated cells were pelleted at 200×g for 5 min and re-suspended in EBSS containing 1 mg/mL ovomucoid inhibitor, 1 mg/mL ovalbumin and 0.005% DNase. Cell suspension was centrifuged through a gradient solution containing 10 mg/mL ovomucoid inhibitor, 10 mg/mL ovalbumin at 200×g for 6 min to remove cell debris; and filtered through a 88-μm nylon mesh (Fisher Scientific, Pittsburgh, Pa.) to remove any clumps. Cell number was determined with a hemocytometer and cells were seeded into poly-ornithine 100 μg/mL (Sigma) and mouse laminin 1 μg/mL (Life Technologies)-coated 96-well plates at 10×10³ cells/well in complete medium. The complete medium consists of minimal essential medium (MEM) and Ham's F12, 1:1, penicillin (100 U/mL), and streptomycin (100 μg/mL), and nerve growth factor (10 ng/mL), 10% heat inactivated horse serum (Life Technologies). The cultures were kept at 37° C., 5% $CO_2$ and 100% humidity. For controlling the growth of non-neuronal cells, 5-fluoro-2'-deoxyuridine (75 μM) and uridine (180 μM) were included in the medium. Activation of VR1 was achieved in these cellular assays using either a capsaicin stimulus (ranging from 0.01-10 μM) or by an acid stimulus (addition of 30 mM Hepes/Mes buffered at pH 4.1). Compounds were also tested in an assay format to evaluate their agonist properties at VR1. The activation of VR1 is followed as a function of cellular uptake of radioactive calcium ($^{45}Ca^{2+}$:Amersham CES3-2mCi).

Capsaicin Antagonist Assay: E-19 DRG cells at 3 days in culture are incubated with serial concentrations of VR1 antagonists, in HBSS (Hanks buffered saline solution supplemented with BSA 0.1 mg/mL and 1 mM Hepes at pH 7.4) for 15 min, room temperature. Cells are then challenged with a VR1 agonist, capsaicin (500 nM), in activation buffer containing 0.1 mg/mL BSA, 15 mM Hepes, pH 7.4, and 10 µCi/mL $^{45}Ca^{2+}$ (Amersham CES3-2mCi) in Ham's F12 for 2 min at room temperature.

Acid Antagonist Assay: Compounds are pre-incubated with E-19 DRG cells at room temperature for 2 minutes prior to addition of $^{45}Ca^{2+}$ in 30 mM Hepes/Mes buffer (Final Assay pH 5) and then left for an additional 2 minutes prior to compound washout. Final concentration of $^{45}Ca^{2+}$ (Amersham CES3-2mCi) is 10 µCi/mL.

Agonist Assay: Compounds are incubated with E-19 DRG cells at room temperature for 2 minutes in the presence of $^{45}Ca^{2+}$ prior to compound washout. Final $^{45}Ca^{2+}$ (Amersham CES3-2mCi) at 10 µCi/mL.

Compound Washout and Analysis: Assay plates are washed using an ELX405 plate washer (Bio-Tek Instruments Inc.) immediately after functional assay. Wash 3× with PBS, 0.1 mg/mL BSA. Aspirate between washes. R$^e$ ad plates using a MicroBeta Jet (Wallac Inc.). Compound activity is then calculated using appropriate computational algorithms.

$^{45}$Calcium$^{2+}$ Assay Protocol

Compounds may be assayed using Chinese Hamster Ovary cell lines stably expressing either human VR1 or rat VR1 under a CMV promoter. Cells could be cultured in a Growth Medium, routinely passaged at 70% confluency using trypsin and plated in an assay plate 24 hours prior to compound evaluation.

Possible Growth Medium:
DMEM, high glucose (Gibco 11965-084).
10% Dialyzed serum (Hyclone SH30079.03).
1×Non-Essential Amino Acids (Gibco 11140-050).
1×Glutamine-Pen-Strep (Gibco 10378-016).
Geneticin, 450/g/mL (Gibco 10131-035).

Compounds could be diluted in 100% DMSO and tested for activity over several log units of concentration [40 µM-2 pM]. Compounds may be further diluted in HBSS buffer (pH 7.4) 0.1 mg/mL BSA, prior to evaluation. Final DMSO concentration in assay would be 0.5-1%. Each assay plate could be controlled with a buffer only and a known antagonist compound (either capsazepine or one of the described VR1 antagonists).

Activation of VR1 could be achieved in these cellular assays using either a capsaicin stimulus (ranging from 0.1-1 µM) or by an acid stimulus (addition of 30 mM Hepes/Mes buffered at pH 4.1). Compounds could also be tested in an assay format to evaluate their agonist properties at VR1.

Capsaicin Antagonist Assay: Compounds may be pre-incubated with cells (expressing either human or rat VR1) at room temperature for 2 minutes prior to addition of $^{45}Ca^{2+}$ and Capsaicin and then left for an additional 2 minutes prior to compound washout. Capsaicin (200 nM) can be added in HAM's F12, 0.1 mg/mL BSA, 15 mM Hepes at pH 7.4. Final $^{45}Ca^{2+}$ (Amersham CES3-2mCi) added could be 10 µCi/mL. The following compounds exhibit IC50 values of less than 10 mM in the Human VR1 Capsaicin Antagonist Assay:

4-((6-(4-(1,1-dimethylethyl)-1-cyclohexen-1-yl)$_4$-pyrimidinyl)oxy)-1,3-benzothiazol-2-amine;
4-((6-(4-(trifluoromethyl)-1-cyclohexen-1-yl)-4-pyrimidinyl)oxy)-1,3-benzothiazol-2-amine;
5-[(6-{4-[(1R)-1-(4-fluorophenyl)ethyl]piperazin-1-yl}pyrimidin-4-yl)amino]-2H-1,4-benzoxazin-3(4H)-one;
5-[(6-{4-[(1S)-1-(4-fluorophenyl)ethyl]piperazin-1-yl}pyrimidin-4-yl)amino]-1,3-dihydro-2H-indol-2-one;
6-[(6-{4-[(1S)-1-(4-fluorophenyl)ethyl]piperazin-1-yl}pyrimidin-4-yl)amino]-2H-1,4-benzoxazin-3(4H)-one;
7-[(6-{4-[(1S)-1-(4-fluorophenyl)ethyl]piperazin-1-yl}pyrimidin-4-yl)amino]-3,4-dihydroquinolin-2(1H)-one;
N-(2,3-dihydro-1,4-benzodioxin-6-yl)-6-{4-[(1S)-1-(4-fluorophenyl)ethyl]piperazin-1-yl}pyrimidin-4-amine;
N-(4-((6-(4-((1R)-1-(4-fluorophenyl)ethyl)-1-piperazinyl)$_4$-pyrimidinyl)amino)-1,3-benzothiazol-2-yl)acetamide;
N-(4-((6-(4-(1,1-dimethylethyl)-1-cyclohexen-1-yl)$_4$-pyrimidinyl)oxy)-1,3-benzothiazol-2-yl)acetamide;
N-(4-((6-(4-(trifluoromethyl)-1-cyclohexen-1-yl)$_4$-pyrimidinyl)oxy)-1,3-benzothiazol-2-yl)acetamide;
N-(4-((6-(4-(trifluoromethyl)Cyclohexyl)$_4$-pyrimidinyl)oxy)-1,3-benzothiazol-2-yl)acetamide;
N-(6-(4-((1R)-1-(4-fluorophenyl)ethyl)-1-piperazinyl)$_4$-pyrimidinyl)-7-quinolinamine;
N-(6-(4-((1S)-1-(4-fluorophenyl)ethyl)-1-piperazinyl)$_4$-pyrimidinyl)-7-quinolinamine;
N-(6-{4-[(1S)-1-(4-fluorophenyl)ethyl]piperazin-1-yl}pyrimidin-4-yl)-1,3-benzothiazol-5-amine;
N-[4-({4-[4-(trifluoromethyl)Cyclohex-1-en-1-yl]pyridin-2-yl}oxy)-1,3-benzothiazol-2-yl]acetamide;
N-{4-[(4-{4-[(1S)-1-(4-fluorophenyl)ethyl]piperazin-1-yl}pyridin-2-yl)oxy]-1,3-benzothiazol-2-yl}acetamide; and
tert-butyl 2'-{[2-(acetylamino)-1,3-benzothiazol-4-yl]oxy}-3,6-dihydro-4,4'-bipyridine-1 (2H)-carboxylate.

Acid Antagonist Assay: Compounds can be pre-incubated with cells (expressing either human or rat VR1) for 2 minutes prior to addition of $^{45}Ca^{2+}$ in 30 mM Hepes/Mes buffer (Final Assay pH 5) and then left for an additional 2 minutes prior to compound washout. Final $^{45}Ca^{2+}$ (Amersham CES3-2mCi) added could be 10 µCi/mL.

Agonist Assay: Compounds can be incubated with cells (expressing either human or rat VR1) for 2 minutes in the presence of $^{45}Ca^{2+}$ prior to compound washout. Final $^{45}Ca^{2+}$ (Amersham CES3-2mCi) added could be 10 µCi/mL.

Compound Washout and Analysis: Assay plates would be washed using an ELX405 plate washer (Bio-Tek Instruments Inc.) immediately after the functional assay. One could wash 3× with PBS, 0.1 mg/mL BSA, aspirating between washes. Plates could then be read using a MicroBeta Jet (Wallac Inc.) and compound activity calculated using appropriate computational algorithms.

Useful nucleic acid sequences and proteins may be found in U.S. Pat. Nos. 6,335,180, 6, 406,908 and 6,239,267, herein incorporated by reference in their entirety.

For the treatment of vanilloid-receptor-diseases, such as acute, inflammatory and neuropathic pain, dental pain, general headache, migraine, cluster headache, mixed-vascular and non-vascular syndromes, tension headache, general inflammation, arthritis, rheumatic diseases, osteoarthritis, inflammatory bowel disorders, inflammatory eye disorders, inflammatory or unstable bladder disorders, psoriasis, skin complaints with inflammatory components, chronic inflammatory conditions, inflammatory pain and associated hyperalgesia and allodynia, neuropathic pain and associated hyperalgesia and allodynia, diabetic neuropathy pain, causalgia, sympathetically maintained pain, deafferentation syndromes, asthma, epithelial tissue damage or dysfunction, herpes simplex, disturbances of visceral motility at respiratory, genitourinary, gastrointestinal or vascular regions, wounds, burns, allergic skin reactions, pruritis, vitiligo, general gastrointestinal disorders, gastric ulceration, duodenal ulcers, diarrhea, gastric lesions induced by necrotising agents, hair growth, vasomotor or allergic rhinitis, bronchial disorders or bladder disorders, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating vanilloid-receptor-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, isopropoxymethyl, α-methoxyethyl, groups such as α-(($C_1$-$C_4$) alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3,dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

We claim:
1. A compound having the structure:

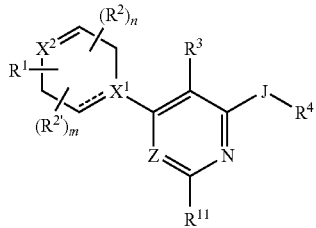

or any pharmaceutically-acceptable salt thereof, wherein:
  ⌁ represents a single or double bond;
  J is NH, O or S;
  $X^1$ is N or C;
  $X^2$ is N or C;
  n 0, 1 or 2;
  m is 0 or 1;
wherein
  A) when $X^1$ and $X^2$ are both C
    $R^1$ is —$OR^a$, —$OR^c$, —$NR^aR^a$, —$NR^aR^c$, —$SR^b$, —$SR^c$, —S(=O)$R^b$, —S(=O)$R^c$, —S(=O)$_2R^b$, —S(=O)$_2R^c$ or $C_{1-6}$alkyl substituted by 0, 1, 2 or 3 substituents independently selected from $C_{1-4}$haloalkyl, halo, cyano, oxo, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and additionally substituted by 0 or 1 substituents selected from a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and the ring is additionally substituted by 0, 1, 2, 3, 4 or 5 substituents independently selected from Br, Cl, F and I; or $R^1$ is $C_{1-6}$heteroalkyl chain substituted by 0, 1, 2 or 3 substituents independently selected from $C_{1-4}$haloalkyl, halo, cyano, oxo, nitro, —C(=O)$R^b$, —C(=O)O$R^b$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^a$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$ alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2$ $R^b$, —N($R^a$)S(=O)$_2$N$R^aR^a$, —N$R^a$C$_{2-6}$ alkylN$R^aR^a$ and —N$R^a$C$_{2-6}$alkylO$R^a$;

B) when at least one of $X^1$ and $X^2$ is N, and J is NH, then
  $R^1$ is $C_{1-6}$alkyl substituted by 0, 1, 2 or 3 substituents independently selected from $C_{1-4}$haloalkyl, halo, cyano, oxo, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^a$C$_{2-6}$alkylN$R^aR^a$ and —N$R^a$C$_{2-6}$alkylO$R^a$, and additionally substituted by a substituent selected from
  i) a saturated, partially saturated or unsaturated 5-, 6- or 7-membered monocyclic ring containing 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^{15}$, —OC(=O)N$R^aR^a$, —OC(=O)N($R^a$)S(=O)$_2R^b$, —OC$_{2-6}$ alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2$ $R^b$, —N($R^a$)S(=O)$_2$N$R^aR^a$, —N$R^a$C$_{2-6}$ alkylN$R^aR^a$ and —N$R^a$C$_{2-6}$alkylO$R^a$, and the ring is additionally substituted by 0, 1, 2, 3, 4 or 5 substituents independently selected from Br, Cl, F and I;

ii) a saturated, partially saturated or unsaturated 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $C_{1-8}$alkyl, $C_{1-4}$haloalkyl, halo, cyano, nitro, —C(=)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and the ring is additionally substituted by 0, 1, 2, 3, 4 or 5 substituents independently selected from Br, Cl, F and I; and iii) a saturated, partially saturated or unsaturated 6-membered monocyclic carbocyclic ring or a 9-, 10- or 11-membered bicyclic carbocyclic ring substituted by 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —C(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$; or $R^1$ is $C_{1-6}$heteroalkyl chain substituted by 0, 1, 2 or 3 substituents independently selected from $C_{1-4}$haloalkyl, halo, cyano, oxo, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and additionally substituted by a saturated, partially saturated or unsaturated 5-, 6- or 7-membered monocyclic or 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and the ring is additionally substituted by 0, 1, 2, 3, 4 or 5 substituents independently selected from Br, Cl, F and I; or $R^1$ is —O$R^a$, —O$R^c$, —N$R^aR^a$, —N$R^aR^c$, —S$R^b$, —S$R^c$, —S(=O)$R^b$, —S(=O)$R^c$, —S(=O)$_2R^b$ or —S(=O)$_2R^c$, and C) when at least one of $X^1$ and $X^2$ is N, and J is O, then Y and Z are both CH; and $R^1$ is $C_{1-6}$alkyl substituted by 0, 1, 2 or 3 substituents independently selected from $C_{1-4}$haloalkyl, halo, cyano, oxo, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and additionally substituted by a saturated, partially saturated or unsaturated 5-, 6- or 7-membered monocyclic or 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and the ring is additionally substituted by 0, 1, 2, 3, 4 or 5 substituents independently selected from Br, Cl, F and I; or $R^1$ is $C_{1-6}$heteroalkyl chain substituted by 0, 1, 2 or 3 substituents independently selected from $C_{1-4}$haloalkyl, halo, cyano, oxo, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and additionally substituted by a saturated, partially saturated or unsaturated 5-, 6- or 7-membered monocyclic or 6-, 7-, 8-, 9-, 10- or 11-membered bicyclic ring containing 1, 2, 3 or 4 atoms selected from N, O and S, wherein the carbon atoms of the ring are substituted by 0, 1 or 2 oxo or thioxo groups, sulfur atoms of the ring are substituted by 0, 1 or 2 oxo groups, nitrogen atoms of the ring are substituted by 0 or 1 oxo groups, and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$ alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2$ $R^b$, —N($R^a$)S(=O)$_2$N$R^aR^a$, —N$R^aC_{2-6}$alkylN$R^aR^a$ and —N$R^aC_{2-6}$alkylO$R^a$, and the ring is additionally substituted by 0, 1, 2, 3, 4 or 5 substituents independently selected from Br, Cl, F and I; or $R^1$ is —O$R^a$, —O$R^c$, —N$R^aR^a$, —N$R^aR^c$, —S$R^b$, —S$R^c$, —S(=O)$R^b$, —S(=O)$R^c$, —S(=O)$_2R^b$ or —S(=O)$_2R^c$;

$R^2$ is, independently, in each instance, $C_{1-6}$alkyl, $C_{1-4}$haloalkyl, F, Cl, or Br;

$R^{2'}$ is —O$R^b$, —N$R^aR^b$, —S$R^b$, —S(=O)$R^b$, —S(=O)$_2$ $R^b$ or $C_{1-6}$alkyl substituted by 0, 1, 2 or 3 substituents independently selected from $C_{1-4}$haloalkyl, halo, cyano, oxo, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$ N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and additionally substituted by 0 or 1 substituents selected from a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$; or $R^{2'}$ is $C_{1-6}$heteroalkyl chain substituted by 0, 1 or 2 substituents independently selected from $C_{1-4}$haloalkyl, halo, cyano, oxo, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$alkylN$R^aR^a$, —OC$_{2-6}$alkylO$R^a$, —S$R^a$, —S(=O)$R^b$, —S(=O)$_2$ $R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$ N$R^aR^a$, —N$R^aC_{2-6}$alkylN$R^aR^a$ and —N$R^aC_{2-6}$alkylO$R^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —OC$_{2-6}$ alkylN$R^aR^a$, —OC$_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2$ $R^b$, —N($R^a$)S(=O)$_2$N$R^aR^a$, —N$R^aC_{2-6}$ alkylN$R^aR^a$ and —N$R^aC_{2-6}$alkylO$R^a$;

$R^4$ is

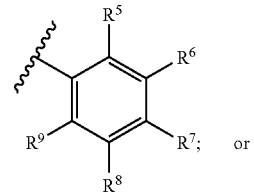

$R^4$ is a saturated or unsaturated 5- or 6-membered ring heterocycle containing 1, 2 or 3 atoms selected from O, N and S that is optionally vicinally fused with a saturated or unsaturated 3- or 4-atom bridge containing 0, 1, 2 or 3 atoms selected from O, N and S with the remaining atoms being carbon, so long as the combination of O and S atoms is not greater than 2, wherein the carbon atoms of the heterocycle and bridge are substituted by 0, 1, 2 or 3 substituents independently selected from $R^e$, $C_{1-4}$haloalkyl, halo, nitro, cyano, oxo, —O$R^f$, —S(=O)$_nR^e$, —OC$_{1-4}$haloalkyl, —OC$_{2-6}$alkylN$R^aR^f$, —OC$_{2-6}$alkylO$R^f$, —OC$_{1-6}$alkylC(=O)O$R^e$, —N$R^aR^f$, —N$R^aC_{1-4}$haloalkyl, —OC$_{2-6}$alkylN$R^aR^f$, —N$R^aC_{2-6}$alkylO$R^f$, —C(=O)$R^e$, —C(=O)O$R^e$, —OC(=O)$R^e$, —C(=O)N$R^aR^f$ and —N$R^aC$(=O)$R^e$; and unsaturated carbon atoms may be additionally substituted by =O; and any available nitrogen atoms in the heterocycle and bridge are substituted by H, —C$_{1-6}$alkylO$R^f$, $R^e$, —C$_{1-6}$alkylN$R^aR^f$, —C$_{1-3}$alkylC(=O)O$R^e$, —C$_{1-3}$alkylC(=O)N$R^aR^f$, —C$_{1-3}$alkylOC(=O)$R^e$, —C$_{1-3}$alkylN$R^aC$(=O)$R^e$, —C(=O)$R^c$ or —C$_{1-3}$alkyl$R^c$; or $R^4$ is naphthyl substituted by 1, 2 or 3 substituents independently selected from $C_{1-4}$haloalkyl, halo, nitro, cyano, —S(=O)$_nR^e$, —OC$_{1-4}$haloalkyl, —OC$_{2-6}$alkylN$R^aR^f$, —OC$_{2-6}$alkylO$R^f$, —OC$_{1-6}$alkylC(=O)O$R^e$, —N$R^aC_{1-4}$haloalkyl, —N$R^aC_{2-6}$alkylN$R^aR^f$, —N$R^aC_{2-6}$alkylO$R^f$, —C(=O)$R^e$, —C(=O)O$R^e$, —OC(=O)$R^e$ and —C(=O)N$R^aR^f$;

$R^5$ is independently, at each instance, selected from H, $C_{1-8}$alkyl, $C_{1-4}$haloalkyl, halo, cyano, nitro, —C(=O)($R^b$), —C(=O)O($R^b$), —C(=O)N$R^aR^a$, —C(=N$R^a$)N$R^aR^a$, —O$R^a$, —OC(=O)($R^b$), —OC(=O)N$R^aR^a$, —OC(=O)N($R^a$)S(=O)$_2$($R^b$), —OC$_{2-6}$alkylN$R^aR^a$, —OC$_{2-6}$alkylO$R^a$, —S$R^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^5$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^5$ is C$_{1-4}$alkyl substituted by 0, 1, 2 or 3 groups selected from C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —C(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^6$ is independently, at each instance, selected from H, C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^6$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^6$ is C$_{1-4}$alkyl substituted by 0, 1, 2 or 3 groups selected from C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^5$ and R$^6$ together are a saturated, partially-saturated or unsaturated 3-, 4- or 5-atom bridge containing 1, 2 or 3 atoms selected from O, N and S with the remaining atoms being carbon, so long as the combination of O and S atoms is not greater than 2, wherein the bridge is substituted by 0, 1 or 2 substituents selected from oxo, thioxo, R$^e$, halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R$^f$, —NR$^f$C$_{2-6}$alkylNR$^a$R$^f$ and —NR$^f$C$_{2-6}$alkylOR$^f$;

R$^7$ is independently, at each instance, selected from H, C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^7$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$ alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^7$ is C$_{1-4}$alkyl substituted by 0, 1, 2 or 3 groups selected from C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^6$ and R$^7$ together are a saturated or unsaturated 3- or 4-atom bridge containing 1, 2 or 3 atoms selected from O, N and S with the remaining atoms being carbon, so long as the combination of O and S atoms is not greater than 2, wherein the bridge is substituted by 0, 1, 2 or 3 substituents selected from =O, R$^e$, halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —C(=O)NR$^a$R$^f$, —OC(=O)N(R$^f$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^f$)C(=O)R$^e$, —S(=O)$_2$N(R$^f$)C(=O)OR$^e$, —S(=O)$_2$N(R$^f$)C(=O)NR$^a$R$^f$, —NR$^a$R$^f$, —N(R$^f$)C(=O)R$^e$, —N(R$^f$)C(=O)OR$^e$, —N(R$^f$)C(=O)NR$^a$R$^f$, —N(R$^f$)C(=NR$^a$)NR$^a$R$^f$, —N(R$^f$)S(=O)$_2$R$^e$, —N(R$^f$)S(=O)$_2$NR$^a$R, —NR$^f$C$_{2-6}$alkylNR$^a$R$^f$ and —NR$^f$C$_{2-6}$alkylOR$^f$;

R$^8$ is independently, at each instance, selected from H, C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^8$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^8$ is C$_{1-4}$alkyl substituted by 0, 1, 2 or 3 groups selected from C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$;

R$^9$ is independently, at each instance, selected from H, C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^9$ is a saturated or unsaturated 5-, 6- or 7-membered monocyclic or 6-, 7-, 8-, 9-, 10- or 11-membered bicyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein the carbon atoms of the ring are substituted by 0, 1 or 2 oxo groups, wherein the ring is substituted by 0, 1, 2 or 3 groups selected from C$_{1-8}$alkyl, C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^9$ is C$_{1-4}$alkyl substituted by 0, 1, 2 or 3 groups selected from C$_{1-4}$haloalkyl, halo, cyano, nitro, —C(=O)(R$^b$), —C(=O)O(R$^b$), —C(=O)NR$^a$R$^a$, —C(=NR$^a$)NR$^a$R$^a$, —OR$^a$, —OC(=O)(R$^b$), —OC(=O)NR$^a$R$^a$, —OC(=O)N(R$^a$)S(=O)$_2$(R$^b$), —OC$_{2-6}$alkylNR$^a$R$^a$, —OC$_{2-6}$alkylOR$^a$, —SR$^a$, —S(=O)(R$^b$), —S(=O)$_2$(R$^b$), —S(=O)$_2$NR$^a$R$^a$, —S(=O)$_2$N(R$^a$)C(=O)(R$^b$), —S(=O)$_2$N(R$^a$)C(=O)O(R$^b$), —S(=O)$_2$N(R$^a$)C(=O)NR$^a$R$^a$, —NR$^a$R$^a$, —N(R$^a$)C(=O)(R$^b$), —N(R$^a$)C(=O)O(R$^b$), —N(R$^a$)C(=O)NR$^a$R$^a$, —N(R$^a$)C(=NR$^a$)NR$^a$R$^a$, —N(R$^a$)S(=O)$_2$(R$^b$), —N(R$^a$)S(=O)$_2$NR$^a$R$^a$, —NR$^a$C$_{2-6}$alkylNR$^a$R$^a$ and —NR$^a$C$_{2-6}$alkylOR$^a$; wherein at least one of R$^5$, R$^6$, R$^7$, R$^8$ and R$^9$ is other than H;

$R^{11}$ is
- (A) $C_{1-8}$alkyl substituted by 0, 1, 2 or 3 substituents independently selected from halo, nitro, cyano, —$OR^m$, —$OR^n$, —$OC_{2-6}$alkylNR$^a$R$^m$, —$OC_{2-6}$alkylOR$^m$, —NR$^a$R$^m$, —NR$^a$R$^n$, —NR$^m$C$_{2-6}$alkylNR$^a$R$^m$, —NR$^m$C$_{2-6}$alkylOR$^m$, —CO$_2$R$^k$, —C(=O)R$^k$, —C(=O)NR$^a$R$^m$, —C(=O)NR$^a$R$^n$, —NR$^m$C(=O)R$^k$, —NR$^m$C(=O)R$^k$, —NR$^m$C(=O)NR$^a$R$^m$, —NR$^m$CO$_2$R$^k$, —C$_{1-8}$alkylOR$^m$, —C$_{1-6}$alkylNR$^a$R$^m$, —S(=O)$_n$R$^k$, —S(=O)$_2$NR$^a$R$^m$, —NR$^a$S(=O)$_2$R$^k$ and —OC(=O)NR$^a$R$^m$, and additionally substituted by 0, 1 or 2R$^i$ groups, and additionally substituted by 0, 1, 2, 3, 4 or 5 substituents independently selected from Br, Cl, F and I; or
- (B) a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 0, 1, 2 or 3 substituents independently selected from R$^k$, R$^h$, halo, nitro, cyano, —OR$^k$, —OR$^n$, —OC$_{2-6}$alkylNR$^a$R$^m$, —OC$_{2-6}$alkylOR$^m$, —NR$^a$R$^m$, —NR$^a$R$^n$, —NR$^m$C$_{2-6}$alkylNR$^a$R$^m$, —NR$^m$C$_{2-6}$alkylOR$^m$, naphthyl, —CO$_2$R$^k$, —C(=O)R$^k$, —C(=O)NR$^a$R$^m$, —C(=O)NR$^a$R$^n$, —NR$^m$C(=O)R$^k$, —NR$^m$C(=O)R$^n$, —NR$^m$C(=O)NR$^a$R$^m$, —NR$^m$CO$_2$R$^k$, —C$_{1-8}$alkylOR$^m$, —C$_{1-6}$alkylNR$^a$R$^m$, —S(=O)$_n$R$^k$, —S(=O)$_2$NR$^a$R$^m$, —NR$^a$S(=O)$_2$R$^k$ and —OC(=O)NR$^a$R$^m$, and the ring is additionally substituted by 0, 1, 2, 3, 4 or 5 substituents independently selected from Br, Cl, F and I; or
- (C) —N(R$^a$)—C$_{1-8}$alkyl, wherein the C$_{1-8}$alkyl is substituted by 0, 1, 2 or 3 substituents independently selected from R$^h$, halo, nitro, cyano, —OR$^k$, —OR$^n$, —OC$_{2-6}$alkylNR$^a$R$^m$, —OC$_{2-6}$alkylOR$^m$, —NR$^a$R$^m$, —NR$^a$R$^n$, —NR$^m$C$_{2-6}$alkylNR$^a$R$^m$, —NR$^m$C$_{2-6}$alkylOR$^m$, naphthyl, —CO$_2$R$^k$, —C(=O)R$^k$, —C(=O)NR$^a$R$^m$, —C(=O)NR$^a$R$^n$, —NR$^m$C(=O)R$^k$, —NR$^m$C(=O)R$^n$, —NR$^m$C(=O)NR$^a$R$^m$, —NR$^m$CO$_2$R$^k$, —C$_{1-8}$alkylOR$^m$, —C$_{1-6}$alkylNR$^a$R$^k$, —S(=O)$_n$R$^k$, —S(=O)$_2$NR$^a$R$^m$, —NR$^a$S(=O)$_2$R$^k$ and —OC(=O)NR$^a$R$^m$, and additionally substituted by 0, 1, 2, 3, 4 or 5 substituents independently selected from Br, Cl, F and I; or
- (D) —OC$_{1-8}$alkyl, wherein the C$_{1-8}$alkyl is substituted by 0, 1, 2 or 3 substituents independently selected from R$^k$, R$^h$, halo, nitro, cyano, —OR$^k$, —OC$_{2-6}$alkylNR$^a$R$^m$, —OC$_{2-6}$alkylOR$^m$, —NR$^a$R$^m$, —NR$^a$R$^n$, —NR$^m$C$_{2-6}$alkylNR$^a$R$^m$, —NR$^m$C$_{2-6}$alkylOR$^m$, naphthyl, —CO$_2$R$^k$, —C(=O)R$^k$, —C(=O)NR$^a$R$^m$, —C(=O)NR$^a$R$^n$, —NR$^m$C(=O)R$^k$, —NR$^m$C(=O)R$^n$, —NR$^m$C(=O)NR$^a$R$^m$, —NR$^m$CO$_2$R$^k$, —C$_{1-8}$alkylOR$^m$, —C$_{1-6}$alkylNR$^a$R$^m$, —S(=O)$_n$R$^k$, —S(=O)$_2$NR$^a$R$^m$, —NR$^a$S(=O)$_2$R$^k$ and —C(=O)NR$^a$R$^m$, and additionally substituted by 0, 1, 2, 3, 4 or 5 substituents independently selected from Br, Cl, F and I; or
- (E) H, cyano, —OR$^i$, —SR$^i$, —N(R$^a$)R$^i$, —OH or —NH$_2$;

$R^a$ is independently, at each instance, H or R$^b$;

$R^b$ is independently, at each instance, phenyl, benzyl or C$_{1-6}$alkyl, the phenyl, benzyl and C$_{1-6}$alkyl being substituted by 0, 1, 2 or 3 substituents selected from halo, C$_{1-4}$alkyl, C$_{1-3}$haloalkyl, —OC$_{1-4}$alkyl, OH, —NH$_2$, —NHC$_{1-4}$alkyl, —N(C$_{1-4}$alkyl)C$_{1-4}$alkyl;

$R^c$ is independently, in each instance, phenyl substituted by 0, 1 or 2 groups selected from halo, C$_{1-4}$alkyl, C$_{1-3}$haloalkyl, —OR$^a$ and —NR$^a$R$^a$; or R$^c$ is a saturated or unsaturated 5- or 6-membered ring heterocycle containing 1, 2 or 3 heteroatoms independently selected from N, O and S, wherein no more than 2 of the ring members are O or S, wherein the heterocycle is optionally fused with a phenyl ring, and the carbon atoms of the heterocycle are substituted by 0, 1 or 2 oxo groups, wherein the heterocycle or fused phenyl ring is substituted by 0, 1, 2 or 3 substituents selected from halo, C$_{1-4}$alkyl, C$_{1-3}$haloalkyl, —OR$^a$ and —NR$^a$R$^a$;

$R^e$ is, independently, in each instance, C$_{1-9}$alkyl substituted by 0, 1, 2, 3 or 4 substituents selected from halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; and wherein the C$_{1-9}$alkyl is additionally substituted by 0 or 1 groups independently selected from R$^g$;

$R^f$ is, independently, in each instance, R$^e$ or H;

$R^g$ is, independently, in each instance, a saturated or unsaturated 5- or 6-membered monocyclic ring containing 1, 2 or 3 atoms selected from N, O and S, so long as the combination of O and S atoms is not greater than 2, wherein the carbon atoms of the ring are substituted by 0 or 1 oxo groups;

$R^h$ is, independently, in each instance, phenyl or a saturated, partially saturated or unsaturated 5- or 6-membered monocyclic ring containing 1, 2 or 3 atoms selected from N, O and S, so long as the combination of O and S atoms is not greater than 2, wherein the ring is substituted by 0 or 1 oxo or thioxo groups, wherein the phenyl or monocycle are substituted by 0, 1, 2 or 3 substituents selected from halo, cyano, nitro, —C(=O)R$^e$, —C(=O)OR$^e$, —C(=O)NR$^a$R$^f$, —C(=NR$^a$)NR$^a$R$^f$, —OR$^f$, —OC(=O)R$^e$, —OC(=O)NR$^a$R$^f$, —OC(=O)N(R$^a$)S(=O)$_2$R$^e$, —OC$_{2-6}$alkylNR$^a$R$^f$, —OC$_{2-6}$alkylOR$^f$, —SR$^f$, —S(=O)R$^e$, —S(=O)$_2$R$^e$, —S(=O)$_2$NR$^a$R$^f$, —S(=O)$_2$N(R$^a$)C(=O)R$^e$, —S(=O)$_2$N(R$^a$)C(=O)OR$^e$, —S(=O)$_2$N(R$^a$)C(=O)NR$^a$R$^f$, —NR$^a$R$^f$, —N(R$^a$)C(=O)R$^e$, —N(R$^a$)C(=O)OR$^e$, —N(R$^a$)C(=O)NR$^a$R$^f$, —N(R$^a$)C(=NR$^a$)NR$^a$R$^f$, —N(R$^a$)S(=O)$_2$R$^e$, —N(R$^a$)S(=O)$_2$NR$^a$R$^f$, —NR$^a$C$_{2-6}$alkylNR$^a$ and —NR$^a$C$_{2-6}$alkylOR$^f$;

$R^i$ is a saturated, partially saturated or unsaturated 5-, 6- or 7-membered monocyclic or 6-, 7-, 8-, 9-, 10- or 11-membered bicyclic ring containing 0, 1, 2, 3 or 4 atoms selected from N, O and S, wherein the available carbon atoms of the ring are substituted by 0, 1 or 2 oxo or thioxo groups, wherein the ring is substituted by 0, 1, 2 or 3 substituents independently selected from R$^f$, R$^g$, R$^c$, halo, nitro, cyano, —OR$^e$, —OR$^g$, —OC$_{2-6}$alkylNR$^a$R$^f$, —OC$_{2-6}$alkylOR$^f$, —NR$^a$R$^f$, —NR$^a$R$^g$, —NR$^f$C$_{2-6}$alkylNR$^a$R$^f$, —NR$^f$C$_{2-6}$alkylOR$^f$, naphthyl, —CO$_2$R$^e$, —C(=O)R$^e$, —C(=O)NR$^f$R$^e$, —C(=O)NR$^f$R$^g$, —NR$^f$C(=O)R$^e$, —NR$^f$C(=O)R$^g$, —NR$^f$C(=O)NR$^a$R$^f$, —NR$^f$CO$_2$R$^e$, —C$_{1-1}$ alkylOR$^f$, —C$_{1-6}$alkylNR$^a$R$^e$, —S(=O)$_n$R$^e$, —S(=O)$_2$NR$^f$R$^f$, —NR$^a$S(=O)$_2$R$^e$ and —OC(=O)NR$^a$R$^f$, and the ring is additionally substituted by 0, 1, 2, 3, 4 or 5 substituents independently selected from Br, Cl, F and I;

R$^k$ is, independently, in each instance, C$_{1-9}$alkyl or C$_{1-4}$alkyl(phenyl) wherein either is substituted by 0, 1, 2, 3 or 4 substituents selected from halo, C$_{1-4}$haloalkyl, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkylNR$^a$R$^a$, —OC$_{2-6}$alkylOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$ NR$^a$R$^a$, —NR$^a$C$_{2-6}$alkylNR$^a$R$^a$ and —NR$^a$C$_{2-6}$alkylOR$^a$; and wherein the C$_{1-9}$alkyl is additionally substituted by 0 or 1 groups independently selected from R$^h$ and additionally substituted by 0, 1, 2, 3, 4 or 5 substituents independently selected from Br, Cl, F and I;

R$^m$ is, independently, in each instance, R$^e$ or H; and

R$^n$ is, independently, in each instance, a saturated, partially saturated or unsaturated 5- or 6-membered monocyclic ring containing 1, 2 or 3 atoms selected from N, O and S, so long as the combination of O and S atoms is not greater than 2, wherein the ring is substituted by 0 or 1 oxo or thioxo groups.

2. A compound according to claim 1, or any pharmaceutically-acceptable salt thereof, wherein J is NH.

3. A compound according to claim 1, or any pharmaceutically-acceptable salt thereof, wherein J is O.

4. A compound according to claim 1, or any pharmaceutically-acceptable salt thereof, wherein X$^1$ and X$^2$ are both C; and R$^1$ is —OR$^b$ or C$_{1-6}$alkyl substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by 0 or 1 substituents selected from a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 1, 2 or 3 substituents selected from C$_{1-8}$alkyl, C$_{1-4}$haloalkyl, halo, cyano, nitro, —C(=O)R$^b$, —C(=O)OR$^b$, C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)

OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$; or R$^1$ is C$_{1-6}$heteroalkyl chain substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from C$_{1-8}$alkyl, C$_{1-4}$haloalkyl, halo, cyano, nitro, —C(=O)R$^b$, —C(=O)OR$^b$C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$ NR$^a$R$^a$, —NR$^a$C$_{2-6}$alkylNR$^a$R$^a$ and —NR$^a$C$_{2-6}$alkylOR$^a$.

5. A compound according to claim 1, or any pharmaceutically-acceptable salt thereof, wherein X$^1$ and X$^2$ are both C; and R$^1$ is C$_{1-6}$alkyl substituted by 0, 1, 2 or 3 substituents independently selected from C$_{1-4}$haloalkyl, halo, cyano, oxo, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$NR$^a$R$^a$, —NR$^a$C$_{2-6}$alkylNR$^a$R$^a$ and —NR$^a$C$_{2-6}$alkylOR$^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 1, 2 or 3 substituents selected from C$_{1-8}$alkyl, C$_{1-4}$haloalkyl, halo, cyano, nitro, —C(=O)R$^b$, —C(=O)OR$^b$, —C(=O)NR$^a$R$^a$, —C(=NR$^a$)NR$^a$R$^a$, —OR$^a$, —OC(=O)R$^b$, —OC(=O)NR$^a$R$^a$, —OC(=O)N(R$^a$)S(=O)$_2$R$^b$, —OC$_{2-6}$alkylNR$^a$R$^a$, —OC$_{2-6}$alkylOR$^a$, —SR$^a$, —S(=O)R$^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$ NR$^a$R$^a$, —NR$^a$C$_{2-6}$alkylNR$^a$R$^a$ and —NR$^a$C$_{2-6}$alkylOR$^a$.

6. A compound according to claim 1, or any pharmaceutically-acceptable salt thereof, wherein
at least one of $X^1$ and $X^2$ is N;
J is NH; and
$R^1$ is $C_{1-6}$alkyl substituted by 0, 1, 2 or 3 substituents independently selected from $C_{1-4}$haloalkyl, halo, cyano, oxo, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and additionally substituted by a substituent selected from i) a saturated, partially saturated or unsaturated 5-, 6- or 7-membered ring containing 1, 2, 3 or 4 atoms selected from N, O and S, wherein the carbon atoms of the ring are substituted by 0, 1 or 2 oxo groups and the ring is substituted by 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$—OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$; and ii) phenyl substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —C(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$; or $R^1$ is $C_{1-6}$heteroalkyl chain substituted by 0, 1, 2 or 3 substituents independently selected from $C_{1-4}$haloalkyl, halo, cyano, oxo, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and additionally substituted by a saturated, partially saturated or unsaturated 5-, 6- or 7-membered ring containing 0, 1, 2, 3 or 4 atoms selected from N, O and S, wherein the carbon atoms of the ring are substituted by 0, 1 or 2 oxo groups and the ring is substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^a$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$.

7. A compound according to claim 1, or any pharmaceutically-acceptable salt thereof, wherein
at least one of $X^1$ and $X^2$ is N;
J is NH; and
$R^1$ is $C_{1-6}$alkyl substituted by 0, 1, 2 or 3 substituents independently selected from $C_{1-4}$haloalkyl, halo, cyano, oxo, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, And additionally substituted by a saturated, partially saturated or unsaturated 5-, 6- or 7-membered ring containing 1, 2, 3 or 4 atoms selected from N, O and S, wherein the carbon atoms of the ring are substituted by 0, 1 or 2 oxo groups and the ring is substituted by 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$.

8. A compound according to claim 1, or any pharmaceutically-acceptable salt thereof, wherein
at least one of $X^1$ and $X^2$ is N;
J is NH; and
$R^1$ is $C_{1-6}$alkyl substituted by 0, 1, 2 or 3 substituents independently selected from $C_{1-4}$haloalkyl, halo, cyano, oxo, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2R^b$, —S(=O)$_2$N$R^aR^a$, —S(=O)$_2$N($R^a$)C(=O)$R^b$, —S(=O)$_2$N($R^a$)C(=O)O$R^b$, —S(=O)$_2$N($R^a$)C(=O)N$R^aR^a$, —N$R^aR^a$, —N($R^a$)C(=O)$R^b$, —N($R^a$)C(=O)O$R^b$, —N($R^a$)C(=O)N$R^aR^a$, —N($R^a$)C(=N$R^a$)N$R^aR^a$, —N($R^a$)S(=O)$_2R^b$, —N($R^a$)S(=O)$_2$N$R^aR^a$, —N$R^aC_{2-6}$alkylN$R^aR^a$ and —N$R^aC_{2-6}$alkylO$R^a$, and additionally substituted by phenyl substituted by 0, 1, 2 or 3 substituents selected from $C_{1-8}$alkyl, $C_{1-4}$haloalkyl, halo, cyano, nitro, —C(=O)$R^b$, —C(=O)O$R^b$, —C(=O)N$R^aR^a$, —C(=N$R^a$)N$R^aR^a$, —O$R^a$, —OC(=O)$R^b$, —OC(=O)N$R^aR^a$, —OC(=O)N($R^a$)S(=O)$_2R^b$, —O$C_{2-6}$alkylN$R^aR^a$, —O$C_{2-6}$alkylO$R^a$, —S$R^a$, —S(=O)$R^b$, —S(=O)$_2$R$^b$, —S(=O)$_2$NR$^a$R$^a$, —S(=O)$_2$N(R$^a$)C(=O)R$^b$, —S(=O)$_2$N(R$^a$)C(=O)OR$^b$, —S(=O)$_2$N(R$^a$)C(=O)NR$^a$R$^a$, —NR$^a$R$^a$, —N(R$^a$)C(=O)R$^b$, —N(R$^a$)C(=O)OR$^b$, —N(R$^a$)C(=O)NR$^a$R$^a$, —N(R$^a$)C(=NR$^a$)NR$^a$R$^a$, —N(R$^a$)S(=O)$_2$R$^b$, —N(R$^a$)S(=O)$_2$ NR$^a$R$^a$, —NR$^a$C$_{2-6}$alkylNR$^a$R$^a$ and —NR$^a$C$_{2-6}$alkylOR$^a$.

9. A compound according to claim 1, or any pharmaceutically-acceptable salt thereof, wherein R$^2$ is C$_{1-6}$alkyl and n is 1.

10. A compound according to claim 1, or any pharmaceutically-acceptable salt thereof, wherein n and m are both 0.

11. A compound according to claim 1, wherein the compound is selected from:
- 4-((6-(4-(1,1-dimethylethyl)-1-cyclohexen-1-yl)-4-pyrimidinyl)oxy)-1,3-benzothiazol-2-amine;
- 4-((6-(4-(trifluoromethyl)-1-cyclohexen-1-yl)-4-pyrimidinyl)oxy)-1,3-benzothiazol-2-amine;
- 5-[(6-{4-[(1R)-1-(4-fluorophenyl)ethyl]piperazin-1-yl}pyrimidin-4-yl)amino]-2H-1,4-benzoxazin-3(4H)-one;
- 5-[(6-{4-[(1S)-1-(4-fluorophenyl)ethyl]piperazin-1-yl}pyrimidin-4-yl)amino]-1,3-dihydro-2H-indol-2-one;
- 6-[(6-{4-[(1S)-1-(4-fluorophenyl)ethyl]piperazin-1-yl}pyrimidin-4-yl)amino]-2H-1,4-benzoxazin-3(4H)-one;
- 7-[(6-{4-[(1S)-1-(4-fluorophenyl)ethyl]piperazin-1-yl}pyrimidin-4-yl)amino]-3,4-dihydroquinolin-2(1H)-one;
- N-(2,3-dihydro-1,4-benzodioxin-6-yl)-6-{4-[(1S)-1-(4-fluorophenyl)ethyl]piperazin-1-yl}pyrimidin-4-amine;
- N-(4-((6-(4-((1R)-1-(4-fluorophenyl)ethyl)-1-piperazinyl)-4-pyrimidinyl)amino)-1,3-benzothiazol-2-yl)acetamide;
- N-(4-((6-(4-(1,1-dimethylethyl)-1-cyclohexen-1-yl)-4-pyrimidinyl)oxy)-1,3-benzothiazol-2-yl)acetamide;
- N-(4-((6-(4-(trifluoromethyl)-1-cyclohexen-1-yl)-4-pyrimidinyl)oxy)-1,3-benzothiazol-2-yl)acetamide;
- N-(4-((6-(4-(trifluoromethyl)Cyclohexyl)-4-pyrimidinyl)oxy)-1,3-benzothiazol-2-yl)acetamide;
- N-(6-(4-((1R)-1-(4-fluorophenyl)ethyl)-1-piperazinyl)-4-pyrimidinyl)-7-quinolinamine;
- N-(6-(4-((1S)-1-(4-fluorophenyl)ethyl)-1-piperazinyl)-4-pyrimidinyl)-7-quinolinamine; and
- N-(6-{4-[(1S)-1-(4-fluorophenyl)ethyl]piperazin-1-yl}pyrimidin-4-yl)-1,3-benzothiazol-5-amine;

or a pharmaceutically-acceptable salt thereof.

12. A pharmaceutical composition comprising a compound according to claim 1 and a pharmaceutically-acceptable diluent or carrier.

* * * * *